US006921534B2

(12) United States Patent
Mizzen et al.

(10) Patent No.: US 6,921,534 B2
(45) Date of Patent: Jul. 26, 2005

(54) HEPATITIS B VIRUS TREATMENT

(75) Inventors: Lee A. Mizzen, Victoria (CA); Marvin Siegel, Blue Bell, PA (US); Hongwei Liu, Victoria (CA)

(73) Assignee: Stressgen Biotechnologies Corporation, Victoria (CA)

( * ) Notice: Subject to any disclaimer, the term of this patent is extended or adjusted under 35 U.S.C. 154(b) by 201 days.

(21) Appl. No.: 10/068,059

(22) Filed: Feb. 5, 2002

(65) Prior Publication Data

US 2002/0155434 A1 Oct. 24, 2002

Related U.S. Application Data

(60) Provisional application No. 60/266,733, filed on Feb. 5, 2001.

(51) Int. Cl.$^7$ .................... A61K 39/29; C12N 15/36; C12N 15/62; C07K 19/00; C07K 14/02
(52) U.S. Cl. ................. 424/189.1; 530/350; 424/192.1; 424/199.1; 424/227.1; 514/44; 536/23.4; 536/23.72; 435/320.1; 435/325; 435/252.3; 435/69.3
(58) Field of Search .................. 530/350; 424/189.1, 424/192.1, 199.1, 227.1; 514/44; 536/23.4, 23.72; 435/320.1, 325, 252.3, 69.3

(56) References Cited

U.S. PATENT DOCUMENTS

| | | | |
|---|---|---|---|
| 4,547,368 A | * 10/1985 | Tabor et al. ............. 424/227.1 |
| 4,716,038 A | 12/1987 | Stanford et al. ............... 424/92 |
| 4,724,144 A | 2/1988 | Rook et al. .................... 424/93 |
| 4,918,166 A | 4/1990 | Kingsman et al. .......... 530/350 |
| 5,114,844 A | 5/1992 | Cohen et al. .................... 435/7 |
| 5,348,945 A | 9/1994 | Berberian et al. ............. 514/21 |
| 5,504,005 A | 4/1996 | Bloom et al. ................ 435/253 |
| 5,578,300 A | 11/1996 | Schmidt et al. .......... 424/78.08 |
| 5,580,563 A | 12/1996 | Tam ........................... 424/197 |
| 5,599,545 A | 2/1997 | Stanford et al. ......... 424/282.1 |
| 5,736,146 A | 4/1998 | Cohen et al. .......... 424/197.11 |
| 5,750,119 A | 5/1998 | Srivastava ................ 424/277.1 |
| 5,830,464 A | 11/1998 | Srivastava ................ 424/93.71 |
| 5,837,251 A | 11/1998 | Srivastava ................ 424/193.1 |
| 5,935,576 A | 8/1999 | Srivastava ................ 424/184.1 |
| 5,948,646 A | 9/1999 | Srivastava ................. 435/69.3 |
| 5,961,979 A | 10/1999 | Srivastava ................ 424/193.1 |
| 5,985,270 A | 11/1999 | Srivastava ................ 424/93.71 |
| 5,997,873 A | 12/1999 | Srivastava ................ 424/193.1 |
| 6,007,821 A | 12/1999 | Srivastava et al. ........ 424/193.1 |
| 6,017,540 A | 1/2000 | Srivastava et al. ........ 424/193.1 |
| 6,017,544 A | 1/2000 | Srivastava ................ 424/277.1 |
| 6,020,167 A | * 2/2000 | Thoma ...................... 435/69.3 |
| 6,030,618 A | 2/2000 | Srivastava ................ 424/184.1 |
| 6,048,530 A | 4/2000 | Srivastava ................ 424/193.1 |
| 6,130,087 A | 10/2000 | Srivastava et al. ........ 435/372.3 |
| 6,136,315 A | 10/2000 | Srivastava ................ 424/193.1 |
| 6,139,841 A | 10/2000 | Srivastava ................ 424/193.1 |
| 6,143,299 A | 11/2000 | Srivastava ................ 424/193.1 |
| 6,156,302 A | 12/2000 | Srivastava ................. 424/93.1 |
| 6,162,436 A | 12/2000 | Srivastava ................ 424/193.1 |
| 6,168,793 B1 | 1/2001 | Srivastava ................ 424/193.1 |
| 6,187,312 B1 | 2/2001 | Srivastava ................ 424/193.1 |
| 6,231,864 B1 | * 5/2001 | Birkett .................... 424/189.1 |
| 6,297,048 B1 | * 10/2001 | Jolly et al. ............... 435/320.1 |
| 6,322,790 B1 | 11/2001 | Srivastava ................ 424/193.1 |
| 6,335,183 B1 | 1/2002 | Young et al. ............... 435/69.7 |
| 6,338,952 B1 | 1/2002 | Young et al. ............... 435/69.7 |
| 6,388,952 B2 | * 5/2002 | Young et al. ............... 435/69.7 |

FOREIGN PATENT DOCUMENTS

| | | |
|---|---|---|
| EP | 0 262 710 | 4/1988 |
| EP | 0 322 990 | 7/1989 |
| GB | 2 251 186 | 7/1992 |
| WO | WO 85/05034 | 11/1985 |
| WO | WO 88/00974 | 2/1988 |
| WO | WO 88/05823 | 8/1988 |
| WO | WO 88/06591 | 9/1988 |
| WO | WO 89/12455 | 12/1989 |
| WO | WO 90/15873 | 12/1990 |
| WO | WO 91/02542 | 3/1991 |
| WO | WO 91/15572 | 10/1991 |
| WO | WO 92/08484 | 5/1992 |
| WO | WO 92/08488 | 5/1992 |
| WO | WO 93/17712 | 9/1993 |
| WO | WO 94/03208 | 2/1994 |
| WO | WO 94/29459 | 12/1994 |
| WO | WO 95/24923 | 9/1995 |
| WO | WO 95/31994 | 11/1995 |
| WO | WO 97/06821 | 2/1997 |
| WO | WO 97/26910 | 7/1997 |
| WO | WO 98/23735 | 6/1998 |
| WO | 98/23735 | * 6/1998 ........... C12N/15/10 |
| WO | WO 98/34641 | 8/1998 |
| WO | WO 98/35705 | 8/1998 |
| WO | WO 99/07860 | 2/1999 |
| WO | WO 00/19828 | 4/2000 |
| WO | WO 00/23093 | 4/2000 |
| WO | WO 01/04344 | 1/2001 |
| WO | WO 02/14370 | 2/2001 |
| WO | WO 01/17554 | 3/2001 |
| WO | WO 01/52791 | 7/2001 |
| WO | WO 01/52877 | 7/2001 |
| WO | WO 01/52890 | 7/2001 |
| WO | WO 01/53457 | 7/2001 |
| WO | WO 02/00242 | 1/2002 |

OTHER PUBLICATIONS

Gunther et al (Hepatology 24(4), 751□758, 1996).*
Yuan et al (Journal of Virology 73:10122–10128, 1999).*
CAA59535 [online] [retrieved 7/22/04]Retrieved from NCBI Entrez Protein http://www.ncbi.nlm.nih.gov/entrez.viewer.fcgi?db=protein&val=762935.*

(Continued)

Primary Examiner—Mary E. Mosher
(74) Attorney, Agent, or Firm—Fish & Richardson P.C.

(57) ABSTRACT

The invention relates to HBV antigen-containing compositions that are useful in treating or preventing HBV infection. The content of the compositions can vary, as described herein, but the compositions comprise a stress protein, or a portion (e.g., a fragment) or derivative thereof, and an HBV antigen.

70 Claims, 20 Drawing Sheets

OTHER PUBLICATIONS

Figure 13:
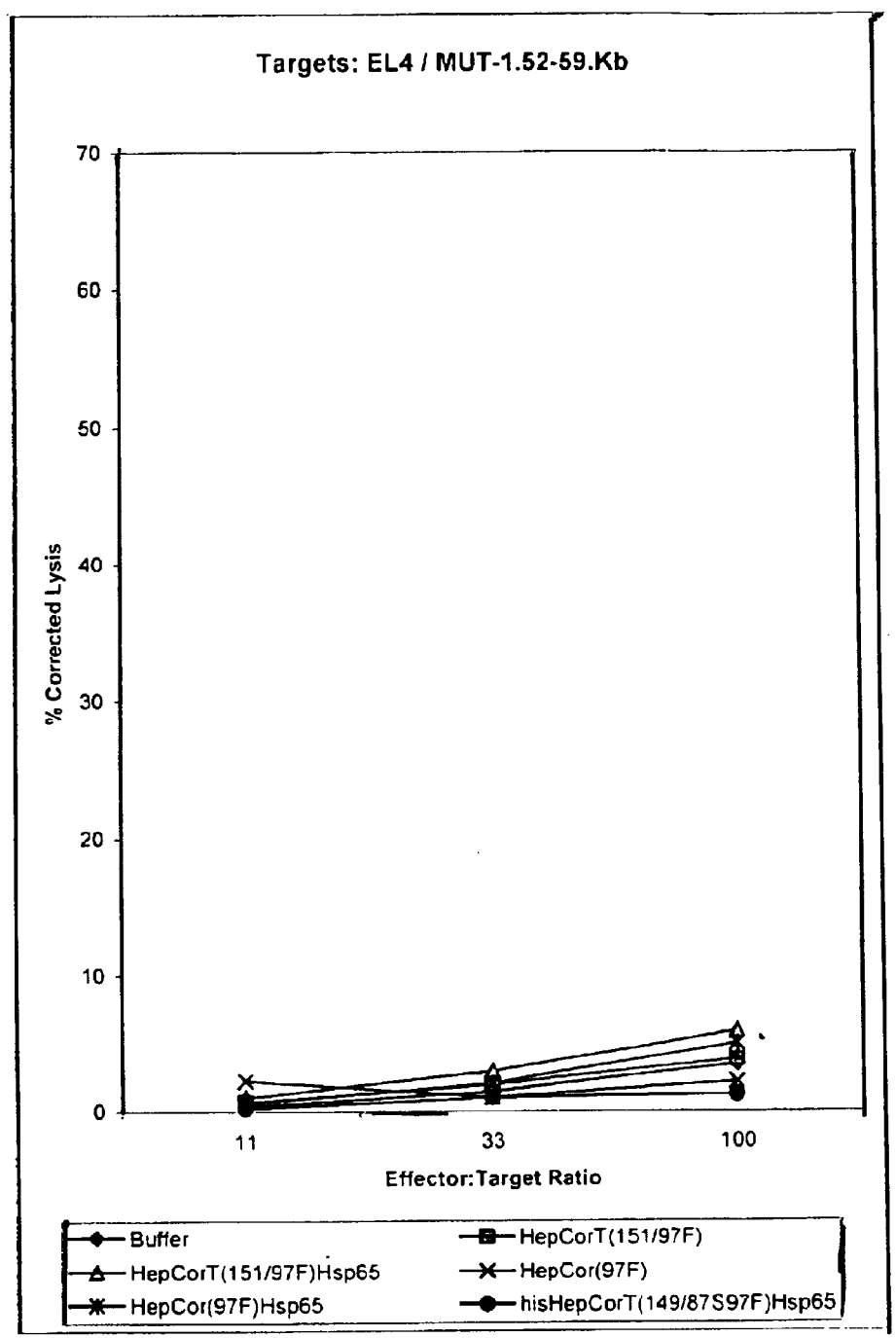

Chen et al. (2004) "Recombinant hepatitis B core antigen carrying preS1 epitopes induce immune response against chronic HBV infection" Vaccine 22(3–4):439–46.

Agranovsky et al., "Putative 65 kDa Protein of Beet Yellows Closterovirus Is a Homologue of HSP70 Heat Shock Proteins," J. Mol. Biol., 217:603–610 (1991).

Anthony et al., "Priming of CD8+ CTL Effector Cells In Mice By Immunization With a Stress Protein–Influenza Virus Nucleoprotein Fusion Molecule", Vaccine, 17:373–383 (1999).

Ardeshir et al., "A 75 Kd Merozoite Surface Protein of Plasmodium Falciparum which is Related to the 70 kd Heat–Shcok Proteins," EMBO J., 6(2):493–499 (1987).

Arnosti et al., "Characterization of heat shock in Bacillus subtilis," J. Bact., 168(3):1243–1249 (Dec. 1986).

Arrigo and Welch, "Characterization and Purification of the Small 28,000–Dalton Mammalian Heat Shock Protein", J. Biol. Chem., 262(32):15329–15369 (1987).

Barrios et al., "Heat shock proteins as carrier molecules: in vivo helper effect mediated by Escherichia coli GroEL and DnaK proteins requires cross–linking with antigen," Clin. Exp. Immunol., 98:229–233 (1994).

Barrios et al., "Mycobacterial heat–shock proteins as carrier molecules. II: The use of the 70–kDa mycobacterial heat–shock protein as carrier for conjugated vaccines can circumvent the need for adjuvants and Bacillus Calmette Guerin priming," Eur. J. Immunol., 22:1365–1372 (1992).

Beech et al., "CD4+ Th2 cells specific for mycobacterial 65–kilodalton heat shock protein protect against pristane–induced arthritis," J. Immunol. 159:3692–3697 (1997).

Bennett et al., "Help for Cytotoxic–T–cell Responses is Mediated by CD40 Signalling," Nature 393:478–480 (Jun. 4, 1998).

Bertelli et al., "BCG–Induced Resistance in Trypanosoma cruzi Experimental Infections," Tropenmed Parasitol, 32:93–96 (1981).

Birk et al., "T–cell autoimmunity in type 1 diabetes mellitus," Curr. Opin. Immunol., 5:903–909 (1993).

Blachere et al., "Heat Shock Protein–Peptide Complexes, Reconstituted in Vitro, Elicit Peptide–specific Cytotoxic T Lymphocyte Response and Tumor Immunity," J. Exp. Med. 186(8):1315–1322 (Oct. 20, 1997).

Blander and Horwitz, "Major Cytoplasmic Membrane Protein of Legionella Pneumophila, a Genus Common Antigen and Member of the hsp 60 Family of Heat Shock Proteins, Induces Protective Immunity in a Guinea Pig Model of Legionnaires' Disease," J. Clin. Invest., 91:717–723 (1993).

Breloer et al., "In Vivo and In Vitro Activation of T Cells After Administration of Ag–Negative Heat Shock Proteins," J. of Immun. 162:3141–3147 (1999).

Cassell et al., "A Phase II Study on the Postsurgical Management of Stage Malignant Melanoma With a Newcastle Disease Virus Oncolysate," Cancer, 52:856–860 (Sep. 1983).

Cassell et al., "Viral Oncolysate in the Management of Malignant Melanoma, I. Preparation of the Oncolysate and Measurement of Immunologic Responses" Cancer, 40:672–679 (Aug. 1977).

Catelli et al., "The common 90–kd protein component of non–transformed '8S' steroid receptors is a heat–shock protein", EMBO J., 4(12):3131–3135 (1985).

Chandrasekhar et al., "Purification and Properties of the groES Morphogenetic Protein of Escherichia coli", J. Biol. Chem., 261(26):12414–12419 (1986).

Chen et al., "Human 60–kDa Heat–Shock Protein: A Danger Signal to the Innate Immune System," J. of Immunol. 162:3212–3219 (1999).

Chu et al., "Cancer Immunotherapy Using Adjuvant–free, Fusion Protein Encoding M. bovis BCG HSP65 and HPV16 E7", Faseb Journal, 12(5):A909 (Mar. 20, 1998).

Chu et al., "Immunotherapy of a Human Papillomavirus (HPV) Type 16 E7–Expressing Tumour By Administration of Fusion Protein Comprising Mycobacteria bovis Bacille Calmette–Guérin (BCG) hsp65 and HPV16 E7", Clin. Exp. Immunol., 121:216–226 (2000).

Cohen et al., "Immunity to 60 kDa heat shock protein in autoimmune diabetes," Diab. Nutr. Metab., 9(4):229–232 (1996).

Cohen, "Jitters jeopardize AIDS vaccine trials," Science, 262: 980–981 (1993).

Dahlseid et al., "PBP74, a new member of the mammalian 70–kDa heat shock protein family, is a mitochondrial protein," Mol Biol Cell. 5(11):1265–1275 (1994).

De Velasco et al., "Synthetic Peptides Representing T–Cell Epitopes Act as Carriers in Pneumococcal Polysaccharide Conjugate Vaccines," Infect. & Immun., 63:961–968 (1995).

Del Guidice, "Hsp70: a carrier molecule with built–in adjuvanticity," Experientia, 50:1061–1066 (1994).

Del Guidice et al., "Heat shock proteins as "super"–carriers for sporozoite peptide vaccines?", Research in Immunol., 162:703–707 (1991).

Del Guidice et al., "Priming to Heat Shock Proteins in Infants Vaccinated against Pertussis," J. Immunol., 150(5):2025–2032 (1993).

DeNagel et al., "Heat shock proteins in Immune Responses," Crit. Rev. Immunol., 13(1):71–81 (1993).

Doherty et al, "Evasion of host immune responses by tumours and viruses," Vaccines Against Virally Induced Cancers, Wiley, Chicester (Ciba Foundation Symposium 187), pp. 245–260. See p. 245, Abstract.

DuBois et al., "Isolation of a Tumor–Associated Transplantation Antigen (TATA) From an SV40–Induced Sarcoma. Resemblance to the TATA of Chemically Induced Neoplasms," Int. J. Cancer, 34:561–566 (1984).

Dubois et al., "Protective immunization of the squirrel monkey against asexual blood stages of Plasmodium falciparum by use of parasite protein fractions," Proc. Natl. Acad. Sci., 81:229–232 (1984).

Elias et al., "Induction and therapy of autoimmune diabetes in the non–obese diabetic (NOD/Lt) mouse by a 65–kDa heat shock protein," Proc. Natl. Acad. Sci. USA, 87:1576–1580 (1990).

Falk et al., "Cell Mediated Immunity to Human Tumors," Arch. Surg., 107:261–265 (Aug. 1973).

Ferrero et al., "The GroES homolog of Helicobacter pylori confers protective immunity against mucosal infection in mice," Proc. Natl. Acad. Sci. USA, 92:6499–6503 (1995).

Flaherty et al., "Three–dimensional Structure of the ATPase Fragment of a 70K Heat–Shock Cognate Protein," Nature 346:623–628.

Fox, "No Winners Against AIDS", Biotechnology, 12:128 (1994).

Friedland et al., "Mycobacterial 65–kD heat shock protein induces release of proinflammatory cytokines from human monocytic cells," Clin. Exp. Immunol., 91:58–62 (1993).

Gomes et al., "Heat shock protein synthesis during development in *Caulobacter crescentus*," J. Bact., 168(2):923–930 (Nov. 1986).

Gomez et al., "Vaccination with Recombinant Heat Shock Protein 60 from *Histoplasma capsulatum* Protects Mice against Pulmonary Histoplasmosis," Infect. & Immun., 63:2587–2595 (1995).

Haanen et al., "Selection of a human T helper type 1–like T cell subset by mycobacteria," J. Exp. Med., 174:583–592 (1991).

Haghbin et al., "Immunotherapy with Oral BCG and Serial Immune Evaluation in Childhood Lymphoblastic Leukemia Following Three Years of Chemotherapy," Cancer, 46:2577–2586 (Dec. 1980).

Hastie et al., "HSP27 Elevated in Mild Allergic Inflammation Protects Airway Epithelium from H2SO4 Effects," Am J. Physiol., 273 (Lung Cell. Mol. Physiol. 17):L401–L409 (1997).

Huang et al., "In Vivo Cytotoxic T Lymphocyte Elicitation by Mycobacterial Heat Shock Protein 70 Fusion Proteins Maps to a Discrete Domain and Is CD4 T Cell Independent," J. Exp. Med. 191(2):403–408 (Jan. 17, 2000).

Hudson et al., "Active Specific Immunotherapy for Ovarian Cancer," The Lancet, 2:877–879 (Oct. 23, 1976).

Hughes et al., "A Study in Clinical Cancer Immunotherapy," Cancer, 26:269–278 (Aug. 1970).

Humphrey et al., "Adjuvant Immunotherapy for Melanoma," J. of Sur. Oncol., 25:303–305 (1984).

Hunt and Calderwood, "Characterization and Sequence of a Mouse hsp70 Gene and Its Expression in Mouse Cell Lines," Gene 87:199–204 (1990).

Husson and Young, "Genes for the major protein antigens of Mycobacterium tuberculosis: The etiologic agents of tuberculosis and leprosy share an immunodominant antigen," Proc. Natl. Acad. Sci. USA, 84:1679–1683 (1987).

Huygen et al., "Spleen cell cytokine secretion in *Mycobacterium bovis* BCG–infected mice," Infection and Immunity, 60(7):2880–2886 (1992).

Jacquier–Sarlin, "Protective effects of hsp70 in inflammation," Experientia, 50(11–12):1031–1038 (1994).

Jarecki–Black et al., "The Effect of BCG–Vaccine Upon Experimental Visceral Leishmaniasis in Hampsters," Ann. Clin. Lab. Sci., 14:464–466 (1984).

Jindal, "Heat Shock Proteins: Applications in health and disease," Trends in Biotech, 14(1):17–20, 1996.

Jondal et al., "MHC Class I–Restricted CTL Responses to Exogenous Antigens," Immunity 5:295–203 (Oct. 1996).

Kaufmann et al., "Enumeration of T cells reactive with Mycobacterium tuberculosis organisms and specific for the recombinant mycobacterial 64–kDa protein", Eur. J. Immunol., 17:351–357 (1987).

Kaufmann et al., "Heat–shock protein 60: implications for pathogenesis of and protection against bacterial infections," Immunological Reviews, 121:67–90 (1991).

Kiessling et al., "Role of hsp60 during autoimmune and bacterial inflammation," Immunological Reviews, 121:91–111 (1991).

Kimmig and Wenk, "Suppression of Parasitaemia from *Litomosoides carinii* by Immunisation with BCG and Microfilariae," Z. Parasitenkd, 67:317–327 (1982).

Kol et al., "Chlamydial and Human Heat Shock Protein 60s Activate Human Vascular Endothelium, Smooth Muscle Cells, and Macrophages," J. Clin. Invest. 103:571–577 (1999).

Konen–Waisman et al., "Self and Foreign 60–Kilodalton Heath Shock Protein T Cell Epitope Peptides Serve As Immunogenic Carriers for a T Cell–Independent Sugar Antigen," Journ. Immunol., 154:5977–5985 (1995).

Konen–Waisman et al., "Self Heat–Shock Protein (hsp60) Peptide Serves in a Conuugate Vaccine against a Lethal Pneumococcal Infection," J. Infect. Diseases 179:403–413 (1999).

La Thangue and Latchman, "A Cellular Protein Related to Heat–Shocked Protein 90 Accumulates during Herpes Simplex Virus Infection and Is Overexpressed in Transformed Cells," Experimental Cell Research, 178:169–179 (1988).

Lamb et al., "Stress Proteins may Provice a Link Between the Immune Response to Infection and Autoimmunity", Int'l. Immun., 1(2):191–196 (1989).

Leung et al., "The immunobiology of heat shock proteins," J. Investig. Allergol. Clin. Immunol., 1(1):23–30, (1991).

Li and Srivastava, "Tumor Rejection Antigen gp96/grp94 is an ATPase: Implications for Protein Folding and Antigen Presentation," The EMBO Journal, 12(8):3143–3151 (1993).

Lindquist and Craig, "The Heat–Shock Proteins," Annu. Rev. Genet., 22:631–677 (1988).

Lussow et al., "Mycobacterial heat–shocked proteins as carrier molecules," Eur. J. Immunol., 21:2297–2302 (1991).

Maytin, "Heat shock proteins and molecular chaperones: implications for adaptive responses in the skin," J. Invest. Dermatol., 104:448–455 (1995).

McCulloch et al., "Recurrent Malignant Melanoma: Effect of Adjuvant Immunotherapy on Survival," Can. Med. Assoc. J., 117:33–36 (Jul. 1977).

Meng et al., "HBV–specific peptide associated with heat–shock protein gp96," Lancet 357:528–529 (2001).

Miller et al., "Immunotherapy in autoimmune diseases," Curr. Opinion in Immun., 3:936–940 (1991).

Minowada et al., "Clinical implications of the stress response," J. Clin. Invest., 95:3–12 (1995).

Moréet al., Activation of cytotoxic T cells in vitro by recombinant gp96 fusion proteins irrespective of the 'fused' antigenic peptide sequence, Immunology Letters, 69:275–282 (1992).

Murphy and Lefford, "Host Defenses in Murine Malaria: Induction of a Protracted State of Immunity with a Formalin–Killed *Plasmodium berghei* Blood Parasite Vaccine," Infec. Immun., 22:798–803 (1978).

Murray et al., "Viral Oncolysate in the Management of Malignant Melanoma, II. Clinical Studies" Cancer, 40:680–686 (Aug. 1977).

Nadler et al., "Interaction of the Immunosupressant Deoxyspergualin with a Member of the Hsp70 Family of Heat Shock Proteins," Science, 258:484–486 (1992).

Nair et al., "Calreticulin Displays in Vivo Peptide–Binding Activity and Can Elicit CTL Responses Against Bound Peptides," J. Immun. 162:6426–6432 (1999).

Noll and Autenrietie, "Immunity against *Yersinia enterocolitica* by Vaccination with Yersinia HSP60 Immunostimulating Complexes or Yersinia HSP60 plus Interleukin–12", Infect. & Immun., 64:2955–2961 (1996).

Oettgen and Old, "Chapter 6: The History of Cancer Immunotherapy." In Biologic Therapy of Cancer, De Vita, V.T., Hellman, S. and Rosenberg, S.A., eds., (London: J.B. Lippincott) pp. 98–103 (1991).

Orme et al., "Cytokine secretion by CD4 T lymphocytes acquired in response to Mycobacterium tuberculosis infection," J. Immunol., 151(1):518–525 (1993).

Palladino et al., "Expression of a Shared Tumor–Specific Antigen by Two Chemically Induced BALB/c Sarcomas," Cancer Research, 47:5074–5079 (Oct. 1987).

Peetermans et al., "Mycobacterial heat–shock protein 65 induces proinflammatory cytokines but does not activate human mononuclear phagocytes," Scan. J. Immunol., 39:613–617 (1994).

Pinskey et al., "Intravesical Administration of Bacillus Calmette–Guerin in Patients with Recurrent Superficial Carcinoma of the Urinary Bladder: Report of a Prospective Trail," Cancer Treat. Rep., 69:47–53 (Jan. 1985).

Polla et al., "Heat shock proteins and inflammation," Current Topics in Microbiology and Immunology, 167:93–105 (1991).

Polla et al., "Regulation and functions of stress proteins in allergy and inflammation," Clinical and Experimental Allergy, 23:548–556 (1993).

Polla et al., "Spontaneous heat shock protein synthesis by alveolar macrophages in interstitial lung disease associated with phagocytosis of eosinophils," Eur. Respir. J., 6:483–488 (1993).

Rico et al., "Characterization of the Immunostimulatory Properties of Leishmania infantum HSP70 by Fusion to the Escherichia coli Maltose–Binding Protein in Normal nu/nu Balb/c Mice," Infection and Immunity 66:347–352 (Jan. 1998).

Roman et al., "Synbthetic peptides non–covalently bound to bacterial hsp 70 elicit peptide–specific T–cell responses in vivo," Immunology, 88(4):487–492 (1992).

Schild et al., "Stress Proteins and Immunity Mediated by Cytotoxic T Lymphocytes," Current Opinion in Immun. 11:109–113 (1999).

Schoenberger et al., "T–cell Help for Cytotoxic T Lymphocytes is Mediated by CD40–CD40L Interactions," Nature 393:480–483 (Jun. 4, 1998).

Shinnick et al., "The Etiologicl Agents of Leprosy and Tuberculosis Share an Immunoreactive protein Antigen with the Vaccine Strain Mycobacterium bovis BCG", Infect. and Immun., 55(8):1932–1935 (1987).

Silverstein, "The History of Immunology," In Fundamental Immunology, 2.sup.nd Edition, Paul, W.E., ed., (NY:Raven Press), pp. 21, 23–24 (1989).

Sparks et al., "Immunology and Adjuvant Chemoimmunotherapy of Breast Cancer," Arch Surg, 111:1057–1062 (Oct. 1976).

Spencer et al., "Nonspecific Protection of Mice against Influenza Virus Infection by Local or Systemic Immunization with Bacille Calmette–Guerin," J. Infect, 171–175 (Aug. 1977).

Srivastava and Udono, "Heat Shock Protein–Peptide Complexes in Cancer Immunotherapy," Current Opinion in Immun., 6:728–732 (1994).

Srivastava and Old, "Individually Distinct Transplantation Antigens of Chemically Induced Mouse Tumors," Immunology Toady, 9:78–83 (Mar. 1988).

Srivastava and Das, "The Serologically Unique Cell Surface Antigen of Zajdela Ascitic Hepatoma is Also Its Tumor–Associated Transplantation Antigen," Int. J. Cancer, 33:417–422 (1984).

Srivastava and Maki, "Stress–Induced Proteins in Immune Response to Cancer," Curr. Top. of Microbiol. Immunol., 167:109–123 (1991).

Srivastava et al., "Tumor Rejection Antigens of Chemically Induced Sarcomas of Inbred Mice," Proc. Natl. Acad. Sci., USA, 83:3407–3411 (May 1986).

Sturrock et al., "Attempts to Induce Resistance to Schistosoma mansoni and S. haematobium in Kenyan Baboons (Papio anubis) Using Non–Specific Immunostimulants," Parasitology, 90:101–110 (1985).

Suto and Srivastava, "A Mechanism for the Specific Immunogenicity of Heat Shock Protein–Chaperoned Peptides," Science 269:1585–1588 (Sep. 15, 1995).

Suzue and Young, "Adjuvant–Free hsp70 Fusion Protein System Elicits Humoral and Cellular Immune Responses to HIV–1 p24," Journal of Immunology, 156:873–879 (1996).

Suzue et al., "Heat Shock Fusion Proteins as Vehicles for Antigen Delivery Into the Major Histocompatibility Complex Class I Presentation Pathway," Proc. Natl. Acad. Sci. USA, 94:13146–13151 (Nov. 1997).

Tamura et al., "Immunotherapy of Tumors with Autologous Tumor–Derived Heat Shock Protein Preparations," Science 278:117–120 (Oct. 3, 1997).

Thole et al., "Antigenic relatedness of a strongly immunogenic 65 kDA mycobacterial protein antigen with a similarly sized ubiquitous bacterial common antigen", Microbial Pathogenesis, 4:71–83 (1988).

Thole et al., "Characterization, Sequence Determination, and Immunogenicity of a 64–Kilodalton Protein of Mycobacterium bovis BCG Expresed in Escherichia coli K–12," Infection & Immunol., 55(6):1466–1475 (1987).

Udono et al., "Cellular Requirements for Tumor–Specific Immunity Elicited by Heat Shock Proteins: Tumor Rejection Antigen gp96 Primes CD8 T Cells in vivo," Proc. Natl. Acad. Sci. USA 91:3077–3081 (Apr. 1994).

Udono and Srivastava, "Heat Shock Protein 70–associated Peptides Elicit Specific Cancer Immunity," J. Exp. Med., 178:1391–1396 (Oct. 1993).

Ullrich et al., "A Mouse Tumor–Specific Transplantation Antigen is Heat Shock–Related Protein," Proc. Natl. Acad. Sci., USA, 83:3121–3125 (May 1986).

van Eden et al., "Cloning of the mycobacterial epitope recognized by T lymphocytes in adjuvant arthritis", Nature, 331(14):171–173 (1988).

Verdegaal et al., "Heat Shock Protein 65 Induces CD62e, CD106, and CD54 on Cultured Human Endothelial Cells and Increases Their Adhesiveness for Monocytes and Granulocytes," Jour. Immunol., 157:369–376 (1996).

Vignola et al., "Increased expression of heat shock protein 70 on airway cells in asthma and chronic bronchitis," Am. J. Respir. Cell Mol. Biol., 13:683–691 (1995).

Vodkin and Williams, "A Heat Shock Operon in Coxiella burnetii Produces a Major Antigen Homologous to a Protein in Both Mycobacteria and Escherichia coli", J. of Bacteriology, 170(3):1227–1234 (1988).

Voellmy et al. "Isolation and functional analysis of a human 70,000–dalton heat shock protein gene segment," Proc Natl Acad Sci U S A. 82(15):4949–53 (1985).

Welch et al., "Biochemical characterization of the mammalian stress proteins and identification of two stress proteins as glucose– and Ca2+–ionophore–regulated proteins," J. Biol. Chem., 258(11):7102–7111 (1983).

Welch and Feramisco, "Purification of the Major Mammalian Heat Shock Proteins", J. Biol. Chem., 257(24):14949–14959 (1982).

Welch and Feramisco, "Rapid Purification of Mammalian 70,000–Dalton Stress Proteins: Affinity of the Proteins for Nucleotides", Mol. Cell. Biol., 5(6):1229–1237 (1985).

Young et al., "The 65kDa antigen of mycobacteria—a common bacterial protein?", Immunol. Today, 8(7–8):215–219 (1987).

Young et al., "Genes for the major protein antigens of the leprosy parasite mycobacterium leprae," Nature, 316:450–452 (1985).

Young et al., "Stress proteins are immune targets in leprosy and tuberculosis," Proc. Natl. Acad. Sci. USA, 85:4267–4270 (1988).

Young, "Stress Proteins and Immunology," Annu. Rev. Immunol., 8:401–420 (1990).

Zhou, "New Fusion Protein for Immunotherapy of Venereal Disease and Cancer—Is a Heat Shock Protein of Mycobacterium Bovis", Database WPI, Derwent Publications Ltd., XP002154481, (Mar. 29, 2000), Abstract.

Zhu et al., "Structural Analysis of Substrate Binding by the Molecular Chaperone DnaK," Science 272:1606–1614 (Jun. 14, 1996).

Zylicz et al., "The grpE Protein of *Escherichia coli*", J. Biol. Chem., 262(36):17437–17442 (1987).

Zylicz and Georgopoulos, "Purification and Properties of the *Escherichia coli* dnaK Replication Protein", J. Biol. Chem., 259(14):8820–8825 (1984).

PCT International Search Report, Nov. 29, 2002.

Schirmbeck et al. (1999) "Truncated or chimeric endogenous protein antigens gain immunogenicity for B cells by stress protein–facilitated expression," Eur J. Immunol. 29:1740–1749.

U.S. application No. 08/977,787, filed Nov. 25, 1997.
U.S. application No. 09/001,737, filed Dec. 31, 1997.
U.S. application No. 09/207,388, filed Dec. 8, 1998.
U.S. application No. 09/468,041, filed Dec. 21, 1999.
U.S. application No. 09/498,918, filed Feb. 4, 2000.
U.S. application No. 09/613,303, filed Jul. 10, 2000.
U.S. application No. 09/733,179, filed Dec. 7, 2000.
U.S. application No. 09/756,543, filed Jan. 8, 2001.
U.S. application No. 09/761,534, filed Jan. 16, 2001.
U.S. application No. 09/891,823, filed Jun. 26, 2001; and.
U.S. application No. 09/932/483, filed Aug. 17, 2001.

* cited by examiner

ATGGACATTGACCCTTATAAAGAATTTGGAGCTACTGTGGAGTTACTCTCGTTTTTGCC
TTCTGACTTCTTTCCTTCCGTCAGAGATCTCCTAGACACCGCCTCAGCTCTGTATCGGG
AAGCCTTAGAGTCTCCTGAGCATTGCTCACCTCACCACACCGCACTCAGGCAAGCCATT
CTCTGCTGGGGGGAATTGATGACTCTAGCTACCTGGGTGGGTAATAATTTGGAAGATCC
AGCATCAAGGGATCTAGTAGTCAATTATGTTAATACTAACATGGGTTTAAAAATTAGGC
AACTATTGTGGTTTCATATATCTTGCCTTACTTTTGGAAGAGAGACTGTACTTGAATAT
TTGGTATCTTTCGGAGTGTGGATTCGCACTCCTCCAGCCTATAGACCACCAAATGCCCC
TATCTTATCAACACTTCCGGAAACTACTGTTGTTAGACGACGGGACCGAGGCAGGTCCC
CTAGAAGAAGAACTCCCTCGCCTCGCAGACGCAGATCTCAATCGCCGCGTCGCAGAAGA
TCTCAATCTCGGGAATCTCAATGTTGA (SEQ ID NO:1)

Fig. 1

MDIDPYKEFGATVELLSFLPSDFFPSVRDLLDTASALYREALESPEHCSPHHTALRQAI
LCWGELMTLATWVGNNLEDPASRDLVVNYVNTNMGLKIRQLLWFHISCLTFGRETVLEY
LVSFGVWIRTPPAYRPPNAPILSTLPETTVVRRRDRGRSPRRRTPSPRRRRSQSPRRRR
SQSRESQC  (SEQ ID NO:2)

Fig. 2

ATGGGCAGCAGCCATCATCATCATCATCACAGCAGCGGCCTGGTGCCGCGCGGCAGCCA
TATGGACATTGACCCTTATAAAGAATTTGGAGCTACTGTGGAGTTACTCTCGTTTTTGC
CTTCTGACTTCTTTCCTTCCGTCAGAGATCTCCTAGACACCGCCTCAGCTCTGTATCGG
GAAGCCTTAGAGTCTCCTGAGCATTGCTCACCTCACCACACCGCACTCAGGCAAGCCAT
TCTCTGCTGGGGGGAATTGATGACTCTAGCTACCTGGGTGGGTAATAATTTGGAAGATC
CAGCATCAAGGGATCTAGTAGTCAGTTATGTTAATACTAACATGGGTTTAAAATTTAGG
CAACTATTGTGGTTTCATATATCTTGCCTTACTTTTGGAAGAGAGACTGTACTTGAATA
TTTGGTATCTTTCGGAGTGTGGATTCGCACTCCTCCAGCCTATAGACCACCAAATGCCC
CTATCTTATCAACACTTCCGGAAACTACTGTTGTTAACTGA    (SEQ ID NO:3)

Fig. 3

MGSSHHHHHHSSGLVPRGSHMDIDPYKEFGATVELLSFLPSDFFPSVRDLLDTASALYR
EALESPEHCSPHHTALRQAILCWGELMTLATWVGNNLEDPASRDLVVSYVNTNMGLKFR
QLLWFHISCLTFGRETVLEYLVSFGVWIRTPPAYRPPNAPILSTLPETTVVN
(SEQ ID NO:4)

Fig. 4

```
ATGGGCAGCAGCCATCATCATCATCATCACAGCAGCGGCCTGGTGCCGCGCGGCAGCCA
TATGGACATTGACCCTTATAAAGAATTTGGAGCTACTGTGGAGTTACTCTCGTTTTTGC
CTTCTGACTTCTTTCCTTCCGTCAGAGATCTCCTAGACACCGCCTCAGCTCTGTATCGG
GAAGCCTTAGAGTCTCCTGAGCATTGCTCACCTCACCACACCGCACTCAGGCAAGCCAT
TCTCTGCTGGGGGGAATTGATGACTCTAGCTACCTGGGTGGGTAATAATTTGGAAGATC
CAGCATCAAGGGATCTAGTAGTCAATTATGTTAATACTAACATGGGTTTAAAATTTAGG
CAACTATTGTGGTTTCATATATCTTGCCTTACTTTTGGAAGAGAGACTGTACTTGAATA
TTTGGTATCTTTCGGAGTGTGGATTCGCACTCCTCCAGCCTATAGACCACCAAATGCCC
CTATCTTATCAACACTTCCGGAAACTACTGTTGTTAGACGACGGGACCGAGGCAGGTCC
CCTAGAAGAAGAACTCCCTCGCCTCGCAGACGCAGATCTCAATCGCCGCGTCGCAGAAG
ATCTCAATCTCGGGAATCTCAATGTGTTAACGCCAAGACAATTGCGTACGACGAAGAGG
CCCGTCGCGGCCTCGAGCGGGGCTTGAACGCCCTCGCCGATGCGGTAAAGGTGACATTG
GGCCCCAAGGGCCGCAACGTCGTCCTGGAAAAGAAGTGGGGTGCCCCCACGATCACCAA
CGATGGTGTGTCCATCGCCAAGGAGATCGAGCTGGAGGATCCGTACGAGAAGATCGGCG
CCGAGCTGGTCAAAGAGGTAGCCAAGAAGACCGATGACGTCGCCGGTGACGGCACCACG
ACGGCCACCGTGCTGGCCCAGGCGTTGGTTCGCGAGGGCCTGCGCAACGTCGCGGCCGG
CGCCAACCCGCTCGGTCTCAAACGCGGCATCGAAAAGGCCGTGGAGAAGGTCACCGAGA
CCCTGCTCAAGGGCGCCAAGGAGGTCGAGACCAAGGAGCAGATTGCGGCCACCGCAGCG
ATTTCGGCGGGTGACCAGTCCATCGGTGACCTGATCGCCGAGGCGATGGACAAGGTGGG
CAACGAGGGCGTCATCACCGTCGAGGAGTCCAACACCTTTGGGCTGCAGCTCGAGCTCA
CCGAGGGTATGCGGTTCGACAAGGGCTACATCTCGGGGTACTTCGTGACCGACCCGGAG
CGTCAGGAGGCGGTCCTGGAGGACCCCTACATCCTGCTGGTCAGCTCCAAGGTGTCCAC
TGTCAAGGATCTGCTGCCGCTGCTCGAGAAGGTCATCGGAGCCGGTAAGCCGCTGCTGA
TCATCGCCGAGGACGTCGAGGGCGAGGCGCTGTCCACCCTGGTCGTCAACAAGATCCGC
GGCACCTTCAAGTCGGTGGCGGTCAAGGCTCCCGGCTTCGGCGACCGCCGCAAGGCGAT
GCTGCAGGATATGGCCATTCTCACCGGTGGTCAGGTGATCAGCGAAGAGGTCGGCCTGA
CGCTGGAGAACGCCGACCTGTCGCTGCTAGGCAAGGCCCGCAAGGTCGTGGTCACCAAG
GACGAGACCACCATCGTCGAGGGCGCCGGTGACACCGACGCCATCGCCGGACGAGTGGC
CCAGATCCGCCAGGAGATCGAGAACAGCGACTCCGACTACGACCGTGAGAAGCTGCAGG
```

Fig. 5 (page 1 of 2)

```
AGCGGCTGGCCAAGCTGGCCGGTGGTGTCGCGGTGATCAAGGCCGGTGCCGCCACCGAG
GTCGAACTCAAGGAGCGCAAGCACCGCATCGAGGATGCGGTTCGCAATGCCAAGGCCGC
CGTCGAGGAGGGCATCGTCGCCGGTGGGGGTGTGACGCTGTTGCAAGCGGCCCCGACCC
TGGACGAGCTGAAGCTCGAAGGCGACGAGGCGACCGGCGCCAACATCGTGAAGGTGGCG
CTGGAGGCCCCGCTGAAGCAGATCGCCTTCAACTCCGGGCTGGAGCCGGGCGTGGTGGC
CGAGAAGGTGCGCAACCTGCCGGCTGGCCACGGACTGAACGCTCAGACCGGTGTCTACG
AGGATCTGCTCGCTGCCGGCGTTGCTGACCCGGTCAAGGTGACCCGTTCGGCGCTGCAG
AATGCGGCGTCCATCGCGGGGCTGTTCCTGACCACCGAGGCCGTCGTTGCCGACAAGCC
GGAAAAGGAGAAGGCTTCCGTTCCCGGTGGCGGCGACATGGGTGGCATGGATTTCTGA
(SEQ ID NO:5)
```

Fig. 5 (page 2 of 2)

MGSSHHHHHHSSGLVPRGSHMDIDPYKEFGATVELLSFLPSDFFPSVRDLLDTASALYR
EALESPEHCSPHHTALRQAILCWGELMTLATWVGNNLEDPASRDLVVNYVNTNMGLKFR
QLLWFHISCLTFGRETVLEYLVSFGVWIRTPPAYRPPNAPILSTLPETTVVRRRDRGRS
PRRRTPSPRRRRSQSPRRRRSQSRESQCVNAKTIAYDEEARRGLERGLNALADAVKVTL
GPKGRNVVLEKKWGAPTITNDGVSIAKEIELEDPYEKIGAELVKEVAKKTDDVAGDGTT
TATVLAQALVREGLRNVAAGANPLGLKRGIEKAVEKVTETLLKGAKEVETKEQIAATAA
ISAGDQSIGDLIAEAMDKVGNEGVITVEESNTFGLQLELTEGMRFDKGYISGYFVTDPE
RQEAVLEDPYILLVSSKVSTVKDLLPLLEKVIGAGKPLLIIAEDVEGEALSTLVVNKIR
GTFKSVAVKAPGFGDRRKAMLQDMAILTGGQVISEEVGLTLENADLSLLGKARKVVVTK
DETTIVEGAGDTDAIAGRVAQIRQEIENSDSDYDREKLQERLAKLAGGVAVIKAGAATE
VELKERKHRIEDAVRNAKAAVEEGIVAGGGVTLLQAAPTLDELKLEGDEATGANIVKVA
LEAPLKQIAFNSGLEPGVVAEKVRNLPAGHGLNAQTGVYEDLLAAGVADPVKVTRSALQ
NAASIAGLFLTTEAVVADKPEKEKASVPGGGDMGGMDF (SEQ ID NO:6)

Fig. 6

```
ATGGGCAGCAGCCATCATCATCATCATCACAGCAGCGGCCTGGTGCCGCGCGGCAGCCATATGGA
CATTGACCCTTATAAAGAATTTGGAGCTACTGTGGAGTTACTCTCGTTTTTGCCTTCTGACTTCT
TTCCTTCCGTCAGAGATCTCCTAGACACCGCCTCAGCTCTGTATCGGGAAGCCTTAGAGTCTCCT
GAGCATTGCTCACCTCACCACACCGCACTCAGGCAAGCCATTCTCTGCTGGGGGGAATTGATGAC
TCTAGCTACCTGGGTGGGTAATAATTTGGAAGATCCAGCATCAAGGGATCTAGTAGTCAGTTATG
TTAATACTAACATGGGTTTAAAATTTAGGCAACTATTGTGGTTTCATATATCTTGCCTTACTTTT
GGAAGAGAGACTGTACTTGAATATTTGGTATCTTTCGGAGTGTGGATTCGCACTCCTCCAGCCTA
TAGACCACCAAATGCCCCTATCTTATCAACACTTCCGGAAACTACTGTTGTTAACGCCAAGACAA
TTGCGTACGACGAAGAGGCCCGTCGCGGCCTCGAGCGGGGCTTGAACGCCCTCGCCGATGCGGTA
AAGGTGACATTGGGCCCCAAGGGCCGCAACGTCGTCCTGGAAAAGAAGTGGGGTGCCCCCACGAT
CACCAACGATGGTGTGTCCATCGCCAAGGAGATCGAGCTGGAGGATCCGTACGAGAAGATCGGCG
CCGAGCTGGTCAAAGAGGTAGCCAAGAAGACCGATGACGTCGCCGGTGACGGCACCACGACGGCC
ACCGTGCTGGCCCAGGCGTTGGTTCGCGAGGGCCTGCGCAACGTCGCGGCCGGCGCCAACCCGCT
CGGTCTCAAACGCGGCATCGAAAAGGCCGTGGAGAAGGTCACCGAGACCCTGCTCAAGGGCGCCA
AGGAGGTCGAGACCAAGGAGCAGATTGCGGCCACCGCAGCGATTTCGGCGGGTGACCAGTCCATC
GGTGACCTGATCGCCGAGGCGATGGACAAGGTGGGCAACGAGGGCGTCATCACCGTCGAGGAGTC
CAACACCTTTGGGCTGCAGCTCGAGCTCACCGAGGGTATGCGGTTCGACAAGGGCTACATCTCGG
GGTACTTCGTGACCGACCCGGAGCGTCAGGAGGCGGTCCTGGAGGACCCCTACATCCTGCTGGTC
AGCTCCAAGGTGTCCACTGTCAAGGATCTGCTGCCGCTGCTCGAGAAGGTCATCGGAGCCGGTAA
GCCGCTGCTGATCATCGCCGAGGACGTCGAGGGCGAGGCGCTGTCCACCCTGGTCGTCAACAAGA
TCCGCGGCACCTTCAAGTCGGTGGCGGTCAAGGCTCCCGGCTTCGGCGACCGCCGCAAGGCGATG
CTGCAGGATATGGCCATTCTCACCGGTGGTCAGGTGATCAGCGAAGAGGTCGGCCTGACGCTGGA
GAACGCCGACCTGTCGCTGCTAGGCAAGGCCCGCAAGGTCGTGGTCACCAAGGACGAGACCACCA
TCGTCGAGGGCGCCGGTGACACCGACGCCATCGCCGGACGAGTGGCCCAGATCCGCCAGGAGATC
GAGAACAGCGACTCCGACTACGACCGTGAGAAGCTGCAGGAGCGGCTGGCCAAGCTGGCCGGTGG
TGTCGCGGTGATCAAGGCCGGTGCCGCCACCGAGGTCGAACTCAAGGAGCGCAAGCACCGCATCG
AGGATGCGGTTCGCAATGCCAAGGCCGCCGTCGAGGAGGGCATCGTCGCCGGTGGGGTGTGACG
CTGTTGCAAGCGGCCCCGACCCTGGACGAGCTGAAGCTCGAAGGCGACGAGGCGACCGGCGCCAA
CATCGTGAAGGTGGCGCTGGAGGCCCCGCTGAAGCAGATCGCCTTCAACTCCGGGCTGGAGCCGG
GCGTGGTGGCCGAGAAGGTGCGCAACCTGCCGGCT
```

Fig. 7 (page 1 of 2)

GGCCACGGACTGAACGCTCAGACCGGTGTCTACGAGGATCTGCTCGCTGCCGGCGTTGCTGACCC
GGTCAAGGTGACCCGTTCGGCGCTGCAGAATGCGGCGTCCATCGCGGGGCTGTTCCTGACCACCG
AGGCCGTCGTTGCCGACAAGCCGGAAAAGGAGAAGGCTTCCGTTCCCGGTGGCGGCGACATGGGT
GGCATGGATTTCTGA (SEQ ID NO:7)

Fig. 7 (page 2 of 2)

```
MGSSHHHHHHSSGLVPRGSHMDIDPYKEFGATVELLSFLPSDFFPSVRDLLDTASALYR
EALESPEHCSPHHTALRQAILCWGELMTLATWVGNNLEDPASRDLVVSYVNTNMGLKFR
QLLWFHISCLTFGRETVLEYLVSFGVWIRTPPAYRPPNAPILSTLPETTVVNAKTIAYD
EEARRGLERGLNALADAVKVTLGPKGRNVVLEKKWGAPTITNDGVSIAKEIELEDPYEK
IGAELVKEVAKKTDDVAGDGTTTATVLAQALVREGLRNVAAGANPLGLKRGIEKAVEKV
TETLLKGAKEVETKEQIAATAAISAGDQSIGDLIAEAMDKVGNEGVITVEESNTFGLQL
ELTEGMRFDKGYISGYFVTDPERQEAVLEDPYILLVSSKVSTVKDLLPLLEKVIGAGKP
LLIIAEDVEGEALSTLVVNKIRGTFKSVAVKAPGFGDRRKAMLQDMAILTGGQVISEEV
GLTLENADLSLLGKARKVVVTKDETTIVEGAGDTDAIAGRVAQIRQEIENSDSDYDREK
LQERLAKLAGGVAVIKAGAATEVELKERKHRIEDAVRNAKAAVEEGIVAGGGVTLLQAA
PTLDELKLEGDEATGANIVKVALEAPLKQIAFNSGLEPGVVAEKVRNLPAGHGLNAQTG
VYEDLLAAGVADPVKVTRSALQNAASIAGLFLTTEAVVADKPEKEKASVPGGGDMGGMD
F
SEQ ID NO:8)
```

Fig. 8

```
ATGGACATTGACCCTTATAAAGAATTTGGAGCTACTGTGGAGTTACTCTCGTTTTTGCCTTCTGA
CTTCTTTCCTTCCGTCAGAGATCTCCTAGACACCGCCTCAGCTCTGTATCGGGAAGCCTTAGAGT
CTCCTGAGCATTGCTCACCTCACCACACCGCACTCAGGCAAGCCATTCTCTGCTGGGGGGAATTG
ATGACTCTAGCTACCTGGGTGGGTAATAATTTGGAAGATCCAGCATCAAGGGATCTAGTAGTCAA
TTATGTTAATACTAACATGGGTTTAAAATTTAGGCAACTATTGTGGTTTCATATATCTTGCCTTA
CTTTTGGAAGAGAGACTGTACTTGAATATTTGGTATCTTTCGGAGTGTGGATTCGCACTCCTCCA
GCCTATAGACCACCAAATGCCCCTATCTTATCAACACTTCCGGAAACTACTGTTGTTAGACGAGC
CAAGACAATTGCGTACGACGAAGAGGCCCGTCGCGGCCTCGAGCGGGGCTTGAACGCCCTCGCCG
ATGCGGTAAAGGTGACATTGGGCCCCAAGGGCCGCAACGTCGTCCTGGAAAAGAAGTGGGGTGCC
CCCACGATCACCAACGATGGTGTGTCCATCGCCAAGGAGATCGAGCTGGAGGATCCGTACGAGAA
GATCGGCGCCGAGCTGGTCAAAGAGGTAGCCAAGAAGACCGATGACGTCGCCGGTGACGGCACCA
CGACGGCCACCGTGCTGGCCCAGGCGTTGGTTCGCGAGGGCCTGCGCAACGTCGCGGCCGGCGCC
AACCCGCTCGGTCTCAAACGCGGCATCGAAAAGGCCGTGGAGAAGGTCACCGAGACCCTGCTCAA
GGGCGCCAAGGAGGTCGAGACCAAGGAGCAGATTGCGGCCACCGCAGCGATTTCGGCGGGTGACC
AGTCCATCGGTGACCTGATCGCCGAGGCGATGGACAAGGTGGGCAACGAGGGCGTCATCACCGTC
GAGGAGTCCAACACCTTTGGGCTGCAGCTCGAGCTCACCGAGGGTATGCGGTTCGACAAGGGCTA
CATCTCGGGGTACTTCGTGACCGACCCGGAGCGTCAGGAGGCGGTCCTGGAGGACCCCTACATCC
TGCTGGTCAGCTCCAAGGTGTCCACTGTCAAGGATCTGCTGCCGCTGCTCGAGAAGGTCATCGGA
GCCGGTAAGCCGCTGCTGATCATCGCCGAGGACGTCGAGGGCGAGGCGCTGTCCACCCTGGTCGT
CAACAAGATCCGCGGCACCTTCAAGTCGGTGGCGGTCAAGGCTCCCGGCTTCGGCGACCGCCGCA
AGGCGATGCTGCAGGATATGGCCATTCTCACCGGTGGTCAGGTGATCAGCGAAGAGGTCGGCCTG
ACGCTGGAGAACGCCGACCTGTCGCTGCTAGGCAAGGCCCGCAAGGTCGTGGTCACCAAGGACGA
GACCACCATCGTCGAGGGCGCCGGTGACACCGACGCCATCGCCGGACGAGTGGCCCAGATCCGCC
AGGAGATCGAGAACAGCGACTCCGACTACGACCGTGAGAAGCTGCAGGAGCGGCTGGCCAAGCTG
GCCGGTGGTGTCGCGGTGATCAAGGCCGGTGCCGCCACCGAGGTCGAACTCAAGGAGCGCAAGCA
CCGCATCGAGGATGCGGTTCGCAATGCCAAGGCCGCCGTCGAGGAGGGCATCGTCGCCGGTGGGG
GTGTGACGCTGTTGCAAGCGGCCCCGACCCTGGACGAGCTGAAGCTCGAAGGCGACGAGGCGACC
GGCGCCAACATCGTGAAGGTGGCGCTGGAGGCCCCGCTGAAGCAGATCGCCTTCAACTCCGGGCT
GGAGCCGGGCGTGGTGGCCGAGAAGGTGCGCAACCTGCCGGCTGGCCACGGACTGAACGCTCAGA
CCGGTGTCTACGAGGATCTGCTCGCTGCCGGCGTTGCTGACCCGGTCAAGGTGACCCGTTCGGCG
CTGCAGAATGCGGCGTCCATCGCGGGGCTGTTCCTGACCACCGAGGCCGTCGTTGCCGACAAGCC
GGAAAAGGAGAAGGCTTCCGTTCCCGGTGGCGGCGACATGGGTGGCATGGATTTCTGA   SEQID
                                                             NO:9)
```

Fig. 9

```
MDIDPYKEFGATVELLSFLPSDFFPSVRDLLDTASALYREALESPEHCSPHHTALRQAI
LCWGELMTLATWVGNNLEDPASRDLVVNYVNTNMGLKFRQLLWFHISCLTFGRETVLEY
LVSFGVWIRTPPAYRPPNAPILSTLPETTVVRRAKTIAYDEEARRGLERGLNALADAVK
VTLGPKGRNVVLEKKWGAPTITNDGVSIAKEIELEDPYEKIGAELVKEVAKKTDDVAGD
GTTTATVLAQALVREGLRNVAAGANPLGLKRGIEKAVEKVTETLLKGAKEVETKEQIAA
TAAISAGDQSIGDLIAEAMDKVGNEGVITVEESNTFGLQLELTEGMRFDKGYISGYFVT
DPERQEAVLEDPYILLVSSKVSTVKDLLPLLEKVIGAGKPLLIIAEDVEGEALSTLVVN
KIRGTFKSVAVKAPGFGDRRKAMLQDMAILTGGQVISEEVGLTLENADLSLLGKARKVV
VTKDETTIVEGAGDTDAIAGRVAQIRQEIENSDSDYDREKLQERLAKLAGGVAVIKAGA
ATEVELKERKHRIEDAVRNAKAAVEEGIVAGGGVTLLQAAPTLDELKLEGDEATGANIV
KVALEAPLKQIAFNSGLEPGVVAEKVRNLPAGHGLNAQTGVYEDLLAAGVADPVKVTRS
ALQNAASIAGLFLTTEAVVADKPEKEKASVPGGGDMGGMDF (SEQ ID NO:10)
```

Fig. 10

```
ATGGACATTGACCCTTATAAAGAATTTGGAGCTACTGTGGAGTTACTCTCGTTTTTGCCTTCTGA
CTTCTTTCCTTCCGTCAGAGATCTCCTAGACACCGCCTCAGCTCTGTATCGGGAAGCCTTAGAGT
CTCCTGAGCATTGCTCACCTCACCACACCGCACTCAGGCAAGCCATTCTCTGCTGGGGGGAATTG
ATGACTCTAGCTACCTGGGTGGGTAATAATTTGGAAGATCCAGCATCAAGGGATCTAGTAGTCAA
TTATGTTAATACTAACATGGGTTTAAAATTTAGGCAACTATTGTGGTTTCATATATCTTGCCTTA
CTTTTGGAAGAGAGACTGTACTTGAATATTTGGTATCTTTCGGAGTGTGGATTCGCACTCCTCCA
GCCTATAGACCACCAAATGCCCCTATCTTATCAACACTTCCGGAAACTACTGTTGTTAGACGACG
GGACCGAGGCAGGTCCCCTAGAAGAAGAACTCCCTCGCCTCGCAGACGCAGATCTCAATCGCCGC
GTCGCAGAAGATCTCAATCTCGGGAATCTCAATGTGCCAAGACAATTGCGTACGACGAAGAGGCC
CGTCGCGGCCTCGAGCGGGGCTTGAACGCCCTCGCCGATGCGGTAAAGGTGACATTGGGCCCCAA
GGGCCGCAACGTCGTCCTGGAAAAGAAGTGGGGTGCCCCCACGATCACCAACGATGGTGTGTCCA
TCGCCAAGGAGATCGAGCTGGAGGATCCGTACGAGAAGATCGGCGCCGAGCTGGTCAAAGAGGTA
GCCAAGAAGACCGATGACGTCGCCGGTGACGGCACCACGACGGCCACCGTGCTGGCCCAGGCGTT
GGTTCGCGAGGGCCTGCGCAACGTCGCGGCCGGCGCCAACCCGCTCGGTCTCAAACGCGGCATCG
AAAAGGCCGTGGAGAAGGTCACCGAGACCCTGCTCAAGGGCGCCAAGGAGGTCGAGACCAAGGAG
CAGATTGCGGCCACCGCAGCGATTTCGGCGGGTGACCAGTCCATCGGTGACCTGATCGCCGAGGC
GATGGACAAGGTGGGCAACGAGGGCGTCATCACCGTCGAGGAGTCCAACACCTTTGGGCTGCAGC
TCGAGCTCACCGAGGGTATGCGGTTCGACAAGGGCTACATCTCGGGGTACTTCGTGACCGACCCG
GAGCGTCAGGAGGCGGTCCTGGAGGACCCCTACATCCTGCTGGTCAGCTCCAAGGTGTCCACTGT
CAAGGATCTGCTGCCGCTGCTCGAGAAGGTCATCGGAGCCGGTAAGCCGCTGCTGATCATCGCCG
AGGACGTCGAGGGCGAGGCGCTGTCCACCCTGGTCGTCAACAAGATCCGCGGCACCTTCAAGTCG
GTGGCGGTCAAGGCTCCCGGCTTCGGCGACCGCCGCAAGGCGATGCTGCAGGATATGGCCATTCT
CACCGGTGGTCAGGTGATCAGCGAAGAGGTCGGCCTGACGCTGGAGAACGCCGACCTGTCGCTGC
TAGGCAAGGCCCGCAAGGTCGTGGTCACCAAGGACGAGACCACCATCGTCGAGGGCGCCGGTGAC
ACCGACGCCATCGCCGGACGAGTGGCCCAGATCCGCCAGGAGATCGAGAACAGCGACTCCGACTA
CGACCGTGAGAAGCTGCAGGAGCGGCTGGCCAAGCTGGCCGGTGGTGTCGCGGTGATCAAGGCCG
GTGCCGCCACCGAGGTCGAACTCAAGGAGCGCAAGCACCGCATCGAGGATGCGGTTCGCAATGCC
AAGGCCGCCGTCGAGGAGGGCATCGTCGCCGGTGGGGGTGTGACGCTGTTGCAAGCGGCCCCGAC
CCTGGACGAGCTGAAGCTCGAAGGCGACGAGGCGACCGGCGCCAACATCGTGAAGGTGGCGCTGG
AGGCCCCGCTGAAGCAGATCGCCTTCAACTCCGGGCTGGAGCCGGGCGTGGTGGCCGAGAAGGTG
CGCAACCTGCCGGCTGGCCACGGACTGAAC
```

Fig. 11 (page 1 of 2)

GCTCAGACCGGTGTCTACGAGGATCTGCTCGCTGCCGGCGTTGCTGACCCGGTCAAGGTGACCCG
TTCGGCGCTGCAGAATGCGGCGTCCATCGCGGGGCTGTTCCTGACCACCGAGGCCGTCGTTGCCG
ACAAGCCGGAAAAGGAGAAGGCTTCCGTTCCCGGTGGCGGCGACATGGGTGGCATGGATTTCTGA
(SEQ ID NO:11)

Fig. 11 (page 2 of 2)

MDIDPYKEFGATVELLSFLPSDFFPSVRDLLDTASALYREALESPEHCSPHHTALRQAI
LCWGELMTLATWVGNNLEDPASRDLVVNYVNTNMGLKFRQLLWFHISCLTFGRETVLEY
LVSFGVWIRTPPAYRPPNAPILSTLPETTVVRRRDRGRSPRRRTPSPRRRRSQSPRRRR
SQSRESQCAKTIAYDEEARRGLERGLNALADAVKVTLGPKGRNVVLEKKWGAPTITNDG
VSIAKEIELEDPYEKIGAELVKEVAKKTDDVAGDGTTTATVLAQALVREGLRNVAAGAN
PLGLKRGIEKAVEKVTETLLKGAKEVETKEQIAATAAISAGDQSIGDLIAEAMDKVGNE
GVITVEESNTFGLQLELTEGMRFDKGYISGYFVTDPERQEAVLEDPYILLVSSKVSTVK
DLLPLLEKVIGAGKPLLIIAEDVEGEALSTLVVNKIRGTFKSVAVKAPGFGDRRKAMLQ
DMAILTGGQVISEEVGLTLENADLSLLGKARKVVVTKDETTIVEGAGDTDAIAGRVAQI
RQEIENSDSDYDREKLQERLAKLAGGVAVIKAGAATEVELKERKHRIEDAVRNAKAAVE
EGIVAGGGVTLLQAAPTLDELKLEGDEATGANIVKVALEAPLKQIAFNSGLEPGVVAEK
VRNLPAGHGLNAQTGVYEDLLAAGVADPVKVTRSALQNAASIAGLFLTTEAVVADKPEK
EKASVPGGGDMGGMDF (SEQ ID NO:12)

Fig. 12

HEPATITIS B VIRUS TREATMENT

The present application claims the benefit of the filing date of U.S. Ser. No. 60/266,733 (Feb. 5, 2001). The contents of U.S. Ser. No. 60/266,733 are incorporated by reference in the present application in their entirety.

FIELD OF THE INVENTION

The field of the invention is hepatitis B virus immunotherapeutics.

BACKGROUND OF THE INVENTION

Hepatitis B Virus (HBV) is a non-cytopathic DNA virus that infects humans and may result in two clinical outcomes. In the majority of clinical infections in adults (90–95%), the virus is cleared after several weeks or months, and the patient develops a lifelong immunity against re-infection. In the remaining cases, however, the virus is not eliminated from the tissues, and the patient remains chronically infected. The sequence of chronic infection are serious: such individuals are highly likely to develop scarring of the liver tissue (cirrhosis) and may eventually develop hepatocellular carcinoma.

There is a prophylactic vaccine against HBV, and many developed countries have implemented childhood vaccination programs to reduce the overall risk of infection. Unfortunately, since the morbidity and mortality resulting from chronic HBV infection occurs over a period of decades, the impact of vaccination will not be realized until well into the future. Indeed, the annual incidence of HBV infection in adults is expected to decline by less than 5% over the next eight years. By 2008, over 150,000 new infections will occur annually in the United States alone and even more are expected in Europe and Japan. These individuals will constitute a tremendous reservoir of virus, from which as many as 20,000 to 40,000 chronic infections will arise per year. Clearly, despite the availability of a vaccine, chronic HBV infection will continue to be a serious health problem for many years to come.

Current therapies for chronic HBV include alpha interferon (IFN-α) and lamivudine. These therapies are judged by their abilities to reduce viral load and bring about seroconversion or the loss of the HBe antigen, a marker of HBV replication and high-titre viremia. IFN-α can eliminate HBe, but only in about one third of patients, those with low viral burdens. This treatment is costly and is associated with significant unpleasant side effects. Lamivudine is a small molecule anti-viral agent that is very well tolerated when administered orally. This compound is effective in reducing viral load in patients, but relatively few patients respond with loss of HBe, and discontinuation of therapy usually leads to increase in viral load. On the other hand, continued therapy can lead to selection for lamivudine resistant mutant variants. Combination therapy with IFN-α and lamivudine has not shown enhanced efficacy. Clearly, a successful immunotherapy to treat HBV infection is highly desirable.

SUMMARY OF THE INVENTION

The present invention features compositions that include a stress protein, or a portion thereof, and an HBV antigen. These compositions are discussed at length below. We note here that their components can be obtained from a variety of sources and their length and content can vary. For example, the stress protein can be one that is naturally expressed by any mammal (e.g. a human or non-human primate) or any other class of organisms that expresses stress proteins (e.g., a bacterium or mycobacterium); the stress protein and/or the HBV antigen can be full length, truncated, or extended by the addition of one or more amino acid residues; and, in addition, the content of the stress protein or HBV antigen can vary (for example, a stress protein, or a portion thereof, and an HBV antigen can contain one or more amino acid substitutions). Any variation must still result, however, in a composition that can induce or enhance an immune response against HBV in a mammal. Preferably, the immune response is substantial enough that an HBV-infected patient experiences an improvement (objective or subjective) in a sign or symptom of the infection. Accordingly, an antigen encompasses full-length and naturally occurring antigens as well as fragments and other variants thereof that, when administered to a subject (e.g., by the methods described herein), elicits an immune response to one or more epitopes present within the fragment or variant.

Similarly, in addition to full-length or naturally occurring stress proteins, the compositions of the invention can include fragments of stress proteins that are immunostimulatory (i.e., fragments that facilitate an immune response to an antigen). The stress protein, or the fragment thereof, facilitates an immune response when the immune response is greater, or in any way superior to, the immune response that typically occurs when the HBV antigen is administered alone.

The immune response can be either a humoral or a cell-mediated response. For example, an antigenic fragment can contain one or more HLA class I peptide antigens, as described herein. A cell-mediated immune response involves antigen specific cells of the immune system, such as cytotoxic T lymphocytes (CTLs) as well as, possibly, T helper lymphocytes (Th) and cells of the innate immune system, such as monocytes, macrophages, dendritic cells, natural killer cells and γδ T cells. One of ordinary skill in the art is well able to detect or otherwise evaluate an immune response, which is evident by, for example, the induction of cytotoxic T lymphocytes (see the Examples below), a cellular proliferative response, induction of cytokines, or a combination of these events.

In particular embodiments, the HBV antigen can be the HBV core antigen or a fragment or derivative thereof. Derivatives of the HBV antigen include variants of the HBV antigen, such as those containing one or more amino acid substitutions (e.g., conservative amino acid substitutions). For example, a variant of an HBV antigen can contain 1–2, 2–5, 5–10, 10–25, or more, substituted amino acid residues. Alternatively, substitutions or other mutations, such as deletions or truncations, can constitute 1–2, 2–5, 5–10, or 10–25% of the sequence of a full-length HBV antigen. Like the antigenic portion of the composition, a variant of a stress protein can contain one or more amino acid substitutions (e.g., conservative amino acid substitutions). For example, a variant of a stress protein can contain 1–2, 2–5, 5–10, 10–25, or more, conservative amino acid substitutions. Here again, substitutions or other mutations, such as deletions or truncations, can constitute 1–2, 2–5, 5–10, or 10–25% of the sequence of a full-length stress protein.

Various combinations of stress proteins and HBV antigens are also within the scope of the invention. For example, the compositions of the invention include those in which a full-length HBV antigen is associated with a full-length stress protein; an antigen that consists of a fragment or other variant of an HBV antigen is associated with a full-length stress protein; a full-length HBV antigen is associated with a fragment or other variant of a stress protein; and a fragment or other variant of an HBV antigen is associated with a fragment or other variant of a stress protein. Of course, as described herein, more than one of each of these components (i.e., more than one HBV antigen and more than one stress protein) may be present, and each of the components may be present in the form of a full-length protein or an immunologically active fragment or variant thereof.

Moreover, in any of the arrangements described herein, the HBV antigen and the stress protein can be associated in any manner. For example, the stress protein and the HBV antigen, can be present in the form of a fusion polypeptide (wherein the stress protein and the HBV antigen are covalently linked during translation of a fused open reading frame). Alternatively, a stress protein and an HBV antigen can be linked by chemical conjugation after each has been translated or synthesized individually. The components can also be non-covalently associated (in, for example, a mixture or a more ordered composition). The terms "polypeptide" and "protein" are used interchangeably to describe a chain of amino acid residues, except where it is clear from the context that a distinct meaning is intended.

While stress proteins are discussed further below, we note here that the stress protein can be a heat shock protein (Hsp). Further, the Hsp can be a mycobacterial Hsp, such as Hsp65 (e.g., Hsp65 of *Mycobacterium bovis*), or any member of an Hsp family of proteins from any species.

The compositions of the invention can be formulated for administration to a subject in a variety of ways and, optionally, contain an adjuvant. Additional optional components of the composition include pharmaceutically acceptable diluents, excipients, and carriers.

The invention also features methods of treating an HBV infection in a subject (e.g., a mammal, such as a human) by administering a composition of the invention to the subject infected with HBV and methods of preventing (or reducing the likelihood of) an HBV infection in a subject (e.g., a mammal, such as a human) by administering a composition of the invention to the subject before they have been infected with HBV.

The components of the composition need not be directly administered to the subject as polypeptides. Instead, a nucleic acid encoding the stress protein, the HBV antigen, or a fusion protein containing one or more of each can be administered, and the protein, antigen, or fusion protein will be expressed in the subject in vivo. The nucleic acid can be a part of a viral vector, for example, a part of a viral vector genome, or encapsulated in, e.g., liposomes. Alternatively, the nucleic acid can be delivered as a naked nucleic acid, such as plasmid DNA driven by regulatory sequences operable in eukaryotic or mammalian cells. Methods of administering nucleic acid molecules are well known in the art.

The invention further includes the use of compositions of the invention (e.g., HBV-containing fusion proteins, the nucleic acid molecules that encode them, and pharmaceutical compositions containing them) in the manufacture of a medicament for the treatment of hepatitis B virus infection in accordance with the methods described herein.

Other features or advantages of the present invention will be apparent from the detailed description, the drawings, and the claims. All patent applications, patents, and publications cited herein are incorporated by reference in their entirety.

BRIEF DESCRIPTION OF THE DRAWINGS

FIG. 1 is a DNA sequence encoding HBV (subtype adw) core antigen (HBc) (SEQ ID NO:1).

FIG. 2 is the amino acid sequence of HBV (subtype adw) core antigen (SEQ ID NO:2).

FIG. 3 is the DNA sequence of construct hisHepCorT (149/87S97F), which encodes a histidine-tagged, truncated HBV core antigen (amino acids 1–149; SEQ ID NO:3).

FIG. 4 is the amino acid sequence encoded by the DNA sequence of FIG. 3 (SEQ ID NO:4).

FIG. 5 is the DNA sequence of construct hisHepCor(97F) Hsp65, which encodes a histidine-tagged fusion protein that includes a full length HBV core antigen and an Hsp65 protein (SEQ ID NO:5).

FIG. 6 is the amino acid sequence encoded by the DNA sequence of FIG. 5 (SEQ ID NO:6).

FIG. 7 is the DNA sequence of construct hisHepCorT (149/87S97F)Hsp65, which encodes a histidine-tagged fusion protein that includes a truncated (amino acids 1–149) HBV core antigen fused to the Hsp65 protein (SEQ ID NO:7).

FIG. 8 is the amino acid sequence encoded by the DNA sequence of FIG. 7 (SEQ ID NO:8).

FIG. 9 is the DNA sequence of construct HepCorT(151/97F)Hsp65, which encodes a fusion protein that includes a truncated (amino acids 1–151) HBV core antigen fused to the Hsp65 protein (SEQ ID NO:9).

FIG. 10 is the amino acid sequence encoded by the DNA sequence of FIG. 9 (SEQ ID NO:10).

FIG. 11 is the DNA sequence of construct HepCor(97F) Hsp65, which encodes a fusion protein that includes the full length HBV core antigen fused to the Hsp65 protein (SEQ ID NO:11).

FIG. 12 is the amino acid sequence encoded by the DNA sequence of FIG. 11 (SEQ ID NO:12).

FIG. 13 is a graph depicting the CTL priming activity (% corrected lysis v. effector:target ratio) in C57BL/6 mice immunized with various immunogens (HepCorT(151/97F) Hsp65; HepCor(97F)Hsp65; HepCorT (151/97F); HepCor (97F); and hisHepCorT(149/87S97F)Hsp65). The resulting CTL lytic activity was assayed against EL4 cells pre-pulsed with a control peptide, MUT-1.52–59.Kb. Control mice were injected with placebo (buffer).

FIG. 14 is a graph depicting the CTL priming activity (% corrected lysis v. effector:target ratio) in C57BL/6 mice immunized with various immunogens (as in FIG. 13). The resulting CTL lytic activity was assayed against EL4 cells pre-pulsed with the HBc antigen-specific peptide, HBc.93–100.Kb. Control mice were injected with placebo (buffer).

FIG. 15 is a graph depicting the CTL priming activity (% corrected lysis v. effector:target ratio) in C57BL/6 mice immunized with various immunogens (as in FIG. 13). The resulting CTL lytic activity was assayed against EL4.HBc. 1D7 cells, which express hepatitis B core antigen. Control mice were injected with placebo (buffer).

FIG. 16 is a graph depicting the CTL priming activity (IFN-γ (pg/ml) v. effector:target ratio) in C57BL/6 mice immunized with various immunogens (as in FIG. 13). The ability of resultant CTLs to secrete gamma interferon (IFN-γ) was assayed against EL4 cells co-cultured with the HBc antigen-specific peptide, HBc.93–100.Kb. Control mice were injected with placebo (buffer).

FIG. 17 is a graph depicting the CTL priming activity (TNF-α ($OD_{410}$) in C57BL/6 mice immunized with various immunogens (as in FIG. 13). The ability of generated CTLs to secrete tumor necrosis factor alpha (TNF-α) was assayed against EL4 cells co-cultured with the HBc antigen-specific peptide, HBc.93–100.Kb. Control mice were injected with placebo (buffer).

DETAILED DESCRIPTION

The invention relates to HBV antigen-containing compositions that are useful in treating or preventing HBV infection. The content of the compositions can vary, as described herein, but the compositions comprise a stress protein, or a portion (e.g., a fragment) or derivative thereof, and an HBV antigen. Various materials and procedures suitable for use in the methods of the invention are discussed below.

Because nucleic acid sequences encoding stress proteins and HBV proteins are known and available, nucleic acid constructs encoding them (alone or as a fusion construct) can be readily prepared using methods routinely practiced in the art. For examples of nucleic acids encoding a stress protein (an Hsp) optionally coupled to an antigen see WO 89/12455, WO 94/29459, WO 98/23735, WO 99/07860, and references cited therein. Fusion proteins can be produced not only by recombinant techniques but also by post-translational conjugation of a stress protein (e.g., an Hsp) and an HBV antigen. Conjugation techniques are described, for example, in Hermanson (*Bioconjugate Techniques*, Academic Press, San Diego, Calif., 1996) Lussow et al. (*Eur. J. Immun.* 21:2297–2302, 1991), and Barrios et al. (*Eur. J. Immun.* 22:1365–1372, 1992). Such methods of conjugation include the use of coupling agents such as glutaraldehyde, carbodiimides, and bisdiazobenzidine; the use of heterobifunctional crosslinkers such as M-Maleimidobenzoyl-N-hydroxysuccinimide ester; or the use of cysteine residues (those naturally present and/or those recombinantly inserted) in the stress protein and the antigen to facilitate intermolecular disulfide bond formation.

Any HBV antigen is suitable for inclusion in a fusion protein or composition of the invention. A preferred HBV antigen is the HBV core antigen or a fragment or derivative thereof. To facilitate testing, the HBV antigen can optionally be modified to include known mouse MHC-restricted CTL epitopes such as, for example, mouse H-2K$^b$-restricted CTL epitopes. An example of such a modification is described in the Examples (for example, in the adw strain of HBV, residue 97 is isoleucine—replacing this with phenylalanine generates a mouse H-2K$^b$-restricted CTL epitope). In addition, the antigen can be modified to include human HLA epitopes from more than one HBV subtype (e.g. adw, ayw, adr or ayr). For example, a single amino acid substitution from a threonine to a valine at position 91 of the HBV core antigen shown in FIG. 2 would duplicate the sequence of a known HLA-A11-restricted CTL epitope found in both the adw and adr HBV subtypes. Other derivatives of the HBV core antigen include truncations. Such truncations would include, but are not limited to, truncations in which all or part of the C-terminal arginine-rich domain is removed (amino acids 150 to 185 of HBc). Suitable truncated HBc fragments include, but are not limited to, fragments consisting of only the first N-terminal 149 amino acids, or the first 151 N-terminal amino acids of HBc. In any event, a suitable fragment of the HBc antigen (or any suitable HBV antigen) would ideally include one or more B or T cell epitopes (or one or more B cell epitopes and one or more T cell epitopes), preferably one or more CTL epitopes. Additionally, the terminal cysteine of the HBV core antigen can be removed or replaced with a different amino acid. Other modifications to the amino acid sequence could be made. Another example is a substitution in an anchor residue of a known HLA-restricted CTL epitope to enhance the binding affinity of the peptide to the MHC Class I molecule. Although these modified HBV core antigens are suitable for inclusion in bile fusion proteins, they can also be used alone (optionally formulated with an adjuvant) to generate an immune response to HBV.

Additional HBV antigens suitable for use in the present invention include the HBV core antigen, HBV e antigen (HBeAg), x protein (HBx), polymerase polypeptide, and the HBV envelope proteins S, M, and L and fragments thereof (Seeger and Mason, *Microbiol. Mol. Biol. Rev.* 64: 51–68, 2000; Ganem and Schneider, *Hepadnavirdae: The viruses and their replication.* In: Knipe, D M and Howley, P M, eds. *Fields Virology*, Philadelphia: Lippincott Williams & Wilkins, 2001:2923–2969).

As described above, the HBV antigen, the stress protein, or both, can contain one or more amino acid substitutions (e.g., conservative amino acid substitutions). These substitutions can be, but are not necessarily, made at one or more predicted non-essential amino acid residues. A "conservative amino acid substitution" is one in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Regardless of whether the substitution is designed to occur at a predicted non-essential site or is introduced randomly along all or part of an HBV antigen or stress protein coding sequence (such as by saturation mutagenesis), the resultant mutants can be screened for antigenic and inmunostimulatory activity, respectively, to identify mutants that retain biological activity. Following mutagenesis, the encoded protein can be expressed recombinantly and the activity of the protein can be determined.

The HBV antigen can be fused to either the N-terminus or C-terminus of the stress protein, with or without a linker or intervening exogenous sequence. In alternative embodiments, two HBV antigens (which can be naturally occurring or variant, as described herein) can be attached to the stress protein (one at the N-terminus and the other at the C-terminus of the stress protein; both at the N-terminus; or both at the C-terminus). Additionally, one or more HBV antigens (again, naturally occurring or fragments or other variants thereof; from either the same or different HBV proteins) can be attached either to the N-terminus or C-terminus, or both, of the stress protein. Additional alternative arrangements can be made, and will be evident to one of ordinary skill in the art, if more than one stress protein is included.

A stress protein and an HBV antigen (or combinations thereof; for example a stress protein and two or more HBV antigens) can be linked by chemical conjugation after each has been translated or synthesized individually. As noted above, the components can also be non-covalently associated (in, for example, a mixture or a more ordered composition). Compositions containing stress proteins or immunostimulatory fragments thereof that are non-covalently associated with an HPV antigen can be produced as described in U.S. Pat. Nos. 6,048,530; 6,017,544; 6,017,540; 6,007,821; 5,985,270; 5,948,646; 5,935,576; 5,837,251; 5,830,464; or 5,750,119. See also, U.S. Pat. Nos. 5,997,873; 5,961,979; 6,030,618; 6,139,841; 6,156,302; 6,168,793; and International Publication No. WO 97/06821.

Moreover, more than one type of viral antigen can be included in the composition. For example, in addition to the HBV antigen, compositions of the invention can include (or encode; any proteins described herein may be administered directly or by way of nucleic acids) an antigen from a different pathogen. Thus, in addition to an HBV antigen, the compositions can include (or encode) a hepatitis C antigen, a herpes simplex virus (HSV) antigen, a human immunodeficiency virus (HIV) antigen, a cytomegalovirus (CMV) antigen, an Epstein-Barr virus (EBV) antigen, a respiratory syncytial virus (RSV) antigen, a human papillomavirus (HPV) antigen, a herpes virus antigen, or a combination thereof. The same alternatives that have been described for the embodiments in which the compositions contain only HBV as the viral antigen (e.g., the method of association with the stress protein, the inclusion of full-length, fragmented, or variant proteins, the variable number of components, and their arrangement) are applicable to the embodiments in which at least one HBV antigen and at least one other viral antigen are present in (or encoded by) the composition.

Surprisingly, it has also been found that removing the C-terminal arginine-rich domain from the core antigen results in a polypeptide capable of eliciting an immune response to the core antigen, particularly a cellular and/or a CTL immune response. The arginine-rich domain of the core antigen is located between amino acids 150 to 183 of the core antigen (Nassal, *J. Virol.* 66: 4107–4116, 1992). Suitable core antigen fragments include, but are not limited to, those that lack all or part of this region. For example, suitable core antigen fragments may contain of the first 149 or 151 amino acids (or fewer than 149 or 151 amino acids).

The compositions of the invention can optionally include an adjuvant. Examples of adjuvants that may be effective include, but are not limited to: Freund's complete adjuvant (FCA), Freund's incomplete adjuvant (FIA), SAF, muramyl dipeptide (MDP), lipopolysaccharide (LPS), lipid A, monophosphoryl lipid A (MPL), pertusis toxin (PT), stearyl tyrosine, γ inulin, RIBI (which contains three components extracted from bacteria), Quil-A, saponins (QS21), alum (aluminum hydroxide, aluminum phosphate), calcium phosphate, MF-59, immunostimulatory complexes (ISCOMS), CpG oligonucleotides and cytokines (Gupta and Siber, *Vaccine* 13: 1263–1276, 1995; Singh and O'Hagan, *Nature Biotechnology* 17: 1075–1081, 1999).

A suitable fragment or derivative of an HBV antigen will ideally contain at least one B or T cell epitope (or both). In a preferred embodiment, the fragment or derivative will contain at least one CTL epitope.

A variety of stress proteins have been isolated, cloned, and characterized from a diverse array of organisms (Mizzen, *Biotherapy* 10:173–189, 1998). Any immunostimulatory Hsp or immunostimulatory fragment thereof is suitable for use in the fusion polypeptides and compositions. For example, Hsp70, Hsp60, Hsp20–30 (low molecular weight Hsp), and Hsp10 (the GroES homologue) are among the major determinants recognized by host immune responses to infection by *Mycobacterium tuberculosis* and *Mycobacterium leprae*. In addition, Hsp65 of Bacille Calmette Guerin (BCG), a strain of *Mycobacterium bovis*, was found to be an effective immunostimulatory agent, as described in the example below.

Families of stress genes and proteins for use in the present invention are well known in the art and include, for example, Hsp100–200, Hsp100, Hsp90, Lon, Hsp70, Hsp60, TF55, Hsp40, FKBPs, cyclophilins, Hsp20–30, ClpP, GrpE, Hsp10, ubiquitin, calnexin, and protein disulfide isomerases. See, e.g., Macario, Cold Spring Harbor Laboratory Res. 25:59–70, 1995; Parsell et al., *Rev. Genet.* 27:437–496, 1993; and U.S. Pat. No. 5,232,833.

Examples of Hsp100–200 proteins include Grp170 (for glucose-regulated protein). Grp170 resides in the lumen of the ER and in the pre-Golgi compartment, and may play a role in immunoglobulin folding and assembly.

Examples of Hsp100 proteins include mammalian Hsp110, yeast Hsp104, and *E. coli* ClpA, ClpB, ClpC, ClpX agnd ClpY.

Examples of Hsp90 proteins include HtpG in *E. coli*, Hsp83 and Hsc83 in yeast, and Hsp90alpha, Hsp90beta, and Grp94 (small gp96) in humans. Hsp90 binds groups of proteins that are typically cellular regulatory molecules, such as steroid hormone receptors (e.g., glucocorticoid, estrogen, progesterone, and testosterone receptors), transcription factors, and protein kinases that play a role in signal transduction mechanisms. Hsp90 proteins also participate in the formation of large, abundant protein complexes that include other stress proteins.

Lon is a tetrameric ATP-dependent protease that degrades non-native proteins in *E. coli*.

Examples of Hsp70 proteins include Hsp72 and Hsc73 from mammalian cells, DnaK from bacteria or mycobacteria such as *Mycobacterium leprae*, *Mycobacterium tuberculosis*, and *Mycobacterium bovis* (such as Bacille-Calmette Guerin; referred to herein as Hsp71), DnaK from *E. coli*, yeast, and other prokaryotes, and BiP and Grp78. Hsp70 is capable of specifically binding ATP as well as unfolded polypeptides and peptides, and participates in protein folding and unfolding as well as in the assembly and disassembly of protein complexes.

Examples of Hsp60 proteins include Hsp65 from mycobacteria. Bacterial Hsp60 is also commonly known as GroEL. Hsp60 forms large homooligomeric complexes, and appears to play a key role in protein folding. Hsp60 homologues are present in eukaryotic mitochondria and chloroplasts.

Examples of TF55 proteins include Tcp1, TRiC, and thermosome. The proteins typically occur in the cytoplasm of eukaryotes and some archaebacteria, and form multimembered rings, promoting protein folding. They are also weakly homologous to Hsp60.

Examples of Hsp40 proteins include DnaJ from prokaryotes such as *E. coli* and mycobacteria and HSJ1, HDJ1, and Hsp40. Hsp40 plays a role as a molecular chaperone in protein folding, thermotolerance and DNA replication, among other cellular activities.

FKBP examples include FKBP12, FKBP13, FKBP25, and FKBP59, Fprl and Nepl. The proteins typically have peptidyl-prolyl isomerase activity and interact with immunosuppressants such as FK506 and rapamycin. The proteins are typically found in the cytoplasm and the endoplasmic reticulum.

Cyclophilin examples include cyclophilins A, B, and C. The proteins have peptidyl-prolyl isomerase activity and interact with the immunosuppressant cyclosporin A.

Hsp20–30 is also referred to as small Hsp. Hsp20–30 is typically found in large homooligomeric complexes or possibly heterooligomeric complexes. An organism or cell type can express several different types of small Hsps. Hsp20–30 interacts with cytoskeletal structures and may play a regulatory role in the polymerization/depoly-merization of actin. Hsp20–30 is rapidly phosphorylated upon stress or exposure of resting cells to growth factors. Hsp20–30 homologues include alpha-crystallin.

ClpP is an *E. coli* protease involved in degradation of abnormal proteins. Homologues of ClpP are found in chloroplasts. ClpP forms a heterooligomeric complex with ClpA.

GrpE is an *E. coli* protein of about 20 kDa that is involved in the rescue of stress-damaged proteins as well as the degradation of damaged proteins. GrpE plays a role in the regulation of stress gene expression in *E. coli*.

Hsp10 examples include GroES and Cpn10. Hsp10 is found in *E. coli* and in the mitochondria and chloroplasts of eukaryotic cells. Hsp10 forms a seven-membered ring that associates with Hsp60 oligomers. Hsp10 is also involved in protein folding.

Ubiquitin has been found to bind proteins in coordination with the proteolytic removal of the proteins by ATP-dependent cytosolic proteases.

In addition to full-length stress proteins, any immunostimulatory fragments or derivatives would be useful in the present invention. An immunostimulatory fragment or derivative (e.g., an immunostimulatory fragment of an Hsp) is a fragment or derivative that facilitates an immune response to an antigen. The fragment or derivative can facilitate an immune response in a number of ways. For example, the fragment can induce an immune response that would not otherwise occur or enhance an immune response that would. A number of immunostimulatory fragments have been described. Suitable fragments include, but are not limited to fragments comprising: (a) amino acids 161–370 of mycobacterial Hsp70 (particularly *M. tuberculosis* Hsp70) (Huang et al., *J. Exp. Med.* 191:403–408; 2000, U.S. patent application Ser. No. 09/761,534 filed Jan. 16, 2001); (b) the ATPase domain or peptide binding domain of mycobacterial Hsp70 (particularly *M. tuberculosis* Hsp70) (Young, U.S. Ser. No. 09/025,178 filed Nov. 25, 1997); (c) amino acids 280–385 of murine Hsc70 (the constitutive member of the Hsp70 family) (Udono et al., *Int. Immunol.* 13: 1233–1242, 2001); (d) amino acids 359–610 of *M. tuberculosis* Hsp70 (Wand et al., *Immunity* 15: 971–983, 2001); (e) for (a) to (d), corresponding regions in Hsp70 homologs from other species, and (f) amino acids 1 to 200 of mycobacterial Hsp65 (particularly *M. bovis* Hsp65) (Chu et al., U.S. Ser. No. 09/613,303 filed Jul. 10, 2000).

The stress proteins useful in the present invention can be obtained from any suitable organism, including, but not limited to: Gram-positive bacteria, Gram-negative bacteria, enterobacteria (e.g., *E. coli*), mycobacteria (particularly *M. leprae, M. tuberculosis, M. vaccae, M. smegmatis*, and *M. bovis*), yeast, Drosophila, and vertebrates (e.g., avians such as chickens, or mammals such as rats, mice, or primates, including humans).

To make a therapeutic (e.g., an immunotherapeutic) composition containing a fusion polypeptide, the polypeptide can be recombinantly produced in bacteria, yeast, plants or plant cells, or animals or animal cells. For example, fusion polypeptides according to the invention can be produced by transformation (transfection, transduction, or infection) of a host cell with a fusion polypeptide-encoding DNA fragment in a suitable expression vehicle. Suitable expression vehicles include plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LAC-SWITCH® Inducible Expression System (Stratagene; La Jolla, Calif.).

Those skilled in the field of molecular biology will understand that any of a wide variety of expression systems can be used to provide the recombinant fusion polypeptide. The precise host cell and vector used is not critical to the invention.

Proteins and polypeptides can also be produced by plant cells. For plant cells, viral expression vectors (e.g., cauliflower mosaic virus and tobacco mosaic virus) and plasmid expression vectors (e.g., Ti plasmid) are suitable. Such cells and vectors are available from a wide range of sources (e.g., the American Type Culture Collection, Manassas, Va.; also, see, e.g., Ausubel et al., *Current Protocols in Molecular Biology*, John Wiley & Sons, New York, 1994). The methods of transformation or transfection and the choice of expression vehicle will depend on the host system selected. Transformation and transfection methods are described, e.g., in Ausubel et al., supra. Expression vehicles may be chosen from those provided, e.g., in Pouwels et al., *Cloning Vectors: A Laboratory Manual*, 1985, Supp. 1987. The host cells harboring the expression vehicle can be cultured in conventional nutrient media adapted as needed for activation or repression of a chosen gene, selection of transformants or amplification of a chosen gene.

Where appropriate or beneficial, the nucleic acid encoding a fusion polypeptide can include a signal sequence for excretion of the fusion polypeptide, e.g., to facilitate isolation of the polypeptide from a cell culture. Specific initiation signals may also be required for efficient translation of inserted nucleic acid sequences. These signals include the ATG initiation codon and adjacent sequences. In some cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription or translation enhancer elements (e.g., ones disclosed in Bittner et al., *Methods in Enzymol.* 153:516, 1987). Additionally the gene sequence can be modified for optimal codon usage in the appropriate expression system, or alternatively, the expression host can be modified to express specific tRNA molecules to facilitate expression of the desired gene.

It would be useful if the fusion polypeptides were soluble under normal physiological conditions. Also within the invention are methods of using fusion proteins (or other configurations of proteins, including covalent and non-covalent complexes and mixtures) in which the stress protein (or an immunostimulatory fragment thereof) and the HBV antigen are fused to (or otherwise associated with) an unrelated third protein or polypeptide to create at least a tripartite protein or mixture of proteins. The third protein may facilitate purification, detection, or solubilization of the fusion or other complex, or it may provide some other function. For example, the expression vector pUR278 (Ruther et al., *EMBO J.* 2:1791, 1983) can be used to create lacZ fusion proteins. The pGEX vectors can be used to express foreign polypeptides as fusion proteins containing glutathione S-transferase (GST). In general, such fusion proteins are soluble and can be easily purified from lysed cells by adsorption to glutathione-agarose beads, followed by elution in the presence of free glutathione. The pGEX vectors are designed to include thrombin or factor Xa protease cleavage sites so that the cloned target gene product can be released from the GST moiety.

A fusion protein or covalent complex can be purified using an antibody that specifically binds a portion of the fusion or complex. Alternatively, other properties of the protein included can be exploited for purification (e.g. metal binding). For example, a system described in Janknecht et al. (*Proc. Natl. Acad. Sci. USA*. 88:8972, 1981) allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^+$ nitriloacetic acid-agarose columns, and histidine-tagged proteins are selectively eluted with imidazole-containing buffers. The same procedure can be used for a bacterial culture.

Alternatively, the third protein can be an immunoglobulin Fc domain. Such a fusion protein can be readily purified using an affinity column.

Fusion polypeptides, particularly those containing short antigenic fragments, can also be produced by chemical synthesis (e.g., by the methods described in *Solid Phase Peptide Synthesis*, 2nd ed., 1984 The Pierce Chemical Co., Rockford, Ill.).

Once isolated, the fusion polypeptide can, if desired, be further purified and/or concentrated, so long as further processing does not impair its ability to elicit (e.g., by inducing or enhancing) an immune response sufficient for implementation of the methods of the invention. A variety of methods for purification and concentration are well known in the art (see, e.g., Fisher, *Laboratory Techniques In Biochemistry And Molecular Biology*, Work and Burdon, eds., Elsevier, 1980), including ultracentrifugation and/or precipitation (e.g., with ammonium sulfate), microfiltration (e.g., via 0.45 $\mu$m cellulose acetate filters), ultrafiltration (e.g., with the use of a sizing membrane and recirculation filtration), gel filtration (e.g., columns filled with Sepharose CL-6B, CL-4B, CL-2B, 6B, 4B or 2B, Sephacryl S-400 or S-300, Superose 6 or Ultrogel A2, A4, or A6; all available from Pharmacia Corp.), fast protein liquid chromatography (FPLC), and high performance liquid chromatography (HPLC).

The polypeptides within the compositions of the invention can include antigenic or immunostimulatory determinants, or the whole protein, of more than one stress protein and/or more than one HBV protein. Optionally, the peptides can include other sequences to which an immune response is desired.

The invention includes immunotherapeutic compositions containing at least one fusion polypeptide as described herein, and, optionally, a pharmaceutically acceptable carrier, such as a diluent, e.g., saline, phosphate buffered saline, or a bicarbonate solution (e.g., 0.24 M $NaHCO_3$). The carriers used in the composition are selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, or immune-stimulating complex (ISCOM), can also be included in the immunotherapeutic compositions.

The compositions can be formulated as a solution (suitable for intramuscular, intradermal, or intravenous administration), suspension, suppository, tablet, granules, a powder, a capsule, ointment, or cream. In preparing these compositions, one or more pharmaceutical carriers can be included. Examples of pharmaceutically acceptable carriers or other additives include solvents (e.g., water or physiological saline), solubilizing agents (e.g., ethanol, polysorbates, or Cremophor EL®), agents for rendering isotonicity, preservative, antioxidizing agents, excipients (e.g., lactose, starch, crystalline cellulose, mannitol, maltose, trehalose, calcium hydrogen phosphate, light silicic acid anhydride, or calcium carbonate), binders (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizers (e.g., lactose, mannitol, maltose, polysorbates, macrogels, or polyoxyethylene-hardened castor oils). If necessary, glycerin, dimethylacetamide, sodium lactate, a surfactant, sodium hydroxide, ethylenediamine, ethanolamine, sodium bicarbonate, arginine, meglumine, or trisaminomethane is added. Biodegradable polymers such as poly-D,L-lactide-co-glycolide or polyglycolide can be used as a bulk matrix if slow release of the composition is desired (see e.g., U.S. Pat. Nos. 5,417,986, 4,675,381, and 4,450,150). As noted above, pharmaceutical preparations such as solutions, tablets, granules or capsules can be formed with these components. If the composition is administered orally, flavorings and colors can be added.

The immunotherapeutic compositions can be administered via any appropriate route, e.g., intravenously, intraarterially, topically, by injection (e.g. intraperitoneally, intrapleurally, subcutaneously, intramuscularly), orally, intradermally, sublingually, intraepidermally, intranasally (e.g., by inhalation), intrapulmonarily, or rectally.

The amount of immunotherapeutic composition administered will depend, for example, on the particular stress protein/antigen composition, whether an adjuvant is co-administered with the composition, the type of adjuvant co-administered, the mode and frequency of administration, and the desired effect (e.g., protection or treatment), as can be determined by one skilled in the art. In general, the immunotherapeutic compositions are administered in amounts ranging between 1 $\mu$g and 100 mg per adult human dose. Preferably, between 50 to 10,000 $\mu$g (e.g., about 100 to 5000 $\mu$g, especially about 500, 1000, 1500 or 2000 $\mu$g) of the fusion protein is administered. If adjuvants are administered with the immunotherapeutic, amounts ranging between 1 ng and 100 mg per adult human dose can generally be used. Administration is repeated as necessary, as can be determined by one skilled in the art. For example, a priming dose can be followed by one or more booster doses at weekly or monthly intervals. A booster shot can be given at 3 to 12 weeks after the first immunization, and a second booster can be given at 3 to 12 weeks after the first booster, using the same formulation or a different formulation. Serum, PBLs, or PBMCs, can be taken from the individual for testing the immune response elicited by the immunotherapeutic against the HBV antigen included in the fusion protein. Methods of assaying antibodies or cytotoxic T cells or cytokine-secreting cells against a specific antigen are well known in the art. Additional boosters can be given as needed. By varying the amount of fusion polypeptide in the composition, the immunization protocol can be optimized for eliciting a maximal immune response.

Of course, the polypeptides (alone or as part of a fusion protein) can also be delivered by administering a nucleic acid, such as a viral vector (e.g., a retroviral or adenoviral vector).

The immunotherapeutic of the invention can also be administered in combination with one or more compounds or compositions that have activity against HBV (an HBV antiviral). For example, a patient can first be treated with an HBV antiviral to reduce the severity of the HBV infection (as measured by, for example, reduction or loss of circulating HBe antigen (a marker of HBV replication and high-titre viremia), appearance of anti-HBe antibodies, reduction or disappearance of serum HBV DNA or reduction in alanine aminotransferase (ALT) levels). Once a suitable reduction is achieved, the immunotherapeutic of the invention can then be administered to the patient. Alternatively, the HBV antiviral and the immunotherapeutic can be administered at substantially the same time (keeping in mind that the antiviral and the immunotherapeutic may have different routes of administration), or the immunotherapeutic can be administered first, followed by treatment with the antiviral. Antiviral compounds or compositions suitable for use in such combinations with the immunotherapeutic include, but are not limited to interferon-α2b (Intron A, Schering Plough), pegylated interferon-α2b, and nucleoside analogs such as lamivudine [(−)-β-L-3'-thia-2 ',3'-dideoxycytidine or 3TC] (Epivir-HBV, Glaxo Wellcome) and ribavirin (Rebetron™, ICN Pharmaceuticals). There are a number of additional experimental compounds which may be suitable, and these include: hemtricitabine (2',3'-dideoxy-5'-fluoro-3'-thiacytidine, FTC, coviracil, Triangle Pharmaceuticals), clevudine (2'-fluoro-5-methyl-β-L-arabinofuranosyl uracil, L-FMAU, Triangle), adefovir (9-(2-phosphonylmethyl)-adenine, PMEA, Gilead Sciences), entecavir (Bristol-Myers Squibb), (−)-beta-D-2, 6-diaminopurine dioxolane (DAPD), β-L-2',3'-dideoxy-5-fluorocytidine (β-L-FddC), β-L-2',3'-didehydro-dideoxy-5-fluorocytidine (β-L-Fd4C), and famciclovir.

Without further elaboration, it is believed that one skilled in the art can, based on the above disclosure and the example below, utilize the present invention to its fullest extent. The following example is to be construed as merely illustrative of how one skilled in the art can isolate and use the fusion polypeptides, and is not limitative of the remainder of the disclosure in any way. All publications cited in this disclosure are hereby incorporated by reference.

EXAMPLES

Example 1

Construction of HBV Core Antigen-Hsp Fusion Proteins

General methods and procedures for constructing fusion proteins can be found in WO 94/29459, WO 98/23735, WO 99/07860, and references cited therein.

The gene encoding the HBV subtype adw was obtained from plasmid pBR/HBV (purchased from the ATCC, ATCC 45020). The coding sequence for the full length protein is shown in FIG. 1, and the amino acid sequence of the fall length protein is depicted in FIG. 2.

The gene encoding the full length *M. bovis BCG* Hsp65 protein was obtained from plasmid pET65 (see WO 99/07860).

Using these starting materials and appropriate primers, the following constructs were prepared and cloned into pET28a (Novagen) for protein production:

1.1 hisHepCorT(149/87S97F): DNA encoding a truncated HBV core antigen (amino acids 1 to 149). The construct also contains an N-terminal 20 amino acid sequence containing a histidine tag. This construct has two amino acid changes from the wild type protein: amino acid 87 was changed from asparagine to serine and amino acid 97 was changed from isoleucine to phenylalanine. These two changes were made to reproduce known mouse CTL epitopes. There is also an exogenous asparagine residue added to the C-terminus of the truncated protein. The DNA sequence is shown in FIG. 3, and the encoded amino acid sequence is shown in FIG. 4.

1.2 hisHepCor(97F)Hsp65: DNA encoding a fusion protein comprised of amino acids of the full length HBV core protein fused to the N-terminus of *M. bovis BCG* Hsp65. The construct also contains an N-terminal 20 amino acid sequence containing a histidine tag and has amino acid 97 changed from isoleucine to phenylalanine. There are two additional residues inserted between the HBV core protein and the Hsp65 protein: an asparagine and a valine. The DNA sequence is shown in FIG. 5, and the encoded amino acid sequence is shown in FIG. 6.

1.3 hisHepCorT(149/87S97F)Hsp65: DNA encoding a fusion protein comprised of amino acids 1 to 149 of HBV core fused to the N-terminus of *M. bovis BCG* Hsp65. The construct also contains an N-terminal 20 amino acid histidine tag and has an additional asparagine residue between the HBV core protein and the Hsp65 protein. The DNA sequence is shown in FIG. 7, and the encoded amino acid sequence is shown in FIG. 8.

1.4 HepCorT(151/97F)Hsp65: DNA encoding a fusion protein comprised of amino acids 1 to 151 of the HBV core protein fused to the N-terminus of *M. bovis BCG* Hsp65 (with no extra amino acids inserted between the two sequences). The HBV core sequence was modified from the wild type sequence as follows: isoleucine 97 is changed to phenylalanine. The DNA sequence is shown in FIG. 9, and the encoded amino acid sequence is shown in FIG. 10.

1.5 HepCor(97F)Hsp65: DNA encoding a fusion protein comprised of the full length HBV core protein fused to the N-terminus of *M. bovis* BCG Hsp65 (with no extra amino acids inserted between the two sequences). Like the construct directly above, amino acid 97 of the HBV core was changed from isoleucine to phenylalanine. The DNA sequence is shown in FIG. 11, and the encoded amino acid sequence is shown in FIG. 12.

1.6 HepCorT(151/97F). DNA encoding a truncated HBV core antigen (amino acids 1 to 151). This construct, in addition to being truncated at amino acid 151, has one amino acid change from the wild type adw protein shown in FIG. 2: amino acid 97 was changed from isoleucine to phenylalanine in order to reproduce a known mouse CTL epitope.

1.7 HepCor(97F). DNA encoding the full length HBV core antigen. This construct has one amino acid change from the wild type adw protein shown in FIG. 2: amino acid 97 was changed from isoleucine to phenylalanine in order to reproduce a known mouse CTL epitope.

Additional constructs can be made using other stress proteins, such as Hsp70 from *Mycobacterium tuberculosis.*

The HBc molecule was in some instances modified by introducing one or more amino acid substitutions into the HBc gene product in order to reproduce known mouse-specific CTL epitopes. One of the substitutions was introduced at amino acid position 87, where asparagine was replaced by serine. This substitution created the mouse CTL epitope ($^{87}$SYVNTNMGL$^{95}$) restricted by H-2K$^{d}$ (HBc.Kd) (Kuhrober, et al., *Int. Immunol.* 9:1203–1212, 1997). The second substitution was introduced at amino acid position 97, where isoleucine was replaced by phenylalanine. This substitution created the murine CTL epitope ($^{93}$MGLKFRQL$^{100}$) restricted by H-2K$^{b}$ (HBc.Kb) (Kuhober et al., *J. Immunol.* 156:3687–3695, 1996). A DNA fragment encoding 20 amino acids that contains six histidine residues (His-Tag) was added to the N-terminus of the some of the constructs to facilitate purification. The fusion proteins can easily be made without these modifications.

Example 2

Protein Purification

The following abbreviations are used: BCG for *Mycobacterium bovis* var. Bacille-Calmette-Guérin; CV for column volume; ET for endotoxin; EU for endotoxin units; IB for inclusion body or bodies; MT for *Mycobacterium tuberculosis*; and PBS for phosphate-buffered saline.

All constructs were grown in a 15 L fermentor (Braun ED). The bacterial cell-paste was stored at −70° C. until used for protein purification.

2.1 Purification of hisHepCorT(149/87S97F)

Cell Lysis: Approximately 277 g of the frozen cell paste was mixed with 800 mL of Lysis Buffer (30 mM TRIS, 10 mM 2-mercaptoethanol, 2 mM EDTA, 0.2 mM PMSF, pH 8.5). Then, lysozyme was added to 200 µg/mL and 50 µL of Benzonase™. The cells were frozen overnight at −70° C., then thawed for one hour, aliquoted into 50 mL centrifugation tubes, stored on ice, and sonicated with a BRANSON Sonifier II fitted with a 0.5 inch tip at setting 9 for 6 times 45 seconds.

The cell debris and IB were separated from the supernatant by centrifugation at 17,000 RPM (Beckman, Avanti J-30, JA30.50 rotor) for 20 min at 4° C. The pellet was re-suspended in 25 mL per tube with Wash Buffer (30 mM TRIS, 10 mM 2-mercaptoethanol, 2% (v/v) Triton X-100, pH 8.5). After centrifugation at 22,000 RPM for 20 min at 4° C., the supernatant was discarded and 20 mL of 8 M urea, 30 mM TRIS, 10 mM 2-mercaptoethanol, 1 mM EDTA, 0.2 mM PMSF, pH 8.5 were added and incubated overnight at 4° C. The supernatant with the dissolved IB was harvested by centrifugation at 22,000 RPM for 30 min, then split into two parts and frozen at −70° C.

Ni Chelating Chromatography: 250 mL of Chelating Sepharose Fast Flow (Amersham-Pharmacia) was packed into a XK50/30 column (Amersham-Pharmacia). The resin was washed with 3 CV each of 50 mM EDTA, Milli-Q™ quality water, 0.5 M NaOH, 2 M NaCl, Milli-Q™ quality water, 70% (v/v) ethanol, and Milli-Q™ quality water. Then, the resin was charged with 200 mM of $NiSO_4$, washed with Milli-Q™ quality water, and equilibrated with 5 CV of Start Buffer (6 M guanidine HCl, 30 mM TRIS, 2 mM 2-mercaptoethanol, 20 mM imidazole, pH 8.5).

One part of the sample was applied onto the column at 5 mL/min, then washed with Start Buffer at 10 mL/min until the monitored absorption at 280 nm reached a baseline. To remove ET, the column was washed with 5 CV of 6 M guanidine HCl, 30 mM TRIS, 2 mM 2-mercaptoethanol, 20 mM imidazole, 2% (v/v) Triton X-100, pH 8.5. Subsequently, the column was washed with 6 M urea, 30 mM TRIS, 2 mM 2-mercaptoethanol, 20 mM imidazole, pH 8.5. then the protein was eluted with a 5 CV gradient from 0 to 500 mM imidazole in 6 M urea, 30 mM TRIS, 2 mM 2-mercaptoethanol, 20 mM imidazole, pH 8.5 at 5 mL/min.

This chromatographic step was repeated with the second part of the sample and the fractions containing relatively pure protein were pooled.

Source 15Q Anion-Exchange Chromatography: 60 mL of Source 15Q resin (Amersham-Pharmacia) was packed into a XK26/40 column (Amersham-Pharmacia). The resin was washed at 5 mL/min with 2 CV Milli-Q™ quality water, 3 CV 1 M NaOH, 3 CV Milli-Q™ quality water, 2 CV NaCl, 2 CV Milli-Q™ quality water, 2 CV of a mixture of 10% (v/v) acetic acid & 40% (v/v) iso-propanol, 2 CV Milli-Q™ quality water, then equilibrated with 3 CV Start Buffer (6 M urea, 30 mM TRIS, 10 mM 2-mercaptoethanol, 1 mM EDTA, pH 8.5).

The pooled sample from the previous step was applied to the column at 0.5 mL/min then washed with Start Buffer at 6 mL/min, until the monitored absorbance at 280 nm reached a baseline. The column was then washed with 10 CV of 2% (v/v) Triton X-100 in Start Buffer. The protein was eluted with 11 CV from 0 to 600 mM NaCl in Start Buffer.

This chromatographic step was repeated and the fractions containing relatively pure protein were pooled.

Source 15S Cation-Exchange Chromatography: 50 mL of Source 15S resin (Amersham-Pharmacia) was packed into a XK26/40 column (Amersham-Pharmacia). The resin was washed at 5 mL/min with 2 CV 1 M NaOH, 3 CV Milli-Q™ quality water, 2 CV NaCl, 2 CV Milli-Q™ quality water, 2 CV of a mixture of 10% (v/v) acetic acid and 40% (v/v) iso-propanol, 2 CV Milli-Q™ quality water, then equilibrated with 3 CV Start Buffer (6 M urea, 23 mM sodium acetate, 10 mM 2-mercaptoethanol, 1 mM EDTA, pH 4.8).

The pooled sample from the previous step was applied to the column at 3 mL/min, then washed with Start Buffer at 3 mL/min, until the monitored absorbance at 280 nm reached a baseline. The protein was partially eluted with 15 CV from 0 to 1,000 mM NaCl in Start Buffer at 6 mL/min, the reminder with 6 M guanidine HCl, 30 mM TRIS, 10 mM 2-mercaptoethanol, 1 mM EDTA, pH 8.5.

Dialysis and Sample Formulation: Subsequently, the pooled sample was dialysed against the following solutions, in the order given:

1. 4 L of 6 M urea, 30 mM TRIS HCl pH 8.5, 10 mM 2-mercaptoethanol, 1 mM EDTA, 0.8 M arginine, at 4° C., overnight.
2. 4 L of 3 M urea, 30 mM TRIS HCl pH 8.5, 2 mM 2-mercaptoethanol, 1 mM EDTA, 25% (w/v) sucrose, at 4° C., overnight.
3. 2 L of 30 mM TRIS HCl pH 8.5, 4.5 mM reduced glutathione, 0.5 mM oxidised glutathione, 0.8 M arginine, 25% (w/v) sucrose, at 4° C., overnight.
4. 2 L of 10 mM PBS pH 7.4, 4.5 mM reduced glutathione, 0.5 mM oxidised glutathione, 25% (w/v) sucrose, at 4° C., overnight.
5. Repetition of step 4.

Assuming each dialysis step was completed until equilibrium was reached, the final concentrations of the ingredients are: PBS 10 mM, reduced glutathione 4.5 mM, oxidized glutathione 0.5 mM, arginine $\leq$1.48 mM, urea$\leq$0.25 mM, sucrose 730 mM or 25% (w/v).

2.2 Purification of hisHepCorT(149/87S97F)Hsp65

Cell Lysis: 79 g of the frozen cell paste were mixed with 1,000 mL of Lysis Buffer (30 mM TRIS, 10 mM 2-mercaptoethanol, pH 7.5). The lysate was frozen overnight at −70° C. Then, it was thawed and lysozyme was added to 200 µg/mL and the cells were incubated for one hour. A mixture of several proteinase inhibitors (40 mg/mL each of aprotinin, leupeptin, pepstatin) and 15 µL Benzonase™ was added. The lysate was sonicated in a 250 mL Rosette Cooling Cell (Fisher) using a BRANSON Sonifier II fitted with a 0.5 inch tip at setting 7 for 6 times 60 seconds.

The cell debris and IB were separated from the supernatant by centrifugation at 23,000 RPM (Beckman, Avanti J-30, JA30.50 rotor) for 20 min at 4° C. Guanidine HCl was added to the supernatant to a concentration of 6 M, yielding 1,400 mL. The sample was divided into one 400 mL and two 500 mL fractions.

Ni Chelating Chromatography: 187 mL of Chelating Sepharose Fast Flow (Amersham-Pharmacia) was packed into a XK50/30 column (Amersham-Pharmacia). The resin, previously regenerated according to the recommendations of the manufacturer, was equilibrated with 5 CV of Start Buffer (6 M guanidine HCl, 50 mM imidazole, 30 mM TRIS, 1 mM 2-mercaptoethanol, pH 7.5).

The 400 mL sample was applied onto the column at 10 mL/min, then washed with Start Buffer until the monitored absorption at 280 nm reached a baseline. To remove ET, the column was washed with 5 CV of 6 M guanidine HCl, 30 mM TRIS, 1 mM 2-mercaptoethanol, 2% (v/v) Triton X-100, pH 7.5. Subsequently, the column was washed with 8 M urea, 30 mM TRIS, pH 8.5. Then, the protein was eluted with a gradient from 0 to 500 mM imidazole in 8 M urea, 30 mM TRIS, 1 mM 2-mercaptoethanol, pH 7.5.

This chromatographic step was repeated using the two 500 mL fractions from the previous step. The fractions obtained in these three runs were pooled.

Source 30Q Anion-Exchange Chromatography: 167 mL of Source 15Q resin (Amersham-Pharmacia) was packed into a XK50/30 column (Amersham-Pharmacia). The resin was regenerated with 5 CV of 2 M NaCl, 1 M NaOH, Milli-Q™ quality water, 40% (v/v) iso-propanol, 10% (v/v) acetic acid, and Milli-Q™ quality water. Then, the column was equilibrated with 3 CV of Start Buffer (6 M urea, 30 mM TRIS, 10 mM 2-mercaptoethanol, pH 7.5).

The pooled fractions from the previous step were applied to the column at 10 mL/min, then washed with Start Buffer, until the monitored absorbances at 214 nm, 254 nm, and 280 nm reached a baseline. The protein was eluted with a gradient from 0 to 500 mM NaCl in Start Buffer at 6 mL/min. Fractions containing the desired protein were pooled.

Ceramic Hydroxyapatite Chromatography: 53 mL of Ceramic Hydroxyapatite was packed into a XK26/40 column (Amersham-Pharmacia), regenerated with 3 CV 1 M NaOH and 0.5 M sodium phosphate, pH 6.8. The column was then equilibrated with 6 M urea, 20 mM sodium phosphate, pH 6.8.

The pooled fractions from the previous column was applied at 5 mL/min, then washed with 6 M urea, 20 mM sodium phosphate, pH 6.8 until the monitored absorbances at 214 nm, 254 nm, and 280 nm reached a stable baseline. Impurities bound to the column while hisHepCorT(149/87S97F)Hsp65 was in the flow-through.

Dialysis and Sample Formulation: The flow-through from the previous chromatography was pooled (250 mL) and dialysed against the following solutions, in the order given:
1. 4 L of 3 M guanidine HCl, 10 mM sodium phosphate, 0.8 M arginine, 4.5 mM reduced glutathione, 0.5 mM oxidised glutathione, 25% (w/v) sucrose, at 4° C., overnight.
2. 4 L of 10 mM sodium phosphate, 4.5 mM reduced glutathione, 0.5 mM oxidised glutathione, 25% (w/v) sucrose, at 4° C., overnight.
3. Previous step was repeated Assuming each dialysis step was completed until an equilibrium was reached, the final concentrations of the ingredients are: Sodium phosphate 10 mM; urea 1.85 mM; reduced glutathione 4.5 mM; oxidised glutathione 0.5 mM; sucrose 730 mM or 25% (w/v).

Gel Filtration Chromatography: A HiLoad 26/60 Superdex 200 (Amersham-Pharmacia) gel filtration column, pre-packed by the manufacturer, was regenerated with 1 M NaOH, then equilibrated with 10 mM sodium phosphate, 4.5 mM reduced glutathione, 0.5 mM oxidised glutathione, 25% (w/v) sucrose, pH 7.4.

The dialysed sample was split into three portions (30 mL, 20 mL, 20 mL) and individually run on the column in the equilibration buffer at 1.5 or 2 mL/min and the fractions containing the protein were pooled.

2.3 Purification of HepCorT(151/97F)Hsp65

Cell Lysis: 500 g of frozen cell-paste was mixed with 2500 mL of Lysis Buffer (30 mM TRIS, 10 mM 2-mercaptoethanol, 2 mM EDTA, 0.1 mM PMSF, 10 mg/mL aprotinin, 10 mg/mL leupetin, 5 mM p-amino-benzamidine, 0.2 mg/mL lysozyme, pH 7.5), then frozen at −70° C. for a minimum of 2 hours.

The frozen cell suspension was thawed at 37° C., stored on ice and sonicated (Branson Sonifier 450, ¾" tip) 4 times for 1 min. The lysate was centrifuged at 15,000 g, the soluble fraction clarified at 64,000 g, and the soluble sample retained. After adding 6M urea to the soluble fraction, it was divided into three equal sized portions.

Source 30Q Chromatography: A XK50/30 column (Amersham-Pharmacia) containing 190 mL Source 30Q resin (Amersham-Pharmacia) was regenerated then equilibrated with 3 CV of Start Buffer (6M urea, 30 mM TRIS, 10 mM 2-mercaptoethanol, 1 mM EDTA, pH 7.5).

One portion of the sample was applied to the column. The resin was washed with Start Buffer until the absdorption at 280 nm, 254 nm, and 214 nm reached a baseline, then the protein was eluted in a 5 CV linear gradient from 0 to 500 mM NaCl in Start Buffer. The fractions containing HepCor65T(151/97F) were pooled.

The chromatographic step was repeated with the other two portions of the sample. The pools of all three portions were combined and dialyzed against 6M urea, 25 mM sodium acetate, 10 mM 2-mercaptoethanol, 1 mM EDTA, pH 5.5 The sample was then divided into two portions.

Source 15S Chromatography pH 5.5: A XK26/40 column (Amersham-Pharmacia) containing 50 mL of Source 15S resin (Amersham-Pharmacia) was regenerated, then equilibrated with Start Buffer S1 (6M urea, 25 mM sodium acetate, 10 mM 2-mercaptoethanol, 1 mM EDTA, pH 5.5).

One portion of the Source 30Q sample was applied onto the column, washed with a) Start Buffer S1 until the baseline was stable at 280 nm, b) 10 CV of 2% (v/v) Triton X-100 in Start Buffer S1, and c) with Start Buffer S1 until the 280 nm baseline was stable. Finally the protein was eluted in a 18 CV linear gradient from 0 to 230 mM NaCl. The remaining protein was stripped off the column with a 1M NaCl wash step.

The chromatographic step was repeated with the second portion from the Source 30Q. The fractions containing HepCor65T(151/97F) were pooled, adjusted to pH 4.8 with concentrated acetic acid, and divided into two portions.

Source 15S Chromatography pH 4.8: The Source 15S column was regenerated and equilibrated with Start Buffer S2 (6M urea, 25 mM sodium acetate, 10 mM 2-mercaptoethanol, 1 mM EDTA, pH 4.8).

One portion of the Source 15S sample was applied onto the column, washed with a) Start Buffer S2 until the baseline was stable at 280 nm, b) 10 CV of 2% (v/v) Triton X-100 in Start Buffer S2, and c) with Start Buffer S2 until the 280 nm baseline was stable.

The protein was eluted in a 10 CV linear gradient from 0 to 500 mM NaCl in Start Buffer S2. The remaining protein was stripped off the column with a 2 CV 1M NaCl wash step and a final 3 CV 6M guanidine-HCl strip. The fractions containing HepCorT(151/97F)Hsp65 were pooled.

Source 15S Chromatography pH 4.8—Endotoxin Removal: After dialyzing the pooled fractions from the previous step in Start Buffer S2, it was reapplied to the Source 15S column.

The Source 15S column was regenerated and equilibrated with Start Buffer S2. One half of the Source 15S sample was applied onto the column, washed with Start Buffer S2 until the baseline at 280 nm was stable, then with 10 CV of 2% (v/v) Triton X-100 in Start Buffer S2, and again with Start Buffer S2 until the baseline at 280 nm was stable.

The protein was eluted in a 4 CV 1M NaCl wash step and a final 3 CV 6M guanidine-HCl strip. The fractions containing HepCor65T(151/97F) were pooled and dialyzed in three steps into DPBS, 10% (w/v) sucrose.

2.4 Purification of HepCor(97F)Hsp65

Cell Lysis: 200 g of frozen cell-paste were mixed with 600 mL of Lysis Buffer (30 mM TRIS, 20 mM 2-mercaptoethanol, 5 mM EDTA, 0.1 mM PMSF, 0.2 mg/mL lysozyme, pH 7.5) and then stirred at 4° C. for approximately 30 min.

The cell suspension was sonicated (Branson Sonifier 450, ¾" tip, Setting 9) 4 times for 1 min. The lysate was centrifuged at 18,500 g and the soluble sample retained. The protein solution was clarified by centrifugation for 20 min at 4° C. at 108,850 g.

Ammonium Sulfate Precipitation: To the clarified protein solution ammonium sulfate was added to 25% saturation and the protein pelleted at 10,000 g. The pellet was re-suspended in Lysis Buffer.

Acetic Acid Precipitation: The protein solution was carefully adjusted to pH 4.5 with 1M acetic acid and then stirred for 20 min at 4° C. The protein was then pelleted for 10 min at 10,000 g and 4° C. The protein pellet was re-suspended in Q Buffer A (6M urea, 30 mM TRIS, 10 mM 2-mercaptoethanol, 5 mM EDTA, 0.1 mM PMSF, pH 8.5).

Q Sepharose High Performance Chromatography: A XK50/30 column (Amersham-Pharmacia) containing 150 mL Q Sepharose High Performance resin (Amersham-Pharmacia) was regenerated then equilibrated with 3–5 CV of Q Buffer A. The sample was applied to the column and collected in the flow through. 2-mercaptoethanol was added to 150 mM and the protein pool incubated for 1 hour at 4° C.

Second Q Sepharose High Performance Chromatography: The Q Sepharose High Performance column was regenerated then equilibrated with Q Buffer A.

The flow-through off the first Q Sepharose Fast Flow column was applied to the column and again collected in the flow through. 2-mercaptoethanol was added to 300 mM. Guanidine-hydrochloride was added to 6M. The protein sample was then incubated for 72 h at RT, then filtered through A 0.22 $\mu$M filter.

Superdex 200 Gel Filtration Chromatography: A XK50/90 column (Amersham-Pharmacia) containing 1800 mL Superdex 200 resin (Amersham-Pharmacia) was equilibrated with 2 CV of GF Buffer (6M urea, 30 mM TRIS, 20 mM 2-mercaptoethanol, 2 mM EDTA, pH 7.5).

The sample was divided into 10 equal portions of 70 mL. Then the individual portions were processed on this column and the fractions containing HepCor(97F)Hsp65 pooled.

Sephadex 25 Desalting Gel Filtration Chromatography: A XK50/30 column (Amersham-Pharmacia) containing 300 mL Sephadex 25 resin (Amersham-Pharmacia) was regenerated then equilibrated with GF25 Buffer (6M urea, 50 mM acetic acid, 5 mM NaOH, 1 mM EDTA, 10 mM 2-mercaptoethanol, pH 4.7).

The sample was divided into 75 mL portions and subsequently processed. The protein containing fractions were pooled.

SP Sepharose High Performance Chromatography: 275 mL SP Sepharose High Performance resin (Amersham-Pharmacia) were regenerated then equilibrated with SP Buffer A (6M urea, 50 mM acetic acid, 5 mM NaOH, 1 mM EDTA, 10 mM 2-mercaptoethanol, pH 4.7).

The pooled sample obtained in the previous step was mixed with the resin and incubated on a horizontal shaker for 30 min at RT. Then the slurry was packed into a XK50/30 column (Amersham-Pharmacia) and washed with 2 CV of SP Buffer A. The column was then washed with 15 CV of 2% (v/v) Triton X-100 in SP Buffer A. The detergent was removed during a wash with 5 CV SP Buffer A and 2 CV of 1M NaCl in SP Buffer A. The protein was then eluted isocratically in 6M urea, 10 mM TRIS, pH 7.5.

Copper Chelating Sepharose Fast Flow Chromatography: A XK50/30 column (Amersham-Pharmacia) containing 180 mL Chelating Sepharose Fast Flow resin (Amersham-Pharmacia) was regenerated, loaded with copper sulfate, then equilibrated with 2 CV Cu Buffer A (6M guanidine-hydrochloride, 30 mM sodium phosphate, pH 7.0).

The sample was applied to the column, washed with 3 CV of Cu Buffer A, then with 5 CV of 2% (v/v) TritonX-100 in Cu Buffer A, finally with 3 CV of Cu Buffer A to remove the detergent. The protein was eluted with 300 mM imidazole in Cu Buffer A. The protein was subsequently dialyzed in 5 steps into DPBS.

2.5 Purification of HepCorT(151/97F)

Cell Lysis: 425 g of frozen cell-paste were mixed with 2.5L of ice-cold 10 mM EDTA, 100 mM NaCl, 1 mM 2-mercaptoethanol, pH 8.0. After mixing the cell suspension, the cells were pelleted by centrifugation for 10 min at 10,500 g. The cells were re-suspended in 50 mM NaCl, 1 mM EDTA, 1 mM 2-mercaptoethanol, 0.2 g/mL lysozyme, pH 80, mixed and incubated on ice for 1 hour.

The cell suspension was sonicated (Branson Sonifier 450, ¾" tip, Setting 8) 2 times for 2 min. The lysate was centrifuged at 18,500 g and the soluble sample retained.

Ammonium Sulfate Precipitation: To the soluble fraction ammonium sulfate was added to 25% saturation, then impurities were pelleted at 10,000 g for 40 min. To the supernatant further ammonium sulfate was added to 35% saturation. After mixing for 30 min the protein is pelleted by centrifugation at 10,000 g for 30 min. The pellet was re-suspended in 1 mM EDTA, 1 mM 2-mercaptoethanol, pH 8.0 and clarified at 76,500 g for 20 min.

Second Ammonium Sulfate Precipitation: The sample from the first precipitation was dissolved in 1 mM EDTA, 1 mM 2-mercaptoethanol, pH 8.0 and reprocessed by the same procedure as described above.

Phenyl Sepharose Fast Flow Chromatography: A XK50/30 column (Amersham-Pharmacia) containing 200 mL Phenyl Sepharose Fast Flow resin (Amersham-Pharmacia) was regenerated, then equilibrated with 0.85M ammonium sulfate, 20 mM sodium phosphate, 1 mM EDTA, 1 mM 2-mercaptoethanol, pH 6.8.

To the sample, 1M sodium phosphate, 1 mM EDTA, 1 mM BME, pH 6.8 was added up to 10 mM sodium phosphate and ammonium sulfate to 20% saturation. One half of the sample was applied to the column and was washed with equilibration buffer until the absorption at 280 nm reached a baseline. The protein was eluted with 300 mL of a linear negative gradient to 20 mM sodium phosphate, 1 mM EDTA, 1 mM 2-mercaptoethanol, pH 6.8. The fractions containing HepCorT(151/97F) were pooled.

Second Phenyl Sepharose Fast Flow Chromatography: The column was regenerated and equilibrated with with 0.85M ammonium sulfate, 20 mM sodium phosphate, 1 mM EDTA, 1 mM 2-mercaptoethanol, pH 6.8.

The sample pool off the first Phenyl Sepharose FF column was diluted to 2.5 mg/mL protein with equilibration buffer. The diluted sample was then applied to the column, washed with equilibration buffer until the baseline at 280 nm was stable and eluted with 300 mL linear gradient to 20 mM sodium phosphate, 1 mM EDTA, 1 mM 2-mercaptoethanol, pH 6.8.

The fractions containing HepCorT(151/97F) were pooled and the protein pelleted by addition of ammonium sulfate to 35% saturation and subsequent centrifugation at 12,000 g for 50 min. The pellet was then re-dissolved in 700 mL of 8M urea, 10 mM sodium acetate, 30 mM acetic acid, 25 mM NaCl, 0.5 mM EDTA, 5 mM 2-mercaptoethanol, pH 8.0.

SP Sepharose fast Flow Chromatography: A XK50/30 column (Amersham-Pharmacia) containing 180 mL of SP Sepharose Fast Flow resin (Amersham-Pharmacia) was regenerated, then equilibrated with 5CV of 8M urea, 10 mM sodium acetate, 30 mM acetic acid, 25 mM NaCl, 0.5 mM EDTA, 5 mM 2-mercaptoethanol, pH 8.0.

One half of the sample was applied to the column and washed with equilibration buffer until the absorption at 280 nm reached a baseline. The protein was eluted in a 600 mL linear gradient from equilibration buffer to 10 mM sodium acetate, 30 mM acetic acid, 1M NaCl, 5 mM 2-mercaptoethanol, 0.5 mM EDTA. Finally, the column was stripped with 6M guanidine.HCl, 50 mMTRIS, pH 8.5.

The procedure was repeated with the second half of the sample, then the fractions containing HepCorT were pooled and dialyzed against of 6M urea, 20 mM TRIS, pH 8.5, 0.5 mM EDTA, 5 mM 2-mercaptoethanol, pH 8.5, finally against 6M urea, 20 mM TRIS, 5 mM 2-mercaptoethanol, pH 8.5.

Source 30Q Chromatography: A XK50/30 column (Amersham-Pharmacia) containing 150 mL of Source 30Q resin (Amersham-Pharmacia) was regenerated, then equilibrated with 4 CV of Equilibration Buffer (6M urea, 20 mM TRIS, 5 mM 2-mercaptoethanol, pH 8.5).

One third of the sample was applied to the column, washed with 95% equilibration buffer and 5% Elution Buffer (6M urea 1 mMNaCl, 20 mM TRIS, 5 mM 2-mercaptoethanol, pH 8.5), then the protein was eluted in a 1L linear gradient to 100% Elution Buffer.

The second and third part of the sample were processed accordingly. The fractions containing HepCorT were pooled, then dialyzed against 6M urea, 20 mM sodium acetate, 20 mM acetic acid, 0.5 mM EDTA, 1 mM 2-mercaptoethanol, pH 8.0.

SP Sepharose High Performance Chromatography: A XK50/30 column (Amersham-Pharmacia) containing 180 mL of SP Sepharose High Performance resin (Amersham-Pharmacia) was regenerated then equilibrated with 5 CV of 6M urea, 20 mM sodium acetate, 20 mM acetic acid, 0.5 mM EDTA, 1 mM 2-mercaptoethanol, pH 8.0.

One half of the sample was applied to the column and washed with Equilibration Buffer until the absorption at 280 nm reached a baseline.

Impurities were eluted in two linear gradients, i.e., from 0 to 1M NaCl in Equilibration Buffer, then in a linear gradient to Elution Buffer 2 (6M urea, 40 mM sodium acetate, 10 mM acetic acid, 0.5 mM EDTA, 1 mM 2-mercaptoethanol, pH 8.0). The column was washed with 2% (v/v) Triton X-100 in Elution Buffer 2, then with 10 CV Elution Buffer to remove the detergent. The protein was then eluted in a gradient to 6M urea, 50 mM TRIS, 0.5 mM EDTA, 5 mM 2-mercaptoethanol, pH 8.0.

After repeating the procedure with the second half of the sample the fractions containing HepCorT(151/9F) were combined and the protein dialyzed in 2 steps into 5 mM sodium phosphate, 50 mM NaCl, 3.1 mM urea, 20% (w/v) sucrose, pH 8.5.

2.6 Purification of HepCor(97F)

Cell Lysis: 100 g of frozen cell-paste were mixed with 400 mL of ice-cold 5 mM EDTA, 5 mM 2-mercaptoethanol, pH 8.0. After mixing the cell suspension, lysozyme was added to 0 0.2 g/mL and the suspension mixed and incubated on ice for 1 hour.

The cell suspension was sonicated (Branson Sonifier 450, ¾" tip, Setting 8) 2 times for 2 min, then 200 mL of ice-cold 20 mM sodium acetate, 5 mM acetic acid, 3M ammonium sulfate were added and mixed, well. The suspension was sonicated (Branson Sonifier 450, ¾" tip, Setting 8) 3 min. Finally, the lysate was centrifuged at 18,500 g and the soluble sample retained.

Ammonium Sulfate Precipitation: The soluble fraction was diluted with 1L of 0.85M ammonium sulfate. 70 g/L of solid ammonium sulfate were slowly added while mixing. After further 30 min of mixing, the suspension was centrifuged at 18,500 g for 60 min. Afterwards, the pellet was re-suspended in 500 mL 1 mM EDTA, 5 mM 2-mercaptoethanol. 113.4 g/L ammonium sulfate were slowly added while mixing; the solution was mixed for another 30 min. The protein was pelleted at 76,500 g for 20 min.

The pellet was re-dissolved by addition of 1M sodium phosphate, 1 mM EDTA, 5 mM 2-mercaptoethanol, 20% saturation ammonium sulfate to a final concentration of 5 mM sodium phosphate.

Phenyl Sepharose Fast Flow Chromatography: A XK50/30 column (Amersham-Pharmacia) containing 200 mL Phenyl Sepharose Fast Flow resin (Amersham-Pharmacia) was regenerated, then equilibrated with 0.85M ammonium sulfate, 5 mM sodium phosphate, 1 mM EDTA, 5 mM 2-mercaptoethanol, pH 6.8.

The sample was applied to the column and was washed with equilibration buffer until the absorption at 280 nm reached a baseline. The protein was eluted with a step-gradient to 6M urea. The fractions containing HepCorT were pooled and the protein precipitated by addition of ammonium sulfate to 32% saturation. After pelleting the protein at 12,100 g for 50, it was re-dissolved in 500 mL 8M urea, 5 mM TRIS, 5 mM 2-mercaptoethanol, pH 7.5.

Source 30Q Chromatography: A XK50/30 column (Amersham-Pharmacia) containing 150 mL of Source 30Q resin (Amersham-Pharmacia) was regenerated, then equilibrated with 4 CV of Equilibration Buffer (6M urea, 5 mM TRIS, 5 mM 5-mercaptoethanol, pH 7.5).

The sample was applied to the column, washed with Equilibration Buffer. The protein was eluted in a linear gradient from Equilibration Buffer to 6M urea, 1 M NaCl, 5 mM TRIS, 5 mM 2-mercaptoethanol, pH 7.5. The fractions containing HepCor(97F) were pooled and divided into three portions.

SP Sepharose High Performance Chromatography: A XK50/30 column (Amersham-Pharmacia) containing 190 mL of SP Sepharose High Performance resin (Amersham-Pharmacia) was regenerated, then equilibrated with 5CV of 6M urea, 30 mM sodium acetate, 10 mM acetic acid, 1 mM EDTA, 5 mM 2-mercaptoethanol, pH 8.0.

One portion of the sample was applied to the column and washed with 6M urea, 40 mM sodium acetate, 10 mM acetic acid, 0.5 mM EDTA, 1 mM 2-mercaptoethanol, 2% (v/v) Triton X-100, pH 8.0 for 20 CV. Then, in order to remove Triton X-100, the column was washed with 10CV of 6M urea, 40 mM sodium acetate, 10 mM acetic acid, 0.5 mM EDTA, 1 mM 2-mercaptoethanol, pH 8.0.

The protein was eluted in a 600 mL linear gradient to 6M urea, 20 mM TRIS, 1M NaCl, 1 mM 2-mercaptoethanol, 0.5 mM EDTA, pH 8.5.

The procedure was repeated with the other two portions of the sample, then the fractions containing HepCor(97F) were pooled. The protein was then dialyzed in 5 steps into 40 mM sodium acetate, 0.05 mM DTT, pH 6.5.

Example 3
Priming of Mice for CTL Activity

Mice: C57BL/6 (H-2$^b$) mice were purchased from Charles River Laboratories (St. Constant, PQ).

Cell lines: The EL4 thymoma cell line (H-2$^b$) was obtained from ATCC and cultured in Dulbecco's modified Eagles medium containing 10% FBS and 2 mM L-glutamine (DMEM-10). EL4.HBc.1D7 cells expressing HBc antigen were derived at Stressgen by transfecting EL4 cells with a plasmid encoding the full length HBc gene and the neomycin resistance marker. The gene for the full-length HBc antigen was cloned from the adw subtype of HBV, and modified to encode known murine H-2Kb- and H-2Kd-restricted CTL epitope sequences (2 amino acid changes from the wild type protein adw protein were made: amino acid 87 was changed from asparagine to serine and amino acid 97 was changed from isoleucine to phenylalanine. These two changes were made to reproduce known mouse CTL epitopes.). Transfected cells were selected in DMEM-10 containing 1500 μg/mL G418 and cloned by limiting dilution to obtain the EL4.HBc. 1D7 clone. Expression of HBc protein in this cell line was validated by Western immunoblot analysis using an HBc-specific antibody. The MHC Class I presentation of the H-2Kb-restricted CTL epitope was confirmed by lysis with a CTL line specific for this epitope. FACS analysis revealed a high level of MHC Class I expression on the transfectant, similar to that of the parental cell line.

Priming of mice for CTL activity: Mice were immunized (via subcutaneous injection in either the scruff of the neck or the interscapular region) with buffer or 2.9 nmol of one of the following: HepCorT(151/97F)Hsp65, HepCorT(97F)Hsp65, hisHepCorT(149/87S97F)Hsp65, HepCorT(151/97F), or HepCorT(97F). At seven days following immunization, mice were euthanized by $CO_2$ inhalation or cervical dislocation and their spleens removed. Single cell suspensions of spleen cells were prepared in CTL medium (RPMI-1640, 10% FBS, 2 mM L-glutamine, 1 mM sodium pyruvate, 50 μM 2-ME and 45 μg/mL gentamicin). 30×10$^6$ viable lymphoid cells were restimulated by incubating at 37° C./5% $CO_2$ in the presence of 1 μM HBc CTL epitope peptide HBc.93–100.Kb, MGLKFRQL (Kuhober et al., *J. Immunol.* 156:3687–95, 1996). This synthetic peptide (synthesized by Research Genetics, Huntsville, Ala.) used in the restimulation includes a murine CTL epitope restricted by H-2Kb.

Figure 14:
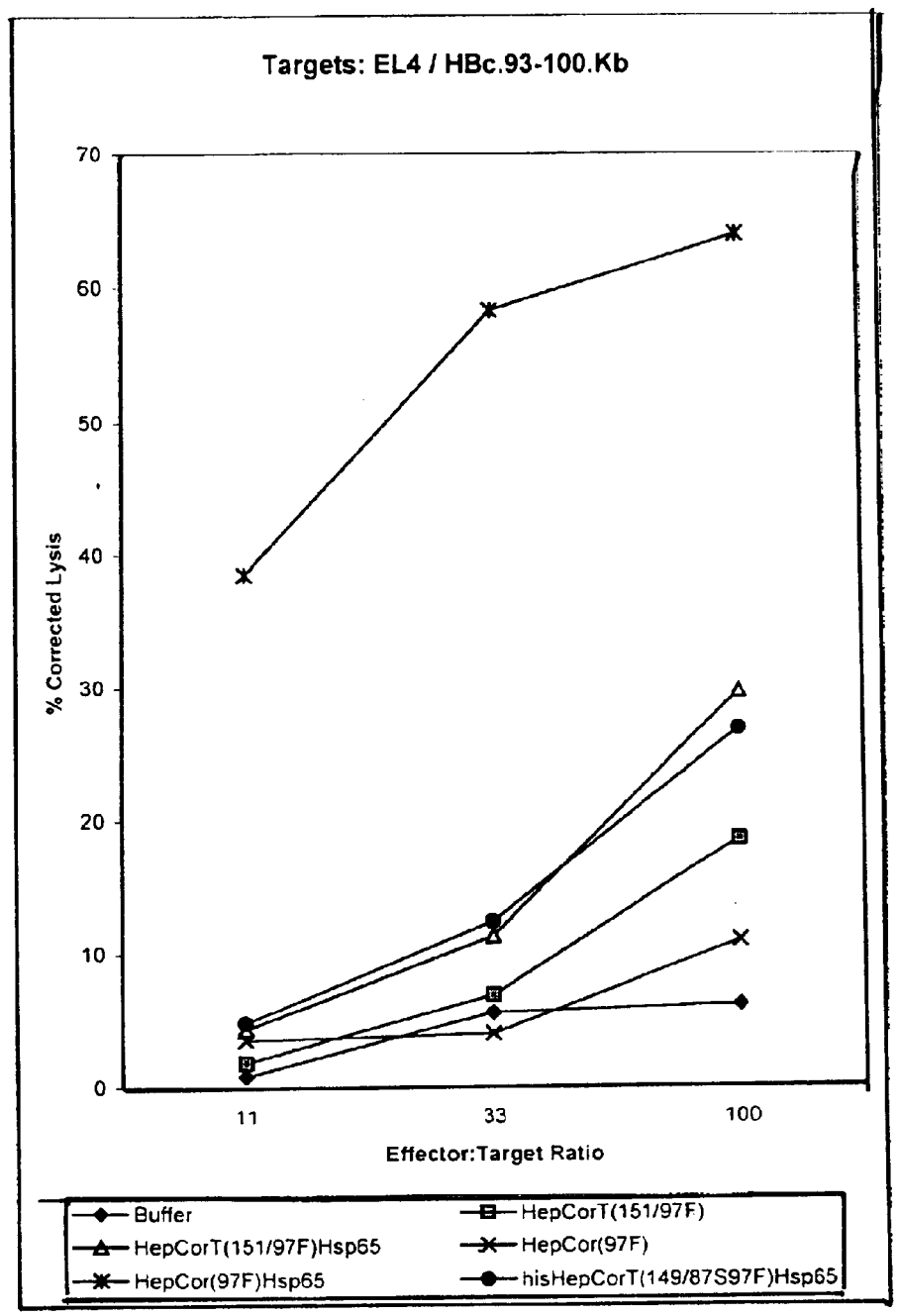
Figure 15:
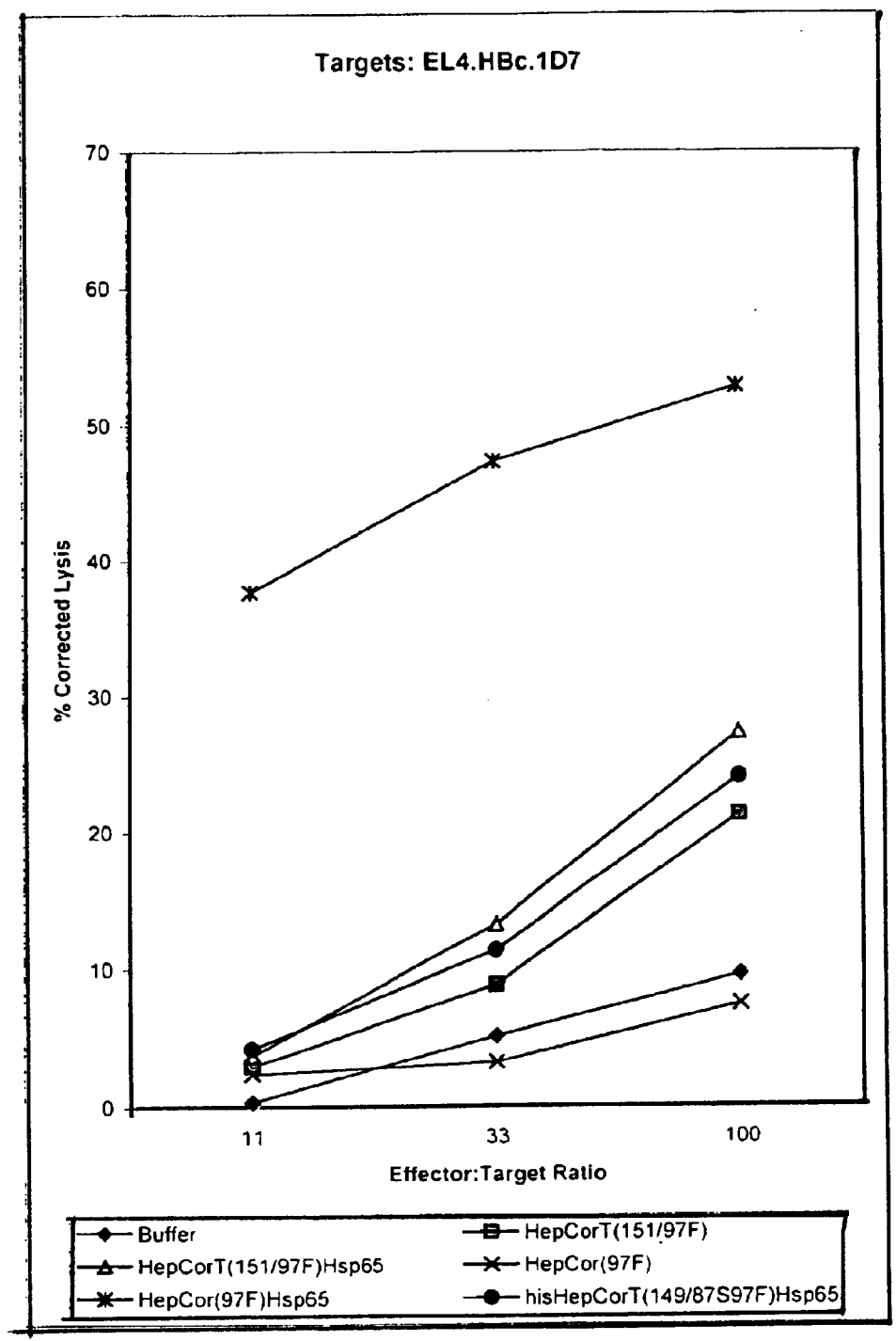

The effector cells were harvested after 7 days and cultured in U-bottomed 96 well microtitre plates together with $^{51}$Cr-labelled target cells. Control EL4 targets were cells pre-pulsed with an irrelevant H-2Kb-restricted (MUT-1.52–59.Kb) peptide (see FIG. 13). Target cells were EL4 cells pre-pulsed with either HBc.93–100.Kb peptide (see FIG. 14) or with EL4.HBc.1D7 cells (see FIG. 15). CTL (100 μl) were cultured with 5×10$^3$ or 1×10$^4$ target cells (100 μl) at various effector:target cell ratios (100:1, 33:1 or 11:1. To determine spontaneous release of label, an equal number of target cells were cultured without effector cells in a total of 200 μl of CTL medium. Total release of label was determined by adding 100 μl of Triton X-100 (2% v/v in water) to an equal number of target cells. After 4 hr incubation, the microtitre plates were centrifuged at 200×g for 5 min and 100 μl of culture supernatant were collected. The released radioactivity was determined by scintillation counting. The % corrected lysis was calculated according to the formula: % Corrected Lysis (CL)=100×($CPM_{test}$−$CPM_{spont}$)/($CPM_{total}$−$CPM_{spont}$)

Figure 16:
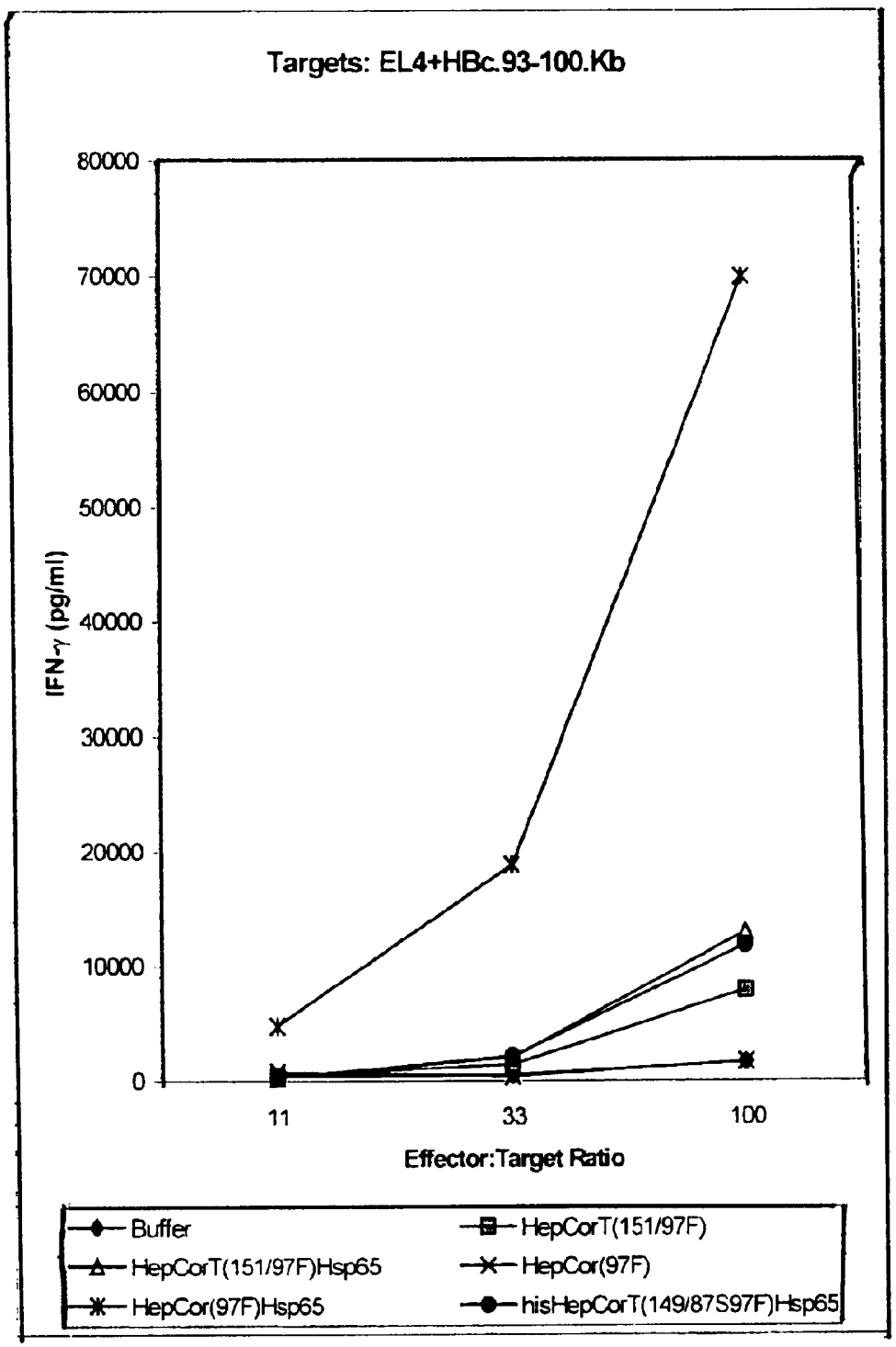
Figure 17:
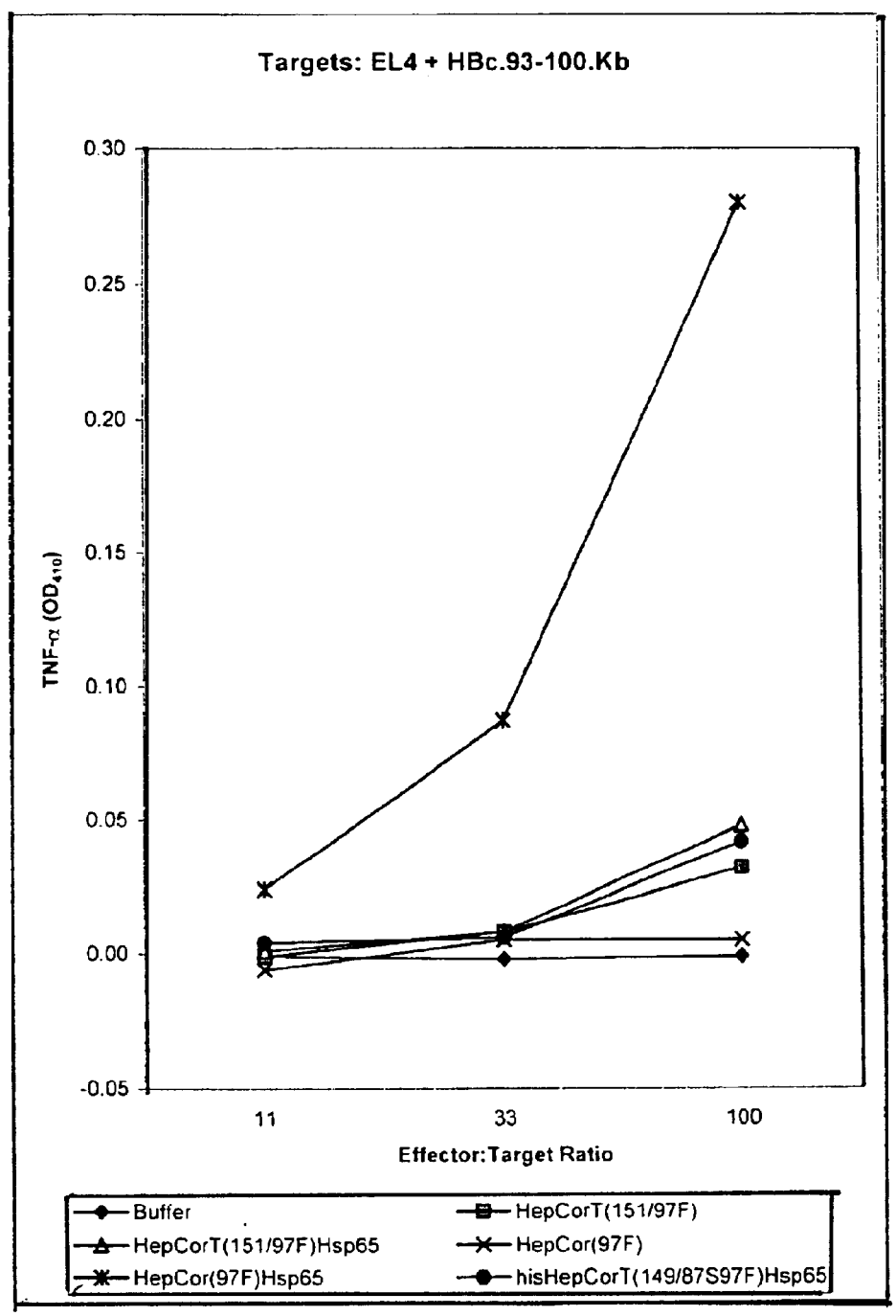

Cytokine analysis: In order to quantitate the release of gamma interferon (IFN-γ) and tumour necrosis factor alpha (TNF-α) from restimulated CTL, effector cells were seeded in U-bottomed 96 well microtitre plates and cultured together with 1 μM HBc.93–100.Kb peptide and target cells at effector: target ratios of 100:1, 33:1 or 11:1. Supernatants were harvested after 4 or 24 hr incubation and analyzed for IFN-γ (FIG. 16) or TNF-α (FIG. 17) levels by sandwich ELISA.

What is claimed is:

1. A fusion protein comprising (i) a stress protein or an immunostimulatory portion thereof and (ii) a variant of the hepatitis B virus (HBV) core antigen of SEQ ID NQ:2, wherein the variant comprises the amino acid sequence of SEQ ID NO:2 in which at least the isoleucine residue at vosition 97 but not more than 25 of the amino acid residues are substituted, and the fusion protein, when administered to an individual, induces or enhances an immune response against the HBV core antigen.

2. The fusion protein in claim 1, wherein the stress protein is a heat shock protein.

3. The fusion protein of claim 1, wherein the stress protein is selected from the group consisting of Hsp10, Hsp40, Hsp60, Hsp70, Hsp90, Hsp100–200, Hsp100, Lon, TF55, FKBPs, cyclophilin, Hsp20–30, ClpP, GrpE, ubiquitin, calnexin, a protein disulfide isomerase, and a ef small molecular weight stress protein family member.

4. The fusion protein of claim 1, wherein the stress protein is a mycobacterial stress protein.

5. The fusion protein of claim 4, wherein the mycobacterial stress protein is an M. bovis BCG stress protein.

6. The fusion protein of claim 5, wherein the M. bovis BCG stress protein is an M. bovis BCG hsp65 stress protein.

7. A fusion protein comprising the sequence of SEQ ID NO:6, SEQ ID NO:8, or SEQ ID NO:10.

8. A pharmaceutical composition comprising the fusion protein of any one of claims 1 to 7 and a pharmaceutically acceptable carrier or excipient.

9. A nucleic acid comprising a sequence that encodes the fusion protein of any one of claims 1 to 7.

10. A nucleic acid comprising the sequence of SEQ ID NO:5, SEQ ID NO:7, SEQ ID NO:9, or SEQ ID NO:11.

11. An expression vector comprising the nucleic acid of claim 9.

12. A retroviral vector comprising the nucleic acid of claim 9.

13. A cell comprising the expression vector of claim 11.

14. A method of making a fusion protein, the method comprising:
(a) providing the cell of claim 13, and
(b) culturing the cell under conditions that permit expression of the nucleic acid.

15. A method of inducing or enhancing an immune response against an HBV core antigen in a subject, the method comprising administering to the subject an effective amount of the fusion protein of any one of claims 1 to 7.

16. A method of inducing or enhancing an immune response against an HBV core antigen in a subject, the method comprising administering to the subject an effective amount of the pharmaceutical composition of claim 8.

17. A method of inducing or enhancing an immune response against an HBV core antigen, the method comprising administering to a subject an effective amount of the expression vector of claim 8.

18. A method of inducing or enhancing an immune response against an HBV core antigen, the method comprising administering to a subject an effective amount of the retroviral expression vector of claim 12.

19. The iselated fusion protein of claim 1, wherein 1–10 of the amino acid residues of SEQ ID NO:2 are substituted.

20. The isolated fusion protein of claim 19, wherein 1–5 of the amino acid residues of SEQ ID NO:2 are substituted.

21. The fusion protein of claim 20, wherein 1–2 of the amino acid residues of SEQ ID NO:2 are substituted.

22. The fusion protein of claim 1, wherein the isoleucine residue at position 97 is substituted with a conservative amino acid residue.

23. The fusion protein of claim 1, wherein the isoleucine residue at position 97 is substituted with phenylalanine.

24. The fusion protein of claim 1, wherein the threonine residue at position 91 is substituted.

25. The fusion protein of claim 24, wherein the threonine residue at position 91 is substituted with a conservative amino acid residue.

26. The fusion protein of claim 24, wherein the threonine residue at position 91 is substituted with valine.

27. The fusion protein of claim 1, wherein the asparagine residue at position 87 is substituted.

28. The fusion protein of claim 27, wherein the asparagine residue at position 87 is substituted with a conservative amino acid residue.

29. The fusion protein of claim wherein the asparagine residue at position 87 is substituted with valine.

30. An expression vector comprising the nucleic acid of claim 10.

31. A cell comprising the expression vector of claim 30.

32. A retroviral vector comprising the nucleic acid of claim 10.

33. The fusion protein of claim 1, wherein the stress protein is a full length stress protein.

34. The fusion protein in claim 33, wherein the stress protein is a heat shock protein.

35. The fusion protein of claim 33, wherein the stress protein is selected from the group consisting of Hsp10, Hsp40, Hsp60, Hsp70, Hsp90, Hsp100-200, Hsp100, Lon, TF55, FKBPs, cyclophilin, Hsp20–30, ClpP, GrpE, ubiquitin, calnexin, a protein disulfide isomerase, and a small molecular weight stress protein family member.

36. The fusion protein of claim 33, wherein the stress protein is a mycobacterial stress protein.

37. The fusion protein of claim 36, wherein the mycobacterial stress protein is an *M. bovis* BOG stress protein.

38. The fusion protein of claim 37, wherein the *M. bovis* BCG stress protein is an *M. bovis* BCG hsp65 stress protein.

39. A pharmaceutical composition comprising the fusion protein of claim 33 and a pharmaceutically acceptable carrier or excipient.

40. The fusion protein of claim 33, wherein 1–10 of the amino acid residues are substituted.

41. The fusion protein of claim 40, wherein 1–5 of the amino acid residues are substituted.

42. The fusion protein of claim 41, wherein 1–2 of the ammo acid residues are substituted.

43. A fusion protein comprising the amino acid sequence of SEQ ID NQ:12.

44. The fusion protein of claim 43, wherein the fusion protein consists of the amino acid sequence of SEQ ID NO:12.

45. A pharmaceutical composition comprising the fusion protein of claim 43 and a pharmaceutically acceptable carrier or excipient.

46. A pharmaceutical composition comprising the fusion protein of claim 44 and a pharmaceutically acceptable carrier or excipient.

47. A method of inducing or enhancing an immune response against an HBV core antigen in a subject, the method comprising administering to the subject an effective amount of the pharmaceutical composition of claim 45.

48. A method of inducing or enhancing an immune response against an HBV core antigen in a subject, the method comprising administering to the subject an effective amount of the pharmaceutical composition of claim 46.

49. A nucleic acid comprisipg a sequence that encodes the fusion protein of claim 43.

50. A nucleic acid comprising a sequence that encodes the fusion protein of claim 44.

51. An expression vector comprising the nucleic acid of claim 49.

52. An expression vector comprising the nucleic acid of claim 50.

53. A cell comprising the expression vector of claim 51.

54. A cell comprising the expression vector of claim 52.

55. A method of making a fusion protein, the method comprising:
  (a) providing the cell of claim 53, and
  (b) culturing the cell under conditions that permit expression of the nucleic acid.

56. A method of making a fusion protein, the method comprising:
  (a) providing the cell of claim 54, and
  (b) culturing the cell under conditions that permit expression of the nucleic acid.

57. A method of inducing or enhancing an immune response against an HBV core antigen, the method comprising administering to a subject an effective amount of the expression vector of claim 30.

58. A method of inducing or enhancing an immune response against an HBV core antigen, the method comprising administering to a subject an effective amount of the retroviral vector of claim 32.

59. A method of inducing or enhancing an immune response against an HBV core antigen, the method comprising administering to a subject an effective amount of the expression vector of claim 51.

60. A method of inducing or enhancing an immune response against an HBV core antigen, the method comprising administering to a subject an effective amount of the expression vector of claim 52.

61. A pharmaceutical composition comprising the fusion protein of any one of claims 19–21 or 22–25 and a pharmaceutically acceptable carrier or excipient.

62. A nucleic acid comprising a sequence that encodes the fusion protein of any one of claims 19–21 or 22–25.

63. An expression vector comprising the nucleic acid of claim 62.

64. A retroviral vector comprising the nucleic acid of claim 62.

65. A cell comprising the expression vector of claim 63.

66. A method of making a fusion protein, the method comprising:
  (a) providing the cell of claim 65, and
  (b) culturing the cell under conditions that permit expression of the nucleic acid.

67. A method of inducing or enhancing an immune response against an HBV core antigen in a subject, the method comprising admin4yering to the subject an effective amount of the fusion protein of any one of claims 19–25.

68. A method of inducing or enhancing an immune response against an HBV core antigen in a subject, the method comprising administering to the subject an effective amount of the pharmaceutical composition of claim 61.

69. A method of inducing or enhancing an immune response against an HBV core antigen, the method comprising administering to a subject an effective amount of the expression vector of claim 63.

70. A method of inducing or enhancing an immune response against an HBV core antigen, the method comprising administering to a subject an effective amount of the retroviral vector of claim 64.

* * * * *

UNITED STATES PATENT AND TRADEMARK OFFICE
CERTIFICATE OF CORRECTION

PATENT NO. : 6,921,534 B2
APPLICATION NO. : 10/068059
DATED : July 26, 2005
INVENTOR(S) : Lee A. Mizzen, Marvin Siegel and Hongwei Liu It is certified that error appears in the above-identified patent and that said Letters Patent is hereby corrected as shown below:

Page 2, Other Publications
Ardeshir, replace "Shcok" with -- Shock --
Arrigo, replace "15329-15369" with -- 15359-15369 --
Chu et al., replace "Mycobacteria" with -- Mycobacterium --
Chu et al., replace "121:216-226" with -- 121:216-225 --

Page 3, Other Publications
Jondal, replace "5:295-203" with -- 5:295-302 --
Lamb et al., replace "Provice" with -- Provide --
Moréet, replace "Moréet" with -- Moré et --
Moréet, replace "(1992)" with -- (1999) --
Noll, replace "Autenrietie" with -- Autenrieti --

Page 4, Other Publications
Pinskey, between "Prospective" and "Trail" insert -- , Randomized --
Pinskey, replace "Trail" with -- Trial --
Shinnick, replace "Etiological" with -- Etiologic --
Srivastava, replace "Toady" with -- Today --

Column 63
Line 39, replace "vosition" with -- position --
Line 49, between "a" and "small" delete "ef"

Column 64
Line 52, replace "claim 8" with -- claim 11 --
Line 57, after "The" delete "iselated"
Line 59, after "The" delete "isolated"

Column 65
Line 13, between "claim" and "wherein" insert -- 27 --
Line 33, replace "BOG" with -- BCG --

UNITED STATES PATENT AND TRADEMARK OFFICE
CERTIFICATE OF CORRECTION

PATENT NO. : 6,921,534 B2
APPLICATION NO. : 10/068059
DATED : July 26, 2005
INVENTOR(S) : Lee A. Mizzen, Marvin Siegel and Hongwei Liu It is certified that error appears in the above-identified patent and that said Letters Patent is hereby corrected as shown below:

<u>Column 66</u>
Line 36, replace "22-25" with -- 22-29 --
Line 39, replace "22-25" with -- 22-29 --
Line 52, replace "admin4yering" with -- administering --.
Line 53, replace "19-25" with -- 19-29 --

Signed and Sealed this

Tenth Day of October, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 558
<212> TYPE: DNA
<213> ORGANISM: Hepatitis B virus
<220> FEATURE:
<221> NAME/KEY: CDS
<222> LOCATION: (1)...(555)

<400> SEQUENCE: 1

```
atg gac att gac cct tat aaa gaa ttt gga gct act gtg gag tta ctc      48
Met Asp Ile Asp Pro Tyr Lys Glu Phe Gly Ala Thr Val Glu Leu Leu
 1               5                  10                  15 tcg ttt ttg cct tct gac ttc ttt cct tcc gtc aga gat ctc cta gac      96
Ser Phe Leu Pro Ser Asp Phe Phe Pro Ser Val Arg Asp Leu Leu Asp
                20                  25                  30 acc gcc tca gct ctg tat cgg gaa gcc tta gag tct cct gag cat tgc     144
Thr Ala Ser Ala Leu Tyr Arg Glu Ala Leu Glu Ser Pro Glu His Cys
            35                  40                  45 tca cct cac cac acc gca ctc agg caa gcc att ctc tgc tgg ggg gaa     192
Ser Pro His His Thr Ala Leu Arg Gln Ala Ile Leu Cys Trp Gly Glu
        50                  55                  60
```

```
ttg atg act cta gct acc tgg gtg ggt aat aat ttg gaa gat cca gca      240
Leu Met Thr Leu Ala Thr Trp Val Gly Asn Asn Leu Glu Asp Pro Ala
 65              70                  75                  80 tca agg gat cta gta gtc aat tat gtt aat act aac atg ggt tta aaa      288
Ser Arg Asp Leu Val Val Asn Tyr Val Asn Thr Asn Met Gly Leu Lys
                 85                  90                  95 att agg caa cta ttg tgg ttt cat ata tct tgc ctt act ttt gga aga      336
Ile Arg Gln Leu Leu Trp Phe His Ile Ser Cys Leu Thr Phe Gly Arg
                100                 105                 110 gag act gta ctt gaa tat ttg gta tct ttc gga gtg tgg att cgc act      384
Glu Thr Val Leu Glu Tyr Leu Val Ser Phe Gly Val Trp Ile Arg Thr
                115                 120                 125 cct cca gcc tat aga cca cca aat gcc cct atc tta tca aca ctt ccg      432
Pro Pro Ala Tyr Arg Pro Pro Asn Ala Pro Ile Leu Ser Thr Leu Pro
130                 135                 140 gaa act act gtt gtt aga cga cgg gac cga ggc agg tcc cct aga aga      480
Glu Thr Thr Val Val Arg Arg Arg Asp Arg Gly Arg Ser Pro Arg Arg
145                 150                 155                 160 aga act ccc tcg cct cgc aga cgc aga tct caa tcg ccg cgt cgc aga      528
Arg Thr Pro Ser Pro Arg Arg Arg Ser Gln Ser Pro Arg Arg Arg
                165                 170                 175 aga tct caa tct cgg gaa tct caa tgt tga                              558
Arg Ser Gln Ser Arg Glu Ser Gln Cys
                180                 185

<210> SEQ ID NO 2
<211> LENGTH: 185
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
 65              70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
                180                 185

<210> SEQ ID NO 3
```

-continued

<211> LENGTH: 513
<212> TYPE: DNA
<213> ORGANISM: Artificial Sequence
<220> FEATURE:
<221> NAME/KEY: CDS
<222> LOCATION: (1)...(510)
<223> OTHER INFORMATION: Nucleic acids encoding fusion protein

<400> SEQUENCE: 3

```
atg ggc agc agc cat cat cat cat cat cac agc agc ggc ctg gtg ccg      48
Met Gly Ser Ser His His His His His His Ser Ser Gly Leu Val Pro
 1               5                  10                  15 cgc ggc agc cat atg gac att gac cct tat aaa gaa ttt gga gct act      96
Arg Gly Ser His Met Asp Ile Asp Pro Tyr Lys Glu Phe Gly Ala Thr
             20                  25                  30 gtg gag tta ctc tcg ttt ttg cct tct gac ttc ttt cct tcc gtc aga     144
Val Glu Leu Leu Ser Phe Leu Pro Ser Asp Phe Phe Pro Ser Val Arg
         35                  40                  45 gat ctc cta gac acc gcc tca gct ctg tat cgg gaa gcc tta gag tct     192
Asp Leu Leu Asp Thr Ala Ser Ala Leu Tyr Arg Glu Ala Leu Glu Ser
     50                  55                  60 cct gag cat tgc tca cct cac cac acc gca ctc agg caa gcc att ctc     240
Pro Glu His Cys Ser Pro His His Thr Ala Leu Arg Gln Ala Ile Leu
 65                  70                  75                  80 tgc tgg ggg gaa ttg atg act cta gct acc tgg gtg ggt aat aat ttg     288
Cys Trp Gly Glu Leu Met Thr Leu Ala Thr Trp Val Gly Asn Asn Leu
                 85                  90                  95 gaa gat cca gca tca agg gat cta gta gtc agt tat gtt aat act aac     336
Glu Asp Pro Ala Ser Arg Asp Leu Val Val Ser Tyr Val Asn Thr Asn
            100                 105                 110 atg ggt tta aaa ttt agg caa cta ttg tgg ttt cat ata tct tgc ctt     384
Met Gly Leu Lys Phe Arg Gln Leu Leu Trp Phe His Ile Ser Cys Leu
        115                 120                 125 act ttt gga aga gag act gta ctt gaa tat ttg gta tct ttc gga gtg     432
Thr Phe Gly Arg Glu Thr Val Leu Glu Tyr Leu Val Ser Phe Gly Val
    130                 135                 140 tgg att cgc act cct cca gcc tat aga cca cca aat gcc cct atc tta     480
Trp Ile Arg Thr Pro Pro Ala Tyr Arg Pro Pro Asn Ala Pro Ile Leu
145                 150                 155                 160 tca aca ctt ccg gaa act act gtt gtt aac tga                          513
Ser Thr Leu Pro Glu Thr Thr Val Val Asn
                165                 170
```

<210> SEQ ID NO 4
<211> LENGTH: 170
<212> TYPE: PRT
<213> ORGANISM: Artificial Sequence
<220> FEATURE:
<223> OTHER INFORMATION: Fusion protein

<400> SEQUENCE: 4

```
Met Gly Ser Ser His His His His His His Ser Ser Gly Leu Val Pro
 1               5                  10                  15

Arg Gly Ser His Met Asp Ile Asp Pro Tyr Lys Glu Phe Gly Ala Thr
             20                  25                  30

Val Glu Leu Leu Ser Phe Leu Pro Ser Asp Phe Phe Pro Ser Val Arg
         35                  40                  45

Asp Leu Leu Asp Thr Ala Ser Ala Leu Tyr Arg Glu Ala Leu Glu Ser
     50                  55                  60

Pro Glu His Cys Ser Pro His His Thr Ala Leu Arg Gln Ala Ile Leu
 65                  70                  75                  80
```

```
Cys Trp Gly Glu Leu Met Thr Leu Ala Thr Trp Val Gly Asn Asn Leu
                85                  90                  95

Glu Asp Pro Ala Ser Arg Asp Leu Val Val Ser Tyr Val Asn Thr Asn
            100                 105                 110

Met Gly Leu Lys Phe Arg Gln Leu Leu Trp Phe His Ile Ser Cys Leu
        115                 120                 125

Thr Phe Gly Arg Glu Thr Val Leu Glu Tyr Leu Val Ser Phe Gly Val
    130                 135                 140

Trp Ile Arg Thr Pro Pro Ala Tyr Arg Pro Pro Asn Ala Pro Ile Leu
145                 150                 155                 160

Ser Thr Leu Pro Glu Thr Thr Val Val Asn
                165                 170

<210> SEQ ID NO 5
<211> LENGTH: 2241
<212> TYPE: DNA
<213> ORGANISM: Artificial Sequence
<220> FEATURE:
<221> NAME/KEY: CDS
<222> LOCATION: (1)...(2238)
<223> OTHER INFORMATION: Nucleic acids encoding fusion protein

<400> SEQUENCE: 5
```

| | | | | | | | | | | | | | | | | |
|---|---|---|---|---|---|---|---|---|---|---|---|---|---|---|---|---|
| atg ggc agc agc cat cat cat cat cac agc agc ggc ctg gtg ccg | | | | | | | | | | | | | | | | 48 |
| Met Gly Ser Ser His His His His His His Ser Ser Gly Leu Val Pro | | | | | | | | | | | | | | | | |
| 1 | | | 5 | | | | | 10 | | | | | 15 | | | |
| cgc ggc agc cat atg gac att gac cct tat aaa gaa ttt gga gct act | | | | | | | | | | | | | | | | 96 |
| Arg Gly Ser His Met Asp Ile Asp Pro Tyr Lys Glu Phe Gly Ala Thr | | | | | | | | | | | | | | | | |
| | | | 20 | | | | 25 | | | | | 30 | | | | |
| gtg gag tta ctc tcg ttt ttg cct tct gac ttc ttt cct tcc gtc aga | | | | | | | | | | | | | | | | 144 |
| Val Glu Leu Leu Ser Phe Leu Pro Ser Asp Phe Phe Pro Ser Val Arg | | | | | | | | | | | | | | | | |
| | | 35 | | | | | 40 | | | | | 45 | | | | |
| gat ctc cta gac acc gcc tca gct ctg tat cgg gaa gcc tta gag tct | | | | | | | | | | | | | | | | 192 |
| Asp Leu Leu Asp Thr Ala Ser Ala Leu Tyr Arg Glu Ala Leu Glu Ser | | | | | | | | | | | | | | | | |
| 50 | | | | 55 | | | | | 60 | | | | | | | |
| cct gag cat tgc tca cct cac cac acc gca ctc agg caa gcc att ctc | | | | | | | | | | | | | | | | 240 |
| Pro Glu His Cys Ser Pro His His Thr Ala Leu Arg Gln Ala Ile Leu | | | | | | | | | | | | | | | | |
| 65 | | | | 70 | | | | 75 | | | | | | 80 | | |
| tgc tgg ggg gaa ttg atg act cta gct acc tgg gtg ggt aat aat ttg | | | | | | | | | | | | | | | | 288 |
| Cys Trp Gly Glu Leu Met Thr Leu Ala Thr Trp Val Gly Asn Asn Leu | | | | | | | | | | | | | | | | |
| | | | | 85 | | | | | 90 | | | | | 95 | | |
| gaa gat cca gca tca agg gat cta gta gtc aat tat gtt aat act aac | | | | | | | | | | | | | | | | 336 |
| Glu Asp Pro Ala Ser Arg Asp Leu Val Val Asn Tyr Val Asn Thr Asn | | | | | | | | | | | | | | | | |
| | | | 100 | | | | | 105 | | | | | 110 | | | |
| atg ggt tta aaa ttt agg caa cta ttg tgg ttt cat ata tct tgc ctt | | | | | | | | | | | | | | | | 384 |
| Met Gly Leu Lys Phe Arg Gln Leu Leu Trp Phe His Ile Ser Cys Leu | | | | | | | | | | | | | | | | |
| | | | 115 | | | | | 120 | | | | | 125 | | | |
| act ttt gga aga gag act gta ctt gaa tat ttg gta tct ttc gga gtg | | | | | | | | | | | | | | | | 432 |
| Thr Phe Gly Arg Glu Thr Val Leu Glu Tyr Leu Val Ser Phe Gly Val | | | | | | | | | | | | | | | | |
| | | | 130 | | | | 135 | | | | | 140 | | | | |
| tgg att cgc act cct cca gcc tat aga cca cca aat gcc cct atc tta | | | | | | | | | | | | | | | | 480 |
| Trp Ile Arg Thr Pro Pro Ala Tyr Arg Pro Pro Asn Ala Pro Ile Leu | | | | | | | | | | | | | | | | |
| 145 | | | | 150 | | | | | 155 | | | | | 160 | | |
| tca aca ctt ccg gaa act act gtt gtt aga cga cgg gac cga ggc agg | | | | | | | | | | | | | | | | 528 |
| Ser Thr Leu Pro Glu Thr Thr Val Val Arg Arg Arg Asp Arg Gly Arg | | | | | | | | | | | | | | | | |
| | | | | 165 | | | | | 170 | | | | | 175 | | |
| tcc cct aga aga aga act ccc tcg cct cgc aga cga tct caa tcg | | | | | | | | | | | | | | | | 576 |
| Ser Pro Arg Arg Arg Thr Pro Ser Pro Arg Arg Arg Ser Gln Ser | | | | | | | | | | | | | | | | |
| | | | 180 | | | | | 185 | | | | | 190 | | | |
| ccg cgt cgc aga aga tct caa tct cgg gaa tct caa tgt gtt aac gcc | | | | | | | | | | | | | | | | 624 |

|   |   |   |   |   |   |   |   |   |   |   |   |   |   |   |   |   |
|---|---|---|---|---|---|---|---|---|---|---|---|---|---|---|---|---|
| Pro | Arg | Arg | Arg | Arg | Ser | Gln | Ser | Arg | Glu | Ser | Gln | Cys | Val | Asn | Ala | |
|     | 195 |     |     |     | 200 |     |     |     | 205 |     |     |     |     |     |     | |

```
aag aca att gcg tac gac gaa gag gcc cgt cgc ggc ctc gag cgg ggc       672
Lys Thr Ile Ala Tyr Asp Glu Glu Ala Arg Arg Gly Leu Glu Arg Gly
    210             215             220 ttg aac gcc ctc gcc gat gcg gta aag gtg aca ttg ggc ccc aag ggc       720
Leu Asn Ala Leu Ala Asp Ala Val Lys Val Thr Leu Gly Pro Lys Gly
225             230             235             240 cgc aac gtc gtc ctg gaa aag aag tgg ggt gcc ccc acg atc acc aac       768
Arg Asn Val Val Leu Glu Lys Lys Trp Gly Ala Pro Thr Ile Thr Asn
                245             250             255 gat ggt gtg tcc atc gcc aag gag atc gag ctg gag gat ccg tac gag       816
Asp Gly Val Ser Ile Ala Lys Glu Ile Glu Leu Glu Asp Pro Tyr Glu
            260             265             270 aag atc ggc gcc gag ctg gtc aaa gag gta gcc aag aag acc gat gac       864
Lys Ile Gly Ala Glu Leu Val Lys Glu Val Ala Lys Lys Thr Asp Asp
        275             280             285 gtc gcc ggt gac ggc acc acg acg gcc acc gtg ctg gcc cag gcg ttg       912
Val Ala Gly Asp Gly Thr Thr Thr Ala Thr Val Leu Ala Gln Ala Leu
    290             295             300 gtt cgc gag ggc ctg cgc aac gtc gcg gcc ggc gcc aac ccg ctc ggt       960
Val Arg Glu Gly Leu Arg Asn Val Ala Ala Gly Ala Asn Pro Leu Gly
305             310             315             320 ctc aaa cgc ggc atc gaa aag gcc gtg gag aag gtc acc gac acc ctg      1008
Leu Lys Arg Gly Ile Glu Lys Ala Val Glu Lys Val Thr Asp Thr Leu
                325             330             335 ctc aag ggc gcc aag gag gtc gag acc aag gag cag att gcg gcc acc      1056
Leu Lys Gly Ala Lys Glu Val Glu Thr Lys Glu Gln Ile Ala Ala Thr
            340             345             350 gca gcg att tcg gcg ggt gac cag tcc atc ggt gac ctg atc gcc gag      1104
Ala Ala Ile Ser Ala Gly Asp Gln Ser Ile Gly Asp Leu Ile Ala Glu
        355             360             365 gcg atg gac aag gtg ggc aac gag ggc gtc atc acc gtc gag gag tcc      1152
Ala Met Asp Lys Val Gly Asn Glu Gly Val Ile Thr Val Glu Glu Ser
    370             375             380 aac acc ttt ggg ctg cag ctc gag ctc acc gag ggt atg cgg ttc gac      1200
Asn Thr Phe Gly Leu Gln Leu Glu Leu Thr Glu Gly Met Arg Phe Asp
385             390             395             400 aag ggc tac atc tcg ggg tac ttc gtg acc gac ccg gag cgt cag gag      1248
Lys Gly Tyr Ile Ser Gly Tyr Phe Val Thr Asp Pro Glu Arg Gln Glu
                405             410             415 gcg gtc ctg gag gac ccc tac atc ctg ctg gtc agc tcc aag gtg tcc      1296
Ala Val Leu Glu Asp Pro Tyr Ile Leu Leu Val Ser Ser Lys Val Ser
            420             425             430 act gtc aag gat ctg ctg ccg ctg ctc gag aag gtc atc gga gcc ggt      1344
Thr Val Lys Asp Leu Leu Pro Leu Leu Glu Lys Val Ile Gly Ala Gly
        435             440             445 aag ccg ctg ctg atc atc gcc gag gac gtc gag ggc gag gcg ctg tcc      1392
Lys Pro Leu Leu Ile Ile Ala Glu Asp Val Glu Gly Glu Ala Leu Ser
    450             455             460 acc ctg gtc gtc aac aag atc cgc ggc acc ttc aag tcg gtg gcg gtc      1440
Thr Leu Val Val Asn Lys Ile Arg Gly Thr Phe Lys Ser Val Ala Val
465             470             475             480 aag gct ccc ggc ttc ggc gac cgc cgc aag gcg atg ctg cag gat atg      1488
Lys Ala Pro Gly Phe Gly Asp Arg Arg Lys Ala Met Leu Gln Asp Met
                485             490             495 gcc att ctc acc ggt ggt cag gtg atc agc gaa gag gtc ggc ctg acg      1536
Ala Ile Leu Thr Gly Gly Gln Val Ile Ser Glu Glu Val Gly Leu Thr
            500             505             510
```

```
ctg gag aac gcc gac ctg tcg ctg cta ggc aag gcc cgc aag gtc gtg       1584
Leu Glu Asn Ala Asp Leu Ser Leu Leu Gly Lys Ala Arg Lys Val Val
        515                 520                 525 gtc acc aag gac gag acc acc atc gtc gag ggc gcc ggt gac acc gac       1632
Val Thr Lys Asp Glu Thr Thr Ile Val Glu Gly Ala Gly Asp Thr Asp
    530                 535                 540 gcc atc gcc gga cga gtg gcc cag atc cgc cag gag atc gag aac agc       1680
Ala Ile Ala Gly Arg Val Ala Gln Ile Arg Gln Glu Ile Glu Asn Ser
545                 550                 555                 560 gac tcc gac tac gac cgt gag aag ctg cag gag cgg ctg gcc aag ctg       1728
Asp Ser Asp Tyr Asp Arg Glu Lys Leu Gln Glu Arg Leu Ala Lys Leu
                565                 570                 575 gcc ggt ggt gtc gcg gtg atc aag gcc ggt gcc gcc acc gag gtc gaa       1776
Ala Gly Gly Val Ala Val Ile Lys Ala Gly Ala Ala Thr Glu Val Glu
            580                 585                 590 ctc aag gag cgc aag cac cgc atc gag gat gcg gtt cgc aat gcc aag       1824
Leu Lys Glu Arg Lys His Arg Ile Glu Asp Ala Val Arg Asn Ala Lys
        595                 600                 605 gcc gcc gtc gag gag ggc atc gtc gcc ggt ggg ggt gtg acg ctg ttg       1872
Ala Ala Val Glu Glu Gly Ile Val Ala Gly Gly Gly Val Thr Leu Leu
    610                 615                 620 caa gcg gcc ccg acc ctg gac gag ctg aag ctc gaa ggc gac gag gcg       1920
Gln Ala Ala Pro Thr Leu Asp Glu Leu Lys Leu Glu Gly Asp Glu Ala
625                 630                 635                 640 acc ggc gcc aac atc gtg aag gtg gcg ctg gag gcc ccg ctg aag cag       1968
Thr Gly Ala Asn Ile Val Lys Val Ala Leu Glu Ala Pro Leu Lys Gln
                645                 650                 655 atc gcc ttc aac tcc ggg ctg gag ccg ggc gtg gtg gcc gag aag gtg       2016
Ile Ala Phe Asn Ser Gly Leu Glu Pro Gly Val Val Ala Glu Lys Val
            660                 665                 670 cgc aac ctg ccg gct ggc cac gga ctg aac gct cag acc ggt gtc tac       2064
Arg Asn Leu Pro Ala Gly His Gly Leu Asn Ala Gln Thr Gly Val Tyr
        675                 680                 685 gag gat ctg ctc gct gcc ggc gtt gct gac ccg gtc aag gtg acc cgt       2112
Glu Asp Leu Leu Ala Ala Gly Val Ala Asp Pro Val Lys Val Thr Arg
    690                 695                 700 tcg gcg ctg cag aat gcg gcg tcc atc gcg ggg ctg ttc ctg acc acc       2160
Ser Ala Leu Gln Asn Ala Ala Ser Ile Ala Gly Leu Phe Leu Thr Thr
705                 710                 715                 720 gag gcc gtc gtt gcc gac aag ccg gaa aag gag aag gct tcc gtt ccc       2208
Glu Ala Val Val Ala Asp Lys Pro Glu Lys Glu Lys Ala Ser Val Pro
                725                 730                 735 ggt ggc ggc gac atg ggt ggc atg gat ttc tga                           2241
Gly Gly Gly Asp Met Gly Gly Met Asp Phe
            740                 745
```

<210> SEQ ID NO 6
<211> LENGTH: 746
<212> TYPE: PRT
<213> ORGANISM: Artificial Sequence
<220> FEATURE:
<223> OTHER INFORMATION: Fusion protein

<400> SEQUENCE: 6

```
Met Gly Ser Ser His His His His His His Ser Ser Gly Leu Val Pro
1               5                   10                  15

Arg Gly Ser His Met Asp Ile Asp Pro Tyr Lys Glu Phe Gly Ala Thr
            20                  25                  30

Val Glu Leu Leu Ser Phe Leu Pro Ser Asp Phe Phe Pro Ser Val Arg
        35                  40                  45
```

-continued

```
Asp Leu Leu Asp Thr Ala Ser Ala Leu Tyr Arg Glu Ala Leu Glu Ser
     50                  55                  60
Pro Glu His Cys Ser Pro His His Thr Ala Leu Arg Gln Ala Ile Leu
 65                  70                  75                  80
Cys Trp Gly Glu Leu Met Thr Leu Ala Thr Trp Val Gly Asn Asn Leu
                 85                  90                  95
Glu Asp Pro Ala Ser Arg Asp Leu Val Val Asn Tyr Val Asn Thr Asn
            100                 105                 110
Met Gly Leu Lys Phe Arg Gln Leu Leu Trp Phe His Ile Ser Cys Leu
        115                 120                 125
Thr Phe Gly Arg Glu Thr Val Leu Glu Tyr Leu Val Ser Phe Gly Val
    130                 135                 140
Trp Ile Arg Thr Pro Pro Ala Tyr Arg Pro Pro Asn Ala Pro Ile Leu
145                 150                 155                 160
Ser Thr Leu Pro Glu Thr Thr Val Val Arg Arg Asp Arg Gly Arg
                165                 170                 175
Ser Pro Arg Arg Arg Thr Pro Ser Pro Arg Arg Arg Ser Gln Ser
            180                 185                 190
Pro Arg Arg Arg Arg Ser Gln Ser Arg Glu Ser Gln Cys Val Asn Ala
    195                 200                 205
Lys Thr Ile Ala Tyr Asp Glu Glu Ala Arg Arg Gly Leu Glu Arg Gly
    210                 215                 220
Leu Asn Ala Leu Ala Asp Ala Val Lys Val Thr Leu Gly Pro Lys Gly
225                 230                 235                 240
Arg Asn Val Val Leu Glu Lys Lys Trp Gly Ala Pro Thr Ile Thr Asn
                245                 250                 255
Asp Gly Val Ser Ile Ala Lys Glu Ile Glu Leu Glu Asp Pro Tyr Glu
            260                 265                 270
Lys Ile Gly Ala Glu Leu Val Lys Glu Val Ala Lys Lys Thr Asp Asp
        275                 280                 285
Val Ala Gly Asp Gly Thr Thr Thr Ala Thr Val Leu Ala Gln Ala Leu
    290                 295                 300
Val Arg Glu Gly Leu Arg Asn Val Ala Ala Gly Ala Asn Pro Leu Gly
305                 310                 315                 320
Leu Lys Arg Gly Ile Glu Lys Ala Val Glu Lys Val Thr Asp Thr Leu
                325                 330                 335
Leu Lys Gly Ala Lys Glu Val Glu Thr Lys Glu Gln Ile Ala Ala Thr
            340                 345                 350
Ala Ala Ile Ser Ala Gly Asp Gln Ser Ile Gly Asp Leu Ile Ala Glu
        355                 360                 365
Ala Met Asp Lys Val Gly Asn Glu Gly Val Ile Thr Val Glu Glu Ser
    370                 375                 380
Asn Thr Phe Gly Leu Gln Leu Glu Leu Thr Glu Gly Met Arg Phe Asp
385                 390                 395                 400
Lys Gly Tyr Ile Ser Gly Tyr Phe Val Thr Asp Pro Glu Arg Gln Glu
                405                 410                 415
Ala Val Leu Glu Asp Pro Tyr Ile Leu Val Ser Ser Lys Val Ser
            420                 425                 430
Thr Val Lys Asp Leu Leu Pro Leu Leu Glu Lys Val Ile Gly Ala Gly
        435                 440                 445
Lys Pro Leu Leu Ile Ile Ala Glu Asp Val Glu Gly Glu Ala Leu Ser
    450                 455                 460
Thr Leu Val Val Asn Lys Ile Arg Gly Thr Phe Lys Ser Val Ala Val
```

```
                         465                 470                 475                 480
                    Lys Ala Pro Gly Phe Gly Asp Arg Arg Lys Ala Met Leu Gln Asp Met
                                     485                 490                 495

Ala Ile Leu Thr Gly Gly Gln Val Ile Ser Glu Glu Val Gly Leu Thr
                                 500                 505                 510

Leu Glu Asn Ala Asp Leu Ser Leu Leu Gly Lys Ala Arg Lys Val Val
                                 515                 520                 525

Val Thr Lys Asp Glu Thr Thr Ile Val Glu Gly Ala Gly Asp Thr Asp
                            530                 535                 540

Ala Ile Ala Gly Arg Val Ala Gln Ile Arg Gln Glu Ile Glu Asn Ser
                    545                 550                 555                 560

Asp Ser Asp Tyr Asp Arg Glu Lys Leu Gln Glu Arg Leu Ala Lys Leu
                                     565                 570                 575

Ala Gly Gly Val Ala Val Ile Lys Ala Gly Ala Ala Thr Glu Val Glu
                                 580                 585                 590

Leu Lys Glu Arg Lys His Arg Ile Glu Asp Ala Val Arg Asn Ala Lys
                                 595                 600                 605

Ala Ala Val Glu Glu Gly Ile Val Ala Gly Gly Val Thr Leu Leu
                            610                 615                 620

Gln Ala Ala Pro Thr Leu Asp Glu Leu Lys Leu Glu Gly Asp Glu Ala
                    625                 630                 635                 640

Thr Gly Ala Asn Ile Val Lys Val Ala Leu Glu Ala Pro Leu Lys Gln
                                     645                 650                 655

Ile Ala Phe Asn Ser Gly Leu Glu Pro Gly Val Val Ala Glu Lys Val
                                 660                 665                 670

Arg Asn Leu Pro Ala Gly His Gly Leu Asn Ala Gln Thr Gly Val Tyr
                                 675                 680                 685

Glu Asp Leu Leu Ala Ala Gly Val Ala Asp Pro Val Lys Val Thr Arg
                            690                 695                 700

Ser Ala Leu Gln Asn Ala Ala Ser Ile Ala Gly Leu Phe Leu Thr Thr
                    705                 710                 715                 720

Glu Ala Val Val Ala Asp Lys Pro Glu Lys Glu Lys Ala Ser Val Pro
                                     725                 730                 735

Gly Gly Gly Asp Met Gly Gly Met Asp Phe
                                 740                 745

<210> SEQ ID NO 7
<211> LENGTH: 2130
<212> TYPE: DNA
<213> ORGANISM: Artificial Sequence
<220> FEATURE:
<221> NAME/KEY: CDS
<222> LOCATION: (1)...(2127)
<223> OTHER INFORMATION: Nucleic acids encoding fusion protein

<400> SEQUENCE: 7 atg ggc agc agc cat cat cat cat cat cac agc agc ggc ctg gtg ccg        48
Met Gly Ser Ser His His His His His His Ser Ser Gly Leu Val Pro
 1               5                  10                  15 cgc ggc agc cat atg gac att gac cct tat aaa gaa ttt gga gct act        96
Arg Gly Ser His Met Asp Ile Asp Pro Tyr Lys Glu Phe Gly Ala Thr
             20                  25                  30 gtg gag tta ctc tcg ttt ttg cct tct gac ttc ttt cct tcc gtc aga       144
Val Glu Leu Leu Ser Phe Leu Pro Ser Asp Phe Phe Pro Ser Val Arg
         35                  40                  45 gat ctc cta gac acc gcc tca gct ctg tat cgg gaa gcc tta gag tct       192
Asp Leu Leu Asp Thr Ala Ser Ala Leu Tyr Arg Glu Ala Leu Glu Ser
```

```
                 50                      55                      60
cct gag cat tgc tca cct cac cac acc gca ctc agg caa gcc att ctc     240
Pro Glu His Cys Ser Pro His His Thr Ala Leu Arg Gln Ala Ile Leu
 65                  70                      75                  80 tgc tgg ggg gaa ttg atg act cta gct acc tgg gtg ggt aat aat ttg     288
Cys Trp Gly Glu Leu Met Thr Leu Ala Thr Trp Val Gly Asn Asn Leu
                         85                      90                  95 gaa gat cca gca tca agg gat cta gta gtc agt tat gtt aat act aac     336
Glu Asp Pro Ala Ser Arg Asp Leu Val Val Ser Tyr Val Asn Thr Asn
                     100                     105                     110 atg ggt tta aaa ttt agg caa cta ttg tgg ttt cat ata tct tgc ctt     384
Met Gly Leu Lys Phe Arg Gln Leu Leu Trp Phe His Ile Ser Cys Leu
                 115                     120                     125 act ttt gga aga gag act gta ctt gaa tat ttg gta tct ttc gga gtg     432
Thr Phe Gly Arg Glu Thr Val Leu Glu Tyr Leu Val Ser Phe Gly Val
130                     135                     140 tgg att cgc act cct cca gcc tat aga cca cca aat gcc cct atc tta     480
Trp Ile Arg Thr Pro Pro Ala Tyr Arg Pro Pro Asn Ala Pro Ile Leu
145                     150                     155                     160 tca aca ctt ccg gaa act act gtt gtt aac gcc aag aca att gcg tac     528
Ser Thr Leu Pro Glu Thr Thr Val Val Asn Ala Lys Thr Ile Ala Tyr
                 165                     170                     175 gac gaa gag gcc cgt cgc ggc ctc gag cgg ggc ttg aac gcc ctc gcc     576
Asp Glu Glu Ala Arg Arg Gly Leu Glu Arg Gly Leu Asn Ala Leu Ala
             180                     185                     190 gat gcg gta aag gtg aca ttg ggc ccc aag ggc cgc aac gtc gtc ctg     624
Asp Ala Val Lys Val Thr Leu Gly Pro Lys Gly Arg Asn Val Val Leu
         195                     200                     205 gaa aag aag tgg ggt gcc ccc acg atc acc aac gat ggt gtg tcc atc     672
Glu Lys Lys Trp Gly Ala Pro Thr Ile Thr Asn Asp Gly Val Ser Ile
     210                     215                     220 gcc aag gag atc gag ctg gag gat ccg tac gag aag atc ggc gcc gag     720
Ala Lys Glu Ile Glu Leu Glu Asp Pro Tyr Glu Lys Ile Gly Ala Glu
225                     230                     235                     240 ctg gtc aaa gag gta gcc aag aag acc gat gac gtc gcc ggt gac ggc     768
Leu Val Lys Glu Val Ala Lys Lys Thr Asp Asp Val Ala Gly Asp Gly
                 245                     250                     255 acc acg acg gcc acc gtg ctg gcc cag gcg ttg gtt cgc gag ggc ctg     816
Thr Thr Thr Ala Thr Val Leu Ala Gln Ala Leu Val Arg Glu Gly Leu
             260                     265                     270 cgc aac gtc gcg gcc ggc gcc aac ccg ctc ggt ctc aaa cgc ggc atc     864
Arg Asn Val Ala Ala Gly Ala Asn Pro Leu Gly Leu Lys Arg Gly Ile
         275                     280                     285 gaa aag gcc gtg gag aag gtc acc gag acc ctg ctc aag ggc gcc aag     912
Glu Lys Ala Val Glu Lys Val Thr Glu Thr Leu Leu Lys Gly Ala Lys
     290                     295                     300 gag gtc gag acc aag gag cag att gcg gcc acc gca gcg att tcg gcg     960
Glu Val Glu Thr Lys Glu Gln Ile Ala Ala Thr Ala Ala Ile Ser Ala
305                     310                     315                     320 ggt gac cag tcc atc ggt gac ctg atc gcc gag gcg atg gac aag gtg    1008
Gly Asp Gln Ser Ile Gly Asp Leu Ile Ala Glu Ala Met Asp Lys Val
                 325                     330                     335 ggc aac gag ggc gtc atc acc gtc gag gag tcc aac acc ttt ggg ctg    1056
Gly Asn Glu Gly Val Ile Thr Val Glu Glu Ser Asn Thr Phe Gly Leu
             340                     345                     350 cag ctc gag ctc acc gag ggt atg cgg ttc gac aag ggc tac atc tcg    1104
Gln Leu Glu Leu Thr Glu Gly Met Arg Phe Asp Lys Gly Tyr Ile Ser
         355                     360                     365 ggg tac ttc gtg acc gac ccg gag cgt cag gag gcg gtc ctg gag gac    1152
Gly Tyr Phe Val Thr Asp Pro Glu Arg Gln Glu Ala Val Leu Glu Asp
```

```
                                                                -continued

Gly Tyr Phe Val Thr Asp Pro Glu Arg Gln Glu Ala Val Leu Glu Asp
    370                 375                 380 ccc tac atc ctg ctg gtc agc tcc aag gtg tcc act gtc aag gat ctg        1200
Pro Tyr Ile Leu Leu Val Ser Ser Lys Val Ser Thr Val Lys Asp Leu
385                 390                 395                 400 ctg ccg ctg ctc gag aag gtc atc gga gcc ggt aag ccg ctg ctg atc        1248
Leu Pro Leu Leu Glu Lys Val Ile Gly Ala Gly Lys Pro Leu Leu Ile
                405                 410                 415 atc gcc gag gac gtc gag ggc gag gcg ctg tcc acc ctg gtc gtc aac        1296
Ile Ala Glu Asp Val Glu Gly Glu Ala Leu Ser Thr Leu Val Val Asn
            420                 425                 430 aag atc cgc ggc acc ttc aag tcg gtg gcg gtc aag gct ccc ggc ttc        1344
Lys Ile Arg Gly Thr Phe Lys Ser Val Ala Val Lys Ala Pro Gly Phe
        435                 440                 445 ggc gac cgc cgc aag gcg atg ctg cag gat atg gcc att ctc acc ggt        1392
Gly Asp Arg Arg Lys Ala Met Leu Gln Asp Met Ala Ile Leu Thr Gly
    450                 455                 460 ggt cag gtg atc agc gaa gag gtc ggc ctg acg ctg gag aac gcc gac        1440
Gly Gln Val Ile Ser Glu Glu Val Gly Leu Thr Leu Glu Asn Ala Asp
465                 470                 475                 480 ctg tcg ctg cta ggc aag gcc cgc aag gtc gtg gtc acc aag gac gag        1488
Leu Ser Leu Leu Gly Lys Ala Arg Lys Val Val Val Thr Lys Asp Glu
                485                 490                 495 acc acc atc gtc gag ggc gcc ggt gac acc gac gcc atc gcc gga cga        1536
Thr Thr Ile Val Glu Gly Ala Gly Asp Thr Asp Ala Ile Ala Gly Arg
            500                 505                 510 gtg gcc cag atc cgc cag gag atc gag aac agc gac tcc gac tac gac        1584
Val Ala Gln Ile Arg Gln Glu Ile Glu Asn Ser Asp Ser Asp Tyr Asp
        515                 520                 525 cgt gag aag ctg cag gag cgg ctg gcc aag ctg gcc ggt ggt gtc gcg        1632
Arg Glu Lys Leu Gln Glu Arg Leu Ala Lys Leu Ala Gly Gly Val Ala
    530                 535                 540 gtg atc aag gcc ggt gcc gcc acc gag gtc gaa ctc aag gag cgc aag        1680
Val Ile Lys Ala Gly Ala Ala Thr Glu Val Glu Leu Lys Glu Arg Lys
545                 550                 555                 560 cac cgc atc gag gat gcg gtt cgc aat gcc aag gcc gcc gtc gag gag        1728
His Arg Ile Glu Asp Ala Val Arg Asn Ala Lys Ala Ala Val Glu Glu
                565                 570                 575 ggc atc gtc gcc ggt ggg ggt gtg acg ctg ttg caa gcg gcc ccg acc        1776
Gly Ile Val Ala Gly Gly Gly Val Thr Leu Leu Gln Ala Ala Pro Thr
            580                 585                 590 ctg gac gag ctg aag ctc gaa ggc gac gag gcg acc ggc gcc aac atc        1824
Leu Asp Glu Leu Lys Leu Glu Gly Asp Glu Ala Thr Gly Ala Asn Ile
        595                 600                 605 gtg aag gtg gcg ctg gag gcc ccg ctg aag cag atc gcc ttc aac tcc        1872
Val Lys Val Ala Leu Glu Ala Pro Leu Lys Gln Ile Ala Phe Asn Ser
    610                 615                 620 ggg ctg gag ccg ggc gtg gtg gcc gag aag gtg cgc aac ctg ccg gct        1920
Gly Leu Glu Pro Gly Val Val Ala Glu Lys Val Arg Asn Leu Pro Ala
625                 630                 635                 640 ggc cac gga ctg aac gct cag acc ggt gtc tac gag gat ctg ctc gct        1968
Gly His Gly Leu Asn Ala Gln Thr Gly Val Tyr Glu Asp Leu Leu Ala
                645                 650                 655 gcc ggc gtt gct gac ccg gtc aag gtg acc cgt tcg gcg ctg cag aat        2016
Ala Gly Val Ala Asp Pro Val Lys Val Thr Arg Ser Ala Leu Gln Asn
            660                 665                 670 gcg gcg tcc atc gcg ggg ctg ttc ctg acc acc gag gcc gtc gtt gcc        2064
Ala Ala Ser Ile Ala Gly Leu Phe Leu Thr Thr Glu Ala Val Val Ala
        675                 680                 685
```

```
gac aag ccg gaa aag gag aag gct tcc gtt ccc ggt ggc ggc gac atg      2112
Asp Lys Pro Glu Lys Glu Lys Ala Ser Val Pro Gly Gly Gly Asp Met
    690             695                 700 ggt ggc atg gat ttc tga                                              2130
Gly Gly Met Asp Phe
705

<210> SEQ ID NO 8
<211> LENGTH: 709
<212> TYPE: PRT
<213> ORGANISM: Artificial Sequence
<220> FEATURE:
<223> OTHER INFORMATION: Fusion protein

<400> SEQUENCE: 8

Met Gly Ser Ser His His His His His Ser Ser Gly Leu Val Pro
 1               5                  10                  15

Arg Gly Ser His Met Asp Ile Asp Pro Tyr Lys Glu Phe Gly Ala Thr
                 20                  25                  30

Val Glu Leu Leu Ser Phe Leu Pro Ser Asp Phe Phe Pro Ser Val Arg
             35                  40                  45

Asp Leu Leu Asp Thr Ala Ser Ala Leu Tyr Arg Glu Ala Leu Glu Ser
         50                  55                  60

Pro Glu His Cys Ser Pro His His Thr Ala Leu Arg Gln Ala Ile Leu
 65                  70                  75                  80

Cys Trp Gly Glu Leu Met Thr Leu Ala Thr Trp Val Gly Asn Asn Leu
                 85                  90                  95

Glu Asp Pro Ala Ser Arg Asp Leu Val Val Ser Tyr Val Asn Thr Asn
            100                 105                 110

Met Gly Leu Lys Phe Arg Gln Leu Leu Trp Phe His Ile Ser Cys Leu
            115                 120                 125

Thr Phe Gly Arg Glu Thr Val Leu Glu Tyr Leu Val Ser Phe Gly Val
        130                 135                 140

Trp Ile Arg Thr Pro Pro Ala Tyr Arg Pro Pro Asn Ala Pro Ile Leu
145                 150                 155                 160

Ser Thr Leu Pro Glu Thr Thr Val Val Asn Ala Lys Thr Ile Ala Tyr
                165                 170                 175

Asp Glu Glu Ala Arg Arg Gly Leu Glu Arg Gly Leu Asn Ala Leu Ala
            180                 185                 190

Asp Ala Val Lys Val Thr Leu Gly Pro Lys Gly Arg Asn Val Val Leu
        195                 200                 205

Glu Lys Lys Trp Gly Ala Pro Thr Ile Thr Asn Asp Gly Val Ser Ile
    210                 215                 220

Ala Lys Glu Ile Glu Leu Glu Asp Pro Tyr Glu Lys Ile Gly Ala Glu
225                 230                 235                 240

Leu Val Lys Glu Val Ala Lys Lys Thr Asp Asp Val Ala Gly Asp Gly
                245                 250                 255

Thr Thr Thr Ala Thr Val Leu Ala Gln Ala Leu Val Arg Glu Gly Leu
            260                 265                 270

Arg Asn Val Ala Ala Gly Ala Asn Pro Leu Gly Leu Lys Arg Gly Ile
        275                 280                 285

Glu Lys Ala Val Glu Lys Val Thr Glu Thr Leu Leu Lys Gly Ala Lys
    290                 295                 300

Glu Val Glu Thr Lys Glu Gln Ile Ala Ala Thr Ala Ala Ile Ser Ala
305                 310                 315                 320

Gly Asp Gln Ser Ile Gly Asp Leu Ile Ala Glu Ala Met Asp Lys Val
```

325                 330                 335
Gly Asn Glu Gly Val Ile Thr Val Glu Ser Asn Thr Phe Gly Leu
            340                 345                 350
Gln Leu Glu Leu Thr Glu Gly Met Arg Phe Asp Lys Gly Tyr Ile Ser
        355                 360                 365
Gly Tyr Phe Val Thr Asp Pro Glu Arg Gln Glu Ala Val Leu Glu Asp
        370                 375                 380
Pro Tyr Ile Leu Leu Val Ser Ser Lys Val Ser Thr Val Lys Asp Leu
385                 390                 395                 400
Leu Pro Leu Leu Glu Lys Val Ile Gly Ala Gly Lys Pro Leu Leu Ile
            405                 410                 415
Ile Ala Glu Asp Val Glu Gly Glu Ala Leu Ser Thr Leu Val Val Asn
            420                 425                 430
Lys Ile Arg Gly Thr Phe Lys Ser Val Ala Val Lys Ala Pro Gly Phe
        435                 440                 445
Gly Asp Arg Arg Lys Ala Met Leu Gln Asp Met Ala Ile Leu Thr Gly
        450                 455                 460
Gly Gln Val Ile Ser Glu Glu Val Gly Leu Thr Leu Glu Asn Ala Asp
465                 470                 475                 480
Leu Ser Leu Leu Gly Lys Ala Arg Lys Val Val Thr Lys Asp Glu
            485                 490                 495
Thr Thr Ile Val Glu Gly Ala Gly Asp Thr Asp Ala Ile Ala Gly Arg
            500                 505                 510
Val Ala Gln Ile Arg Gln Glu Ile Glu Asn Ser Asp Ser Asp Tyr Asp
        515                 520                 525
Arg Glu Lys Leu Gln Glu Arg Leu Ala Lys Leu Ala Gly Gly Val Ala
        530                 535                 540
Val Ile Lys Ala Gly Ala Ala Thr Glu Val Glu Leu Lys Glu Arg Lys
545                 550                 555                 560
His Arg Ile Glu Asp Ala Val Arg Asn Ala Lys Ala Ala Val Glu Glu
            565                 570                 575
Gly Ile Val Ala Gly Gly Gly Val Thr Leu Leu Gln Ala Ala Pro Thr
            580                 585                 590
Leu Asp Glu Leu Lys Leu Glu Gly Asp Glu Ala Thr Gly Ala Asn Ile
        595                 600                 605
Val Lys Val Ala Leu Glu Ala Pro Leu Lys Gln Ile Ala Phe Asn Ser
        610                 615                 620
Gly Leu Glu Pro Gly Val Val Ala Glu Lys Val Arg Asn Leu Pro Ala
625                 630                 635                 640
Gly His Gly Leu Asn Ala Gln Thr Gly Val Tyr Glu Asp Leu Leu Ala
            645                 650                 655
Ala Gly Val Ala Asp Pro Val Lys Val Thr Arg Ser Ala Leu Gln Asn
            660                 665                 670
Ala Ala Ser Ile Ala Gly Leu Phe Leu Thr Thr Glu Ala Val Val Ala
        675                 680                 685
Asp Lys Pro Glu Lys Glu Lys Ala Ser Val Pro Gly Gly Gly Asp Met
        690                 695                 700
Gly Gly Met Asp Phe
705

<210> SEQ ID NO 9
<211> LENGTH: 2073
<212> TYPE: DNA
<213> ORGANISM: Artificial Sequence

```
<220> FEATURE:
<221> NAME/KEY: CDS
<222> LOCATION: (1)...(2070)
<223> OTHER INFORMATION: Nucleic acids encoding fusion protein

<400> SEQUENCE: 9 atg gac att gac cct tat aaa gaa ttt gga gct act gtg gag tta ctc        48
Met Asp Ile Asp Pro Tyr Lys Glu Phe Gly Ala Thr Val Glu Leu Leu
 1               5                  10                  15 tcg ttt ttg cct tct gac ttc ttt cct tcc gtc aga gat ctc cta gac        96
Ser Phe Leu Pro Ser Asp Phe Phe Pro Ser Val Arg Asp Leu Leu Asp
             20                  25                  30 acc gcc tca gct ctg tat cgg gaa gcc tta gag tct cct gag cat tgc       144
Thr Ala Ser Ala Leu Tyr Arg Glu Ala Leu Glu Ser Pro Glu His Cys
         35                  40                  45 tca cct cac cac acc gca ctc agg caa gcc att ctc tgc tgg ggg gaa       192
Ser Pro His His Thr Ala Leu Arg Gln Ala Ile Leu Cys Trp Gly Glu
     50                  55                  60 ttg atg act cta gct acc tgg gtg ggt aat aat ttg gaa gat cca gca       240
Leu Met Thr Leu Ala Thr Trp Val Gly Asn Asn Leu Glu Asp Pro Ala
 65                  70                  75                  80 tca agg gat cta gta gtc aat tat gtt aat act aac atg ggt tta aaa       288
Ser Arg Asp Leu Val Val Asn Tyr Val Asn Thr Asn Met Gly Leu Lys
                 85                  90                  95 ttt agg caa cta ttg tgg ttt cat ata tct tgc ctt act ttt gga aga       336
Phe Arg Gln Leu Leu Trp Phe His Ile Ser Cys Leu Thr Phe Gly Arg
            100                 105                 110 gag act gta ctt gaa tat ttg gta tct ttc gga gtg tgg att cgc act       384
Glu Thr Val Leu Glu Tyr Leu Val Ser Phe Gly Val Trp Ile Arg Thr
        115                 120                 125 cct cca gcc tat aga cca cca aat gcc cct atc tta tca aca ctt ccg       432
Pro Pro Ala Tyr Arg Pro Pro Asn Ala Pro Ile Leu Ser Thr Leu Pro
    130                 135                 140 gaa act act gtt gtt aga cga gcc aag aca att gcg tac gac gaa gag       480
Glu Thr Thr Val Val Arg Arg Ala Lys Thr Ile Ala Tyr Asp Glu Glu
145                 150                 155                 160 gcc cgt cgc ggc ctc gag cgg ggc ttg aac gcc ctc gcc gat gcg gta       528
Ala Arg Arg Gly Leu Glu Arg Gly Leu Asn Ala Leu Ala Asp Ala Val
                165                 170                 175 aag gtg aca ttg ggc ccc aag ggc cgc aac gtc gtc ctg gaa aag aag       576
Lys Val Thr Leu Gly Pro Lys Gly Arg Asn Val Val Leu Glu Lys Lys
            180                 185                 190 tgg ggt gcc ccc acg atc acc aac gat ggt gtg tcc atc gcc aag gag       624
Trp Gly Ala Pro Thr Ile Thr Asn Asp Gly Val Ser Ile Ala Lys Glu
        195                 200                 205 atc gag ctg gag gat ccg tac gag aag atc ggc gcc gag ctg gtc aaa       672
Ile Glu Leu Glu Asp Pro Tyr Glu Lys Ile Gly Ala Glu Leu Val Lys
    210                 215                 220 gag gta gcc aag aag acc gat gac gtc gcc ggt gac ggc acc acg acg       720
Glu Val Ala Lys Lys Thr Asp Asp Val Ala Gly Asp Gly Thr Thr Thr
225                 230                 235                 240 gcc acc gtg ctg gcc cag gcg ttg gtt cgc gag ggc ctg cgc aac gtc       768
Ala Thr Val Leu Ala Gln Ala Leu Val Arg Glu Gly Leu Arg Asn Val
                245                 250                 255 gcg gcc ggc gcc aac ccg ctc ggt ctc aaa cgc ggc atc gaa aag gcc       816
Ala Ala Gly Ala Asn Pro Leu Gly Leu Lys Arg Gly Ile Glu Lys Ala
            260                 265                 270 gtg gag aag gtc acc gag acc ctg ctc aag ggc gcc aag gag gtc gag       864
Val Glu Lys Val Thr Glu Thr Leu Leu Lys Gly Ala Lys Glu Val Glu
        275                 280                 285
```

```
acc aag gag cag att gcg gcc acc gca gcg att tcg gcg ggt gac cag      912
Thr Lys Glu Gln Ile Ala Ala Thr Ala Ala Ile Ser Ala Gly Asp Gln
    290                 295                 300 tcc atc ggt gac ctg atc gcc gag gcg atg gac aag gtg ggc aac gag      960
Ser Ile Gly Asp Leu Ile Ala Glu Ala Met Asp Lys Val Gly Asn Glu
305                 310                 315                 320 ggc gtc atc acc gtc gag gag tcc aac acc ttt ggg ctg cag ctc gag     1008
Gly Val Ile Thr Val Glu Glu Ser Asn Thr Phe Gly Leu Gln Leu Glu
                325                 330                 335 ctc acc gag ggt atg cgg ttc gac aag ggc tac atc tcg ggg tac ttc     1056
Leu Thr Glu Gly Met Arg Phe Asp Lys Gly Tyr Ile Ser Gly Tyr Phe
            340                 345                 350 gtg acc gac ccg gag cgt cag gag gcg gtc ctg gag gac ccc tac atc     1104
Val Thr Asp Pro Glu Arg Gln Glu Ala Val Leu Glu Asp Pro Tyr Ile
        355                 360                 365 ctg ctg gtc agc tcc aag gtg tcc act gtc aag gat ctg ctg ccg ctg     1152
Leu Leu Val Ser Ser Lys Val Ser Thr Val Lys Asp Leu Leu Pro Leu
370                 375                 380 ctc gag aag gtc atc gga gcc ggt aag ccg ctg ctc atc atc gcc gag     1200
Leu Glu Lys Val Ile Gly Ala Gly Lys Pro Leu Leu Ile Ile Ala Glu
385                 390                 395                 400 gac gtc gag ggc gag gcg ctg tcc acc ctg gtc gtc aac aag atc cgc     1248
Asp Val Glu Gly Glu Ala Leu Ser Thr Leu Val Val Asn Lys Ile Arg
                405                 410                 415 ggc acc ttc aag tcg gtg gcg gtc aag gct ccc ggc ttc ggc gac cgc     1296
Gly Thr Phe Lys Ser Val Ala Val Lys Ala Pro Gly Phe Gly Asp Arg
            420                 425                 430 cgc aag gcg atg ctg cag gat atg gcc att ctc acc ggt ggt cag gtg     1344
Arg Lys Ala Met Leu Gln Asp Met Ala Ile Leu Thr Gly Gly Gln Val
        435                 440                 445 atc agc gaa gag gtc ggc ctg acg ctg gag aac gcc gac ctg tcg ctg     1392
Ile Ser Glu Glu Val Gly Leu Thr Leu Glu Asn Ala Asp Leu Ser Leu
450                 455                 460 cta ggc aag gcc cgc aag gtc gtg gtc acc aag gac gag acc acc atc     1440
Leu Gly Lys Ala Arg Lys Val Val Val Thr Lys Asp Glu Thr Thr Ile
465                 470                 475                 480 gtc gag ggc gcc ggt gac acc gac gcc atc gcc gga cga gtg gcc cag     1488
Val Glu Gly Ala Gly Asp Thr Asp Ala Ile Ala Gly Arg Val Ala Gln
                485                 490                 495 atc cgc cag gag atc gag aac agc gac tcc gac tac gac cgt gag aag     1536
Ile Arg Gln Glu Ile Glu Asn Ser Asp Ser Asp Tyr Asp Arg Glu Lys
            500                 505                 510 ctg cag gag cgg ctg gcc aag ctg gcc ggt ggt gtc gcg gtg atc aag     1584
Leu Gln Glu Arg Leu Ala Lys Leu Ala Gly Gly Val Ala Val Ile Lys
        515                 520                 525 gcc ggt gcc gcc acc gag gtc gaa ctc aag gag cgc aag cac cgc atc     1632
Ala Gly Ala Ala Thr Glu Val Glu Leu Lys Glu Arg Lys His Arg Ile
530                 535                 540 gag gat gcg gtt cgc aat gcc aag gcc gcc gtc gag gag ggc atc gtc     1680
Glu Asp Ala Val Arg Asn Ala Lys Ala Ala Val Glu Glu Gly Ile Val
545                 550                 555                 560 gcc ggt ggg ggt gtg acg ctg ttg caa gcg gcc ccg acc ctg gac gag     1728
Ala Gly Gly Gly Val Thr Leu Leu Gln Ala Ala Pro Thr Leu Asp Glu
                565                 570                 575 ctg aag ctc gaa ggc gac gag gcg acc ggc gcc aac atc gtg aag gtg     1776
Leu Lys Leu Glu Gly Asp Glu Ala Thr Gly Ala Asn Ile Val Lys Val
            580                 585                 590 gcg ctg gag gcc ccg ctg aag cag atc gcc ttc aac tcc ggg ctg gag     1824
Ala Leu Glu Ala Pro Leu Lys Gln Ile Ala Phe Asn Ser Gly Leu Glu
        595                 600                 605
```

```
ccg ggc gtg gtg gcc gag aag gtg cgc aac ctg ccg gct ggc cac gga        1872
Pro Gly Val Val Ala Glu Lys Val Arg Asn Leu Pro Ala Gly His Gly
610                 615                 620 ctg aac gct cag acc ggt gtc tac gag gat ctg ctc gct gcc ggc gtt        1920
Leu Asn Ala Gln Thr Gly Val Tyr Glu Asp Leu Leu Ala Ala Gly Val
625                 630                 635                 640 gct gac ccg gtc aag gtg acc cgt tcg gcg ctg cag aat gcg gcg tcc        1968
Ala Asp Pro Val Lys Val Thr Arg Ser Ala Leu Gln Asn Ala Ala Ser
                645                 650                 655 atc gcg ggg ctg ttc ctg acc acc gag gcc gtc gtt gcc gac aag ccg        2016
Ile Ala Gly Leu Phe Leu Thr Thr Glu Ala Val Val Ala Asp Lys Pro
            660                 665                 670 gaa aag gag aag gct tcc gtt ccc ggt ggc ggc gac atg ggt ggc atg        2064
Glu Lys Glu Lys Ala Ser Val Pro Gly Gly Gly Asp Met Gly Gly Met
        675                 680                 685 gat ttc tga                                                             2073
Asp Phe
    690

<210> SEQ ID NO 10
<211> LENGTH: 690
<212> TYPE: PRT
<213> ORGANISM: Artificial Sequence
<220> FEATURE:
<223> OTHER INFORMATION: Fusion protein

<400> SEQUENCE: 10

Met Asp Ile Asp Pro Tyr Lys Glu Phe Gly Ala Thr Val Glu Leu Leu
  1               5                  10                  15

Ser Phe Leu Pro Ser Asp Phe Pro Ser Val Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Val Val Arg Arg Ala Lys Thr Ile Ala Tyr Asp Glu Glu
145                 150                 155                 160

Ala Arg Arg Gly Leu Glu Arg Gly Leu Asn Ala Leu Ala Asp Ala Val
                165                 170                 175

Lys Val Thr Leu Gly Pro Lys Gly Arg Asn Val Leu Glu Lys Lys
            180                 185                 190

Trp Gly Ala Pro Thr Ile Thr Asn Asp Gly Val Ser Ile Ala Lys Glu
        195                 200                 205

Ile Glu Leu Glu Asp Pro Tyr Glu Lys Ile Gly Ala Glu Leu Val Lys
    210                 215                 220

Glu Val Ala Lys Lys Thr Asp Asp Val Ala Gly Asp Gly Thr Thr Thr
225                 230                 235                 240
```

-continued

```
Ala Thr Val Leu Ala Gln Ala Leu Val Arg Glu Gly Leu Arg Asn Val
                245                 250                 255

Ala Ala Gly Ala Asn Pro Leu Gly Leu Lys Arg Gly Ile Glu Lys Ala
            260                 265                 270

Val Glu Lys Val Thr Glu Thr Leu Leu Lys Gly Ala Lys Glu Val Glu
        275                 280                 285

Thr Lys Glu Gln Ile Ala Ala Thr Ala Ala Ile Ser Ala Gly Asp Gln
    290                 295                 300

Ser Ile Gly Asp Leu Ile Ala Glu Ala Met Asp Lys Val Gly Asn Glu
305                 310                 315                 320

Gly Val Ile Thr Val Glu Glu Ser Asn Thr Phe Gly Leu Gln Leu Glu
                325                 330                 335

Leu Thr Glu Gly Met Arg Phe Asp Lys Gly Tyr Ile Ser Gly Tyr Phe
            340                 345                 350

Val Thr Asp Pro Glu Arg Gln Glu Ala Val Leu Glu Asp Pro Tyr Ile
        355                 360                 365

Leu Leu Val Ser Ser Lys Val Ser Thr Val Lys Asp Leu Leu Pro Leu
    370                 375                 380

Leu Glu Lys Val Ile Gly Ala Gly Lys Pro Leu Leu Ile Ile Ala Glu
385                 390                 395                 400

Asp Val Glu Gly Glu Ala Leu Ser Thr Leu Val Val Asn Lys Ile Arg
                405                 410                 415

Gly Thr Phe Lys Ser Val Ala Val Lys Ala Pro Gly Phe Gly Asp Arg
            420                 425                 430

Arg Lys Ala Met Leu Gln Asp Met Ala Ile Leu Thr Gly Gly Gln Val
        435                 440                 445

Ile Ser Glu Glu Val Gly Leu Thr Leu Glu Asn Ala Asp Leu Ser Leu
    450                 455                 460

Leu Gly Lys Ala Arg Lys Val Val Thr Lys Asp Glu Thr Thr Ile
465                 470                 475                 480

Val Glu Gly Ala Gly Asp Thr Asp Ala Ile Ala Gly Arg Val Ala Gln
                485                 490                 495

Ile Arg Gln Glu Ile Glu Asn Ser Asp Ser Asp Tyr Asp Arg Glu Lys
            500                 505                 510

Leu Gln Glu Arg Leu Ala Lys Leu Ala Gly Gly Val Ala Val Ile Lys
        515                 520                 525

Ala Gly Ala Ala Thr Glu Val Glu Leu Lys Glu Arg Lys His Arg Ile
    530                 535                 540

Glu Asp Ala Val Arg Asn Ala Lys Ala Ala Val Glu Glu Gly Ile Val
545                 550                 555                 560

Ala Gly Gly Gly Val Thr Leu Leu Gln Ala Ala Pro Thr Leu Asp Glu
                565                 570                 575

Leu Lys Leu Glu Gly Asp Glu Ala Thr Gly Ala Asn Ile Val Lys Val
            580                 585                 590

Ala Leu Glu Ala Pro Leu Lys Gln Ile Ala Phe Asn Ser Gly Leu Glu
        595                 600                 605

Pro Gly Val Val Ala Glu Lys Val Arg Asn Leu Pro Ala Gly His Gly
    610                 615                 620

Leu Asn Ala Gln Thr Gly Val Tyr Glu Asp Leu Leu Ala Ala Gly Val
625                 630                 635                 640

Ala Asp Pro Val Lys Val Thr Arg Ser Ala Leu Gln Asn Ala Ala Ser
                645                 650                 655
```

-continued

```
Ile Ala Gly Leu Phe Leu Thr Thr Glu Ala Val Val Ala Asp Lys Pro
            660                 665                 670

Glu Lys Glu Lys Ala Ser Val Pro Gly Gly Gly Asp Met Gly Gly Met
        675                 680                 685

Asp Phe
    690

<210> SEQ ID NO 11
<211> LENGTH: 2175
<212> TYPE: DNA
<213> ORGANISM: Artificial Sequence
<220> FEATURE:
<221> NAME/KEY: CDS
<222> LOCATION: (1)...(2172)
<223> OTHER INFORMATION: Nucleic acids encoding fusion protein

<400> SEQUENCE: 11 atg gac att gac cct tat aaa gaa ttt gga gct act gtg gag tta ctc      48
Met Asp Ile Asp Pro Tyr Lys Glu Phe Gly Ala Thr Val Glu Leu Leu
  1               5                  10                  15 tcg ttt ttg cct tct gac ttc ttt cct tcc gtc aga gat ctc cta gac      96
Ser Phe Leu Pro Ser Asp Phe Phe Pro Ser Val Arg Asp Leu Leu Asp
             20                  25                  30 acc gcc tca gct ctg tat cgg gaa gcc tta gag tct cct gag cat tgc     144
Thr Ala Ser Ala Leu Tyr Arg Glu Ala Leu Glu Ser Pro Glu His Cys
         35                  40                  45 tca cct cac cac acc gca ctc agg caa gcc att ctc tgc tgg ggg gaa     192
Ser Pro His His Thr Ala Leu Arg Gln Ala Ile Leu Cys Trp Gly Glu
     50                  55                  60 ttg atg act cta gct acc tgg gtg ggt aat aat ttg gaa gat cca gca     240
Leu Met Thr Leu Ala Thr Trp Val Gly Asn Asn Leu Glu Asp Pro Ala
 65                  70                  75                  80 tca agg gat cta gta gtc aat tat gtt aat act aac atg ggt tta aaa     288
Ser Arg Asp Leu Val Val Asn Tyr Val Asn Thr Asn Met Gly Leu Lys
                 85                  90                  95 ttt agg caa cta ttg tgg ttt cat ata tct tgc ctt act ttt gga aga     336
Phe Arg Gln Leu Leu Trp Phe His Ile Ser Cys Leu Thr Phe Gly Arg
            100                 105                 110 gag act gta ctt gaa tat ttg gta tct ttc gga gtg tgg att cgc act     384
Glu Thr Val Leu Glu Tyr Leu Val Ser Phe Gly Val Trp Ile Arg Thr
        115                 120                 125 cct cca gcc tat aga cca cca aat gcc cct atc tta tca aca ctt ccg     432
Pro Pro Ala Tyr Arg Pro Pro Asn Ala Pro Ile Leu Ser Thr Leu Pro
    130                 135                 140 gaa act act gtt gtt aga cga cgg gac cga ggc agg tcc cct aga aga     480
Glu Thr Thr Val Val Arg Arg Arg Asp Arg Gly Arg Ser Pro Arg Arg
145                 150                 155                 160 aga act ccc tcg cct cgc aga cgc aga tct caa tcg ccg cgt cgc aga     528
Arg Thr Pro Ser Pro Arg Arg Arg Ser Gln Ser Pro Arg Arg Arg
                165                 170                 175 aga tct caa tct cgg gaa tct caa tgt gcc aag aca att gcg tac gac     576
Arg Ser Gln Ser Arg Glu Ser Gln Cys Ala Lys Thr Ile Ala Tyr Asp
            180                 185                 190 gaa gag gcc cgt cgc ggc ctc gag cgg ggc ttg aac gcc ctc gcc gat     624
Glu Glu Ala Arg Arg Gly Leu Glu Arg Gly Leu Asn Ala Leu Ala Asp
        195                 200                 205 gcg gta aag gtg aca ttg ggc ccc aag ggc cgc aac gtc gtc ctg gaa     672
Ala Val Lys Val Thr Leu Gly Pro Lys Gly Arg Asn Val Val Leu Glu
    210                 215                 220 aag aag tgg ggt gcc ccc acg atc acc aac gat ggt gtg tcc atc gcc     720
Lys Lys Trp Gly Ala Pro Thr Ile Thr Asn Asp Gly Val Ser Ile Ala
```

```
                    225                 230                 235                 240
aag gag atc gag ctg gag gat ccg tac gag aag atc ggc gcc gag ctg         768
Lys Glu Ile Glu Leu Glu Asp Pro Tyr Glu Lys Ile Gly Ala Glu Leu
                        245                 250                 255 gtc aaa gag gta gcc aag aag acc gat gac gtc gcc ggt gac ggc acc         816
Val Lys Glu Val Ala Lys Lys Thr Asp Asp Val Ala Gly Asp Gly Thr
                260                 265                 270 acg acg gcc acc gtg ctg gcc cag gcg ttg gtt cgc gag ggc ctg cgc         864
Thr Thr Ala Thr Val Leu Ala Gln Ala Leu Val Arg Glu Gly Leu Arg
            275                 280                 285 aac gtc gcg gcc ggc gcc aac ccg ctc ggt ctc aaa cgc ggc atc gaa         912
Asn Val Ala Ala Gly Ala Asn Pro Leu Gly Leu Lys Arg Gly Ile Glu
        290                 295                 300 aag gcc gtg gag aag gtc acc gag acc ctg ctc aag ggc gcc aag gag         960
Lys Ala Val Glu Lys Val Thr Glu Thr Leu Leu Lys Gly Ala Lys Glu
305                 310                 315                 320 gtc gag acc aag gag cag att gcg gcc acc gca gcg att tcg gcg ggt        1008
Val Glu Thr Lys Glu Gln Ile Ala Ala Thr Ala Ala Ile Ser Ala Gly
                    325                 330                 335 gac cag tcc atc ggt gac ctg atc gcc gag gcg atg gac aag gtg ggc        1056
Asp Gln Ser Ile Gly Asp Leu Ile Ala Glu Ala Met Asp Lys Val Gly
                340                 345                 350 aac gag ggc gtc atc acc gtc gag gag tcc aac acc ttt ggg ctg cag        1104
Asn Glu Gly Val Ile Thr Val Glu Glu Ser Asn Thr Phe Gly Leu Gln
            355                 360                 365 ctc gag ctc acc gag ggt atg cgg ttc gac aag ggc tac atc tcg ggg        1152
Leu Glu Leu Thr Glu Gly Met Arg Phe Asp Lys Gly Tyr Ile Ser Gly
        370                 375                 380 tac ttc gtg acc gac ccg gag cgt cag gag gcg gtc ctg gag gac ccc        1200
Tyr Phe Val Thr Asp Pro Glu Arg Gln Glu Ala Val Leu Glu Asp Pro
385                 390                 395                 400 tac atc ctg ctg gtc agc tcc aag gtg tcc act gtc aag gat ctg ctg        1248
Tyr Ile Leu Leu Val Ser Ser Lys Val Ser Thr Val Lys Asp Leu Leu
                    405                 410                 415 ccg ctg ctc gag aag gtc atc gga gcc ggt aag ccg ctg ctg atc atc        1296
Pro Leu Leu Glu Lys Val Ile Gly Ala Gly Lys Pro Leu Leu Ile Ile
                420                 425                 430 gcc gag gac gtc gag ggc gag gcg ctg tcc acc ctg gtc gtc aac aag        1344
Ala Glu Asp Val Glu Gly Glu Ala Leu Ser Thr Leu Val Val Asn Lys
            435                 440                 445 atc cgc ggc acc ttc aag tcg gtg gcg gtc aag gct ccc ggc ttc ggc        1392
Ile Arg Gly Thr Phe Lys Ser Val Ala Val Lys Ala Pro Gly Phe Gly
        450                 455                 460 gac cgc cgc aag gcg atg ctg cag gat atg gcc att ctc acc ggt ggt        1440
Asp Arg Arg Lys Ala Met Leu Gln Asp Met Ala Ile Leu Thr Gly Gly
465                 470                 475                 480 cag gtg atc agc gaa gag gtc ggc ctg acg ctg gag aac gcc gac ctg        1488
Gln Val Ile Ser Glu Glu Val Gly Leu Thr Leu Glu Asn Ala Asp Leu
                    485                 490                 495 tcg ctg cta ggc aag gcc cgc aag gtc gtg gtc acc aag gac gag acc        1536
Ser Leu Leu Gly Lys Ala Arg Lys Val Val Val Thr Lys Asp Glu Thr
                500                 505                 510 acc atc gtc gag ggc gcc ggt gac acc gac gcc atc gcc gga cga gtg        1584
Thr Ile Val Glu Gly Ala Gly Asp Thr Asp Ala Ile Ala Gly Arg Val
            515                 520                 525 gcc cag atc cgc cag gag atc gag aac agc gac tcc gac tac gac cgt        1632
Ala Gln Ile Arg Gln Glu Ile Glu Asn Ser Asp Ser Asp Tyr Asp Arg
        530                 535                 540 gag aag ctg cag gag cgg ctg gcc aag ctg gcc ggt ggt gtc gcg gtg        1680
```

```
Glu Lys Leu Gln Glu Arg Leu Ala Lys Leu Ala Gly Val Ala Val
545                 550                 555                 560 atc aag gcc ggt gcc gcc acc gag gtc gaa ctc aag gag cgc aag cac      1728
Ile Lys Ala Gly Ala Ala Thr Glu Val Glu Leu Lys Glu Arg Lys His
                565                 570                 575 cgc atc gag gat gcg gtt cgc aat gcc aag gcc gcc gtc gag gag ggc      1776
Arg Ile Glu Asp Ala Val Arg Asn Ala Lys Ala Ala Val Glu Glu Gly
            580                 585                 590 atc gtc gcc ggt ggg ggt gtg acg ctg ttg caa gcg gcc ccg acc ctg      1824
Ile Val Ala Gly Gly Gly Val Thr Leu Leu Gln Ala Ala Pro Thr Leu
        595                 600                 605 gac gag ctg aag ctc gaa ggc gac gag gcg acc ggc gcc aac atc gtg      1872
Asp Glu Leu Lys Leu Glu Gly Asp Glu Ala Thr Gly Ala Asn Ile Val
    610                 615                 620 aag gtg gcg ctg gag gcc ccg ctg aag cag atc gcc ttc aac tcc ggg      1920
Lys Val Ala Leu Glu Ala Pro Leu Lys Gln Ile Ala Phe Asn Ser Gly
625                 630                 635                 640 ctg gag ccg ggc gtg gtg gcc gag aag gtg cgc aac ctg ccg gct ggc      1968
Leu Glu Pro Gly Val Val Ala Glu Lys Val Arg Asn Leu Pro Ala Gly
                645                 650                 655 cac gga ctg aac gct cag acc ggt gtc tac gag gat ctg ctc gct gcc      2016
His Gly Leu Asn Ala Gln Thr Gly Val Tyr Glu Asp Leu Leu Ala Ala
            660                 665                 670 ggc gtt gct gac ccg gtc aag gtg acc cgt tcg gcg ctg cag aat gcg      2064
Gly Val Ala Asp Pro Val Lys Val Thr Arg Ser Ala Leu Gln Asn Ala
        675                 680                 685 gcg tcc atc gcg ggg ctg ttc ctg acc acc gag gcc gtc gtt gcc gac      2112
Ala Ser Ile Ala Gly Leu Phe Leu Thr Thr Glu Ala Val Val Ala Asp
    690                 695                 700 aag ccg gaa aag gag aag gct tcc gtt ccc ggt ggc ggc gac atg ggt      2160
Lys Pro Glu Lys Glu Lys Ala Ser Val Pro Gly Gly Gly Asp Met Gly
705                 710                 715                 720 ggc atg gat ttc tga                                                   2175
Gly Met Asp Phe <210> SEQ ID NO 12
<211> LENGTH: 724
<212> TYPE: PRT
<213> ORGANISM: Artificial Sequence
<220> FEATURE:
<223> OTHER INFORMATION: Fusion protein

<400> SEQUENCE: 12

Met Asp Ile Asp Pro Tyr Lys Glu Phe Gly Ala Thr Val Glu Leu Leu
 1               5                  10                  15

Ser Phe Leu Pro Ser Asp Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125
```

```
Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                     150                 155                 160

Arg Thr Pro Ser Pro Arg Arg Arg Ser Gln Ser Pro Arg Arg Arg
            165                 170                 175

Arg Ser Gln Ser Arg Glu Ser Gln Cys Ala Lys Thr Ile Ala Tyr Asp
            180                 185                 190

Glu Glu Ala Arg Arg Gly Leu Glu Arg Gly Leu Asn Ala Leu Ala Asp
                195                 200                 205

Ala Val Lys Val Thr Leu Gly Pro Lys Gly Arg Asn Val Val Leu Glu
    210                 215                 220

Lys Lys Trp Gly Ala Pro Thr Ile Thr Asn Asp Gly Val Ser Ile Ala
225                 230                 235                 240

Lys Glu Ile Glu Leu Glu Asp Pro Tyr Glu Lys Ile Gly Ala Glu Leu
                245                 250                 255

Val Lys Glu Val Ala Lys Lys Thr Asp Asp Val Ala Gly Asp Gly Thr
            260                 265                 270

Thr Thr Ala Thr Val Leu Ala Gln Ala Leu Val Arg Glu Gly Leu Arg
            275                 280                 285

Asn Val Ala Ala Gly Ala Asn Pro Leu Gly Leu Lys Arg Gly Ile Glu
    290                 295                 300

Lys Ala Val Glu Lys Val Thr Glu Thr Leu Leu Lys Gly Ala Lys Glu
305                 310                 315                 320

Val Glu Thr Lys Glu Gln Ile Ala Ala Thr Ala Ala Ile Ser Ala Gly
                325                 330                 335

Asp Gln Ser Ile Gly Asp Leu Ile Ala Glu Ala Met Asp Lys Val Gly
            340                 345                 350

Asn Glu Gly Val Ile Thr Val Glu Glu Ser Asn Thr Phe Gly Leu Gln
            355                 360                 365

Leu Glu Leu Thr Glu Gly Met Arg Phe Asp Lys Gly Tyr Ile Ser Gly
    370                 375                 380

Tyr Phe Val Thr Asp Pro Glu Arg Gln Glu Ala Val Leu Glu Asp Pro
385                 390                 395                 400

Tyr Ile Leu Leu Val Ser Ser Lys Val Ser Thr Val Lys Asp Leu Leu
                405                 410                 415

Pro Leu Leu Glu Lys Val Ile Gly Ala Gly Lys Pro Leu Leu Ile Ile
            420                 425                 430

Ala Glu Asp Val Glu Gly Glu Ala Leu Ser Thr Leu Val Val Asn Lys
            435                 440                 445

Ile Arg Gly Thr Phe Lys Ser Val Ala Val Lys Ala Pro Gly Phe Gly
    450                 455                 460

Asp Arg Arg Lys Ala Met Leu Gln Asp Met Ala Ile Leu Thr Gly Gly
465                 470                 475                 480

Gln Val Ile Ser Glu Glu Val Gly Leu Thr Leu Glu Asn Ala Asp Leu
                485                 490                 495

Ser Leu Leu Gly Lys Ala Arg Lys Val Val Thr Lys Asp Glu Thr
            500                 505                 510

Thr Ile Val Glu Gly Ala Gly Asp Thr Asp Ala Ile Ala Gly Arg Val
            515                 520                 525

Ala Gln Ile Arg Gln Glu Ile Glu Asn Ser Asp Ser Asp Tyr Asp Arg
    530                 535                 540
```

```
Glu Lys Leu Gln Glu Arg Leu Ala Lys Leu Ala Gly Gly Val Ala Val
545                 550                 555                 560

Ile Lys Ala Gly Ala Ala Thr Glu Val Glu Leu Lys Glu Arg Lys His
                565                 570                 575

Arg Ile Glu Asp Ala Val Arg Asn Ala Lys Ala Ala Val Glu Glu Gly
            580                 585                 590

Ile Val Ala Gly Gly Gly Val Thr Leu Leu Gln Ala Ala Pro Thr Leu
        595                 600                 605

Asp Glu Leu Lys Leu Glu Gly Asp Glu Ala Thr Gly Ala Asn Ile Val
        610                 615                 620

Lys Val Ala Leu Glu Ala Pro Leu Lys Gln Ile Ala Phe Asn Ser Gly
625                 630                 635                 640

Leu Glu Pro Gly Val Val Ala Glu Lys Val Arg Asn Leu Pro Ala Gly
                645                 650                 655

His Gly Leu Asn Ala Gln Thr Gly Val Tyr Glu Asp Leu Leu Ala Ala
            660                 665                 670

Gly Val Ala Asp Pro Val Lys Val Thr Arg Ser Ala Leu Gln Asn Ala
        675                 680                 685

Ala Ser Ile Ala Gly Leu Phe Leu Thr Thr Glu Ala Val Val Ala Asp
    690                 695                 700

Lys Pro Glu Lys Glu Lys Ala Ser Val Pro Gly Gly Gly Asp Met Gly
705                 710                 715                 720

Gly Met Asp Phe
```